United States Patent [19]

Rando

[11] Patent Number: 6,015,877
[45] Date of Patent: *Jan. 18, 2000

[54] COMPOUNDS FOR INHIBITION OF PROTEOLYSIS

[75] Inventor: Robert R. Rando, Newton Centre, Mass.

[73] Assignee: President and Fellows of Harvard College, Cambridge, Mass.

[ * ] Notice: This patent is subject to a terminal disclaimer.

[21] Appl. No.: 08/616,995

[22] Filed: Mar. 14, 1996

Related U.S. Application Data

[63] Continuation-in-part of application No. 08/362,605, filed as application No. PCT/US93/06593, Jul. 14, 1993, Pat. No. 5,789,541, which is a continuation-in-part of application No. 07/914,164, Jul. 14, 1992, abandoned.

[51] Int. Cl.$^7$ ............................. A61K 38/00; A61K 38/04
[52] U.S. Cl. .......................... 530/326; 530/330; 530/331; 514/13; 514/18
[58] Field of Search ...................................... 530/326, 330, 530/331; 514/13, 18

[56] References Cited

U.S. PATENT DOCUMENTS 5,202,456  4/1993  Rando .

OTHER PUBLICATIONS

Tan et al., J. Am. Chem. Soc., vol. 113., pp. 6299–6300., 1991.
Ashby et al., "Endoproteolytic processing of a farnesylated peptide in vitro", Proc. Nat'l. Acad. Sci. USA, 89:4613–4617, 1992.
Chen et al., "Solubilization, Partial Purification, and Affinity Labeling of the Membrane–Bound Isoprenylated Protein Endoprotease", Biochemistry, 35:3227–3237, 1996.
Lai et al., "The γ Subunit of transducin is farnesylated", Proc. Nat'l Acad. Sci. USA, 87:7673–7677, 1990.
Ma et al., "A microsomal endoprotease that specifically cleaves isoprenylated peptides", Proc. Nat'l. Acad. Sci. USA, 1992, pp. 6275–6279.
Ma et al., "Inhibitors of the Isoprenylated Protein Endoprotease", Biochemistry, 32:2386–2393, 1993.
Ma et al., "Mechanistic Studies on Human Platelet Isoprenylated Protein Methyltransferase: Farnesylcysteine Analogs Block Platelet Aggregation without inhibiting the Methyltransferase", Biochem. 33:5414–5420, 1994.
Perez–Sala et al., "Methylation and demethylation reactions of guanine nucleotide–binding proteins of retinal rod outer segments", Proc. Nat'l. Acad. Sci. USA, 88:3043–3046, 1991.

*Primary Examiner*—Keith D. MacMillan
*Assistant Examiner*—P. Ponnaluri
*Attorney, Agent, or Firm*—Fish & Richardson P.C.

[57] ABSTRACT

Compounds used to treat cancer which inhibit carboxy terminal proteolysis of proteins having a carboxyl-terminal - CAAX motif (C=cysteine, A=aliphatic amino acid, and X=any amino acid). The compounds have the formula W—Y—CH$_2$—Q, where:

1) W is a substituted or unsubstituted farnesyl group, a substituted or unsubstituted geranylgeranyl group, or a lipophilic alkyl, alkenyl, aryl or arylalkyl hydrocarbon group;
2) Y is:

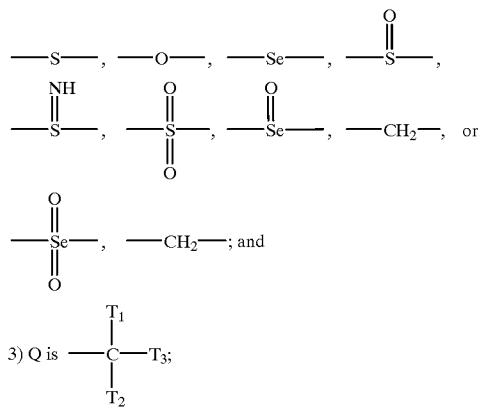

3) Q is:

wherein
T$_1$ is: —H, —CH$_3$, —F, or —(CH$_2$)$_n$—X$_1$; in which n is an integer <20; and X$_1$ is: —SH, —COOH, or —CONH$_2$;
T$_2$ is: —N-benzxyloxycarbonyl (Boc), N—φ—, in which φ is an amino acid or a polypeptide reside; and

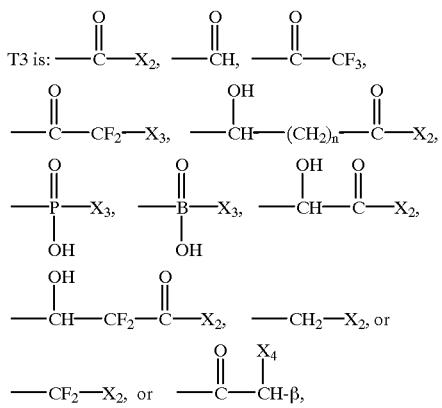

wherein
X$_2$ is a peptide residue linked to carbon via the amino terminal nitrogen; and X$_3$ is a peptide residue linked via an alpha carbon of the peptide; n is an integer <20, X$_4$ is a halide and β is an amino acid residue.

13 Claims, 28 Drawing Sheets

NOT AN INHIBITOR

INHIBITOR

INHIBITOR

SYNTHESIS OF REDUCED PEPTIDES AS INHIBITORS

AFFINITY LABELING OF THE ENDOPROTEASE

TPCK; K₁ = 1.1 mM,
ki = 1.4 x 10⁻³s⁻¹

TLCK; inert

2-Nal-Ala-CMK; -TPCK

BFCCMK; K₁ = 30μM,
ki = 5.9 x 10⁻³s⁻¹

ZGGFCCMK; -BFCCMK

| COMPOUND | STRUCTURE | $K_I$ | $K_{inh}/[I]$ or $K_{inh}/K_I$ ($M^{-1}$ $min^{-1}$) |
|---|---|---|---|
| N-Biotinyl-S-farnesyl Cysteine Chloromethyl Ketone NMR, Mass, and TLC | 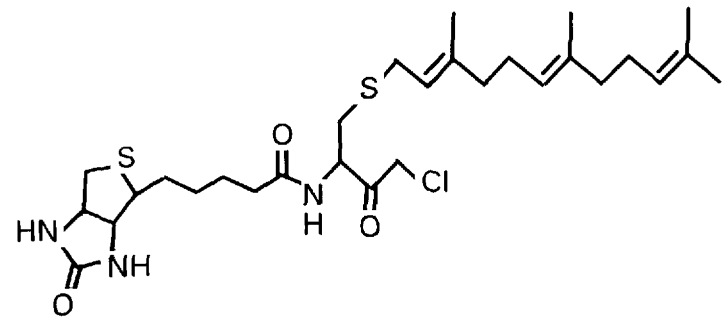 | 59±1 | 1918±36 |
| N-Boc-S-Dodecyl Cysteine Chloromethyl Ketone NMR, Mass, and TLC | 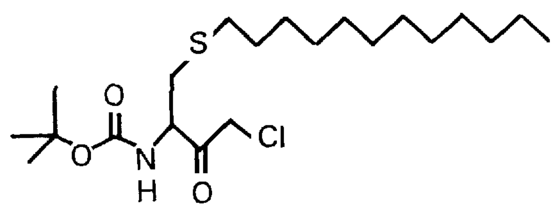 | [I] = 5uM | 3540±150 |
| N-Boc-S-Decyl Cysteine Chloromethyl Ketone (crude) TLC data | 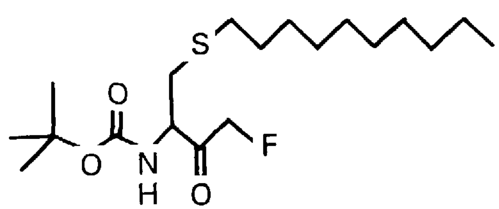 | | not determined |

FIG. 22

COMPOUNDS FOR INHIBITION OF PROTEOLYSIS

This is a continuation-in-part of my commonly owned application U.S. Ser. No. 08/362,605, filed Feb. 13, 1995, now U.S. Pat. No. 5,789,541, (national phase of PCT U.S. Ser. No. 093/06593, filed Jul. 14, 1993), which in turn was a continuation in part of U.S. Ser. No. 07/914,164, filed Jul. 14, 1992, now abandoned. Each of these applications is hereby incorporated by reference.

This invention was supported by Grant No. EY03624 and the government has certain rights to the invention.

BACKGROUND OF THE INVENTION

This invention relates to controlling neoplastic cell growth.

Activated ras genes have been associated with a number of human cancers. An activated ras gene, H-ras-1, was the first non-viral oncogene discovered. Several other human ras proto-onco genes have subsequently been identified including H-ras-2, K-ras-1, K-ras-2, and N-ras. For each of these ras genes several activated mutant forms have been identified. Activated K-ras genes have been detected in pre-malignant neoplasms of the human colon and in human pre-leukemia.

The ras proteins, and ras-like proteins, as well as other proteins such as signal transducing G proteins, have a conserved carboxyl-terminal -CAAX motif (C=cysteine, A=aliphatic amino acid, and X=any amino acid) (SEQ ID NO: 3). This motif is involved in a series of post-translational modifications including polyisoprenylation, carboxyl-terminal proteolysis, and carboxyl-methylation. A number of ras-related small GTP binding proteins including R-ras, RAS2, rap-2, and phoB also have a carboxyl-terminal -CAAX motif, and it has been suggested that these proteins may be post-translationally modified in the same manner (Hancock et al., Cell 57:1167, 1989). Among ras proteins, H-ras, N-ras (Gutierrez et al., EMBO J., 8:1093, 1989) and K-ras (Hancock et al., Cell, 57:1167, 1989) undergo polyisoprenylation, carboxyl-terminal proteolysis and carboxyl-methylation. Inhibition of these modifications by mutation of $Cys^{186}$ to Ser blocks both membrane localization of ras gene product and transformation of the cell (Willumsen et al., EMBO J. 3:2581; Gutierrez et al., EMBO J. 8:1093, 1989).

A number of other proteins which have a carboxyl-terminal -CAAX motif including the γ-subunit of transducing (Lai et al., Proc. Natl. Acad. Sci. USA, 87:7673, 1990), yeast mating factor mata (Anderegg et al., J. Biol. Chem., 263:18236, 1988), and nuclear lamin B (Chelsky et al., J. Biol. Chem., 262:4303, 1987; Farnsworth et al., J. Biol. Chem., 264:20422, 1989; Vorburger et al., EMBO J., 8:4007, 1989) have also been shown to undergo polyisoprenylation, carboxyl-terminal proteolysis, and carboxyl-methylation.

Analysis of in vitro translated K-ras demonstrated that farnesylated, non-proteolysed, non-methylated K-ras associates inefficiently with cell membranes. Removal of the carboxyl-terminal three amino acids of this K-ras product increases membrane binding 2-fold, and methylation of the K-ras product increases membrane binding another two-fold (Hancock et al., EMBO J. 10:641, 1991).

Mevinolin inhibits cellular synthesis of mevalonic acid; this leads to depletion of polyisoprenoids and is expected to interfere with polyisoprenylation reactions. Mevinolin affects post-translational processing of ras proteins and interferes with ras membrane localization (Hancock et al., Cell 57:1167, 1989). In addition, cells treated with mevinolin are blocked in cell growth in the G1 phase and the G2/M phase (Maltese et al., J. Cell Physiol. 125:540, 1985). It has been proposed that this growth arrest, which is associated with the inhibition of mevalonate incorporation into polypeptides but not other isoprenoid derivatives such as cholesterol (Sinensky et al., Proc. Natl. Acad. Sci. USA, 82:3257, 1985), is caused by disruption of nuclear lamin B function (Beck et al., J. Cell. Biol., 107:1307, 1988). The observation that mevinolin interferes with post-translational modification of the ras gene product combined with involvement of activated ras genes in human malignancies has led to the suggestion that mevinolin or derivatives of mevinolin may prove to be novel cytotoxic/static agents or even a starting point for the development of an anti-ras drug (Hancock et al., Cell 57:1167, 1989).

Hancock et al. (EMBO J. 10:641, 1991) report that a proteolytic activity capable of removing the -AAX motif of $p21^{K-ras(B)}$ is associated with microsomal membranes.

Ashby et al. (Proc. Nat'l. Acad. Sci. USA 89:4613, 1992) report that yeast have three proteolytic activities which, when incubated with farnesylated yeast a-factor octapeptide, release the terminal three amino acids as a tripeptide.

SUMMARY OF THE INVENTION

In general, the invention features certain novel compounds which inhibit carboxy terminal proteolysis of proteins having a carboxyl-terminal -CAAX motif (C=cysteine, A=aliphatic amino acid, and X=any amino acid) (SEQ ID NO: 3).

In general, the invention features compounds having the formula W—Y—CH$_2$—Q wherein W is a farnesyl group, a geranylgeranyl group, a substituted farnesyl group or a substituted geranylgeranyl group; Y is:

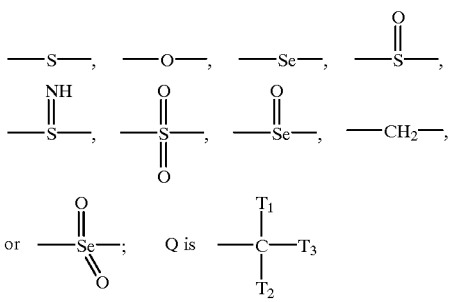

$T_1$ is: H, F, or —(CH$_2$)$_n$—X$_1$;
$T_2$ is: —NHCOCH$_3$, —NH—(CH$_2$)$_n$—X$_1$,

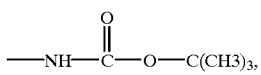

or a peptide of 20 or fewer amino acids, preferably 15 or fewer amino acids, more preferably 10 or fewer amino acids, even more preferably 5 or fewer amino acids, still more preferably 3 or fewer amino acids, linked to carbon via the amino terminal nitrogen of the peptide, and n is an integer less than 20, preferably less than 10, more preferably less than 5, still more preferably less than 3, yet more preferably 1 or 2; wherein $X_1$ is: —SH, —COOH, —CONH$_2$

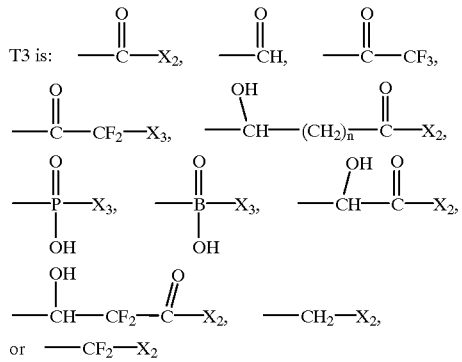

wherein $X_2$ is a peptide of 20 or fewer amino acids, preferably 15 or fewer amino acids, more preferably 10 or fewer amino acids, even more preferably 5 or fewer amino acids, still more preferably 3 or fewer amino acids, linked to carbon via the amino terminal nitrogen of the peptide, n is an integer less than 20, preferably less than 10, more preferably less than 5, still more preferably less than three, yet more preferably 1 or 2; $X_3$ is a peptide of 20 or fewer amino acids, preferably 15 or fewer amino acids, more preferably 10 or fewer amino acids, even more preferably 5 or fewer amino acids, still more preferably 3 or fewer amino acids, yet more preferably 1 or 2 amino acids, linked to carbon via the alpha carbon of one of the amino acids of the peptide, preferably the amino terminal amino acid of the peptide.

Regarding the farnesyl and geranylgeranyl moieties, hydrogen may generally be replaced by fluorine and a methyl group may generally be replaced by a bromine. Accordingly, "substituted farnesyl group" means a farnesyl moiety in which one or more hydrogens have been replaced by fluorine or one or more methyl groups have been replaced by a bromine, and "substituted geranylgeranyl group" means a geranylgeranyl moiety in which one or more hydrogens have been replaced by fluorine or one or more methyl groups have been replaced by bromine.

In addition, the farnesyl or geranylgeranyl group may be replaced by a structurally related moiety. Such related moieties include generally lipophilic hydrocarbons including group of aromatic rings. Preferred hydrocarbons include 5 to 15, preferably 10 carbons. Preferred moieties are those which closely resemble farnesyl in structure.

Preferred compounds include:

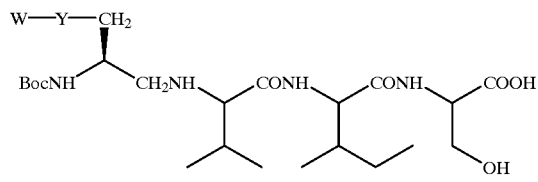

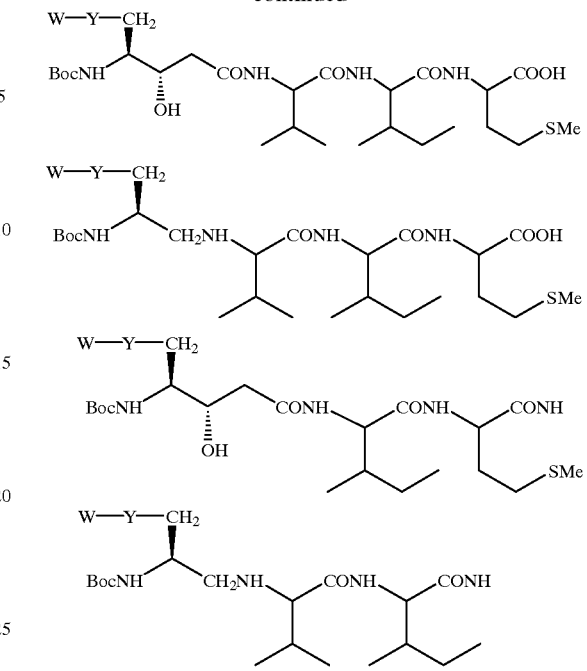

wherein BocNH is

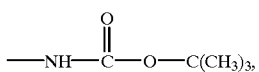

W is farnesyl, and
Y is —S—.

The compounds of the invention may be either classic competitive inhibitors or, in a less preferred alternative, an enzyme substrate that has a Km low enough to cause an effective reduction in proteolysis of the normal protein substrate (e.g., the ras gene product). Standard assays may be used to determine Km for substrates and Ki for inhibitors. Generally preferred compounds have small values of Ki or Km. The values of Ki and Km are calculated from kinetic assays by conventional means (Fersht, Enzyme Structure and Mechanism, W.H. Freeman and Co., New York, 1984). Examples are provided below to illustrate suitable assays, and are not intended to limit the invention.

In a related aspect, the invention features a therapeutic composition which includes the above-described compound capable of inhibiting carboxy terminal proteolysis of a protein having a carboxyl terminal -CAAX motif (SEQ ID NO: 3).

In a related aspect, the invention features a method for controlling neoplastic cell growth in a patient. The method includes administering to the patient the a therapeutic composition comprising the above described compound.

In another aspect, W may also be a lipophilic alkyl, alkenyl, aryl or arylalkyl hydrocarbon group having between 10 and 20 carbon atoms; and $T_1$ may be: H, F, CH$_3$, or —(CH$_2$)$_n$—X$_1$; and $T_2$ may be N-benzyloxycarbonyl (Boc); and $T_3$ may be:

where A is a halogen or —H, and B is an amino acid.

Other features and advantages of the invention will be apparent from the following description of the preferred embodiments and from the claims.

BRIEF DESCRIPTION OF THE DRAWING

FIGS. 16A1 and 16A2 and 16B illustrate inhibition of the enzyme.

FIGS. 18–22 depict synthetic schemes and formulae of inhibitors and other compounds.

DESCRIPTION OF THE PREFERRED EMBODIMENT(S)

Figure 1:
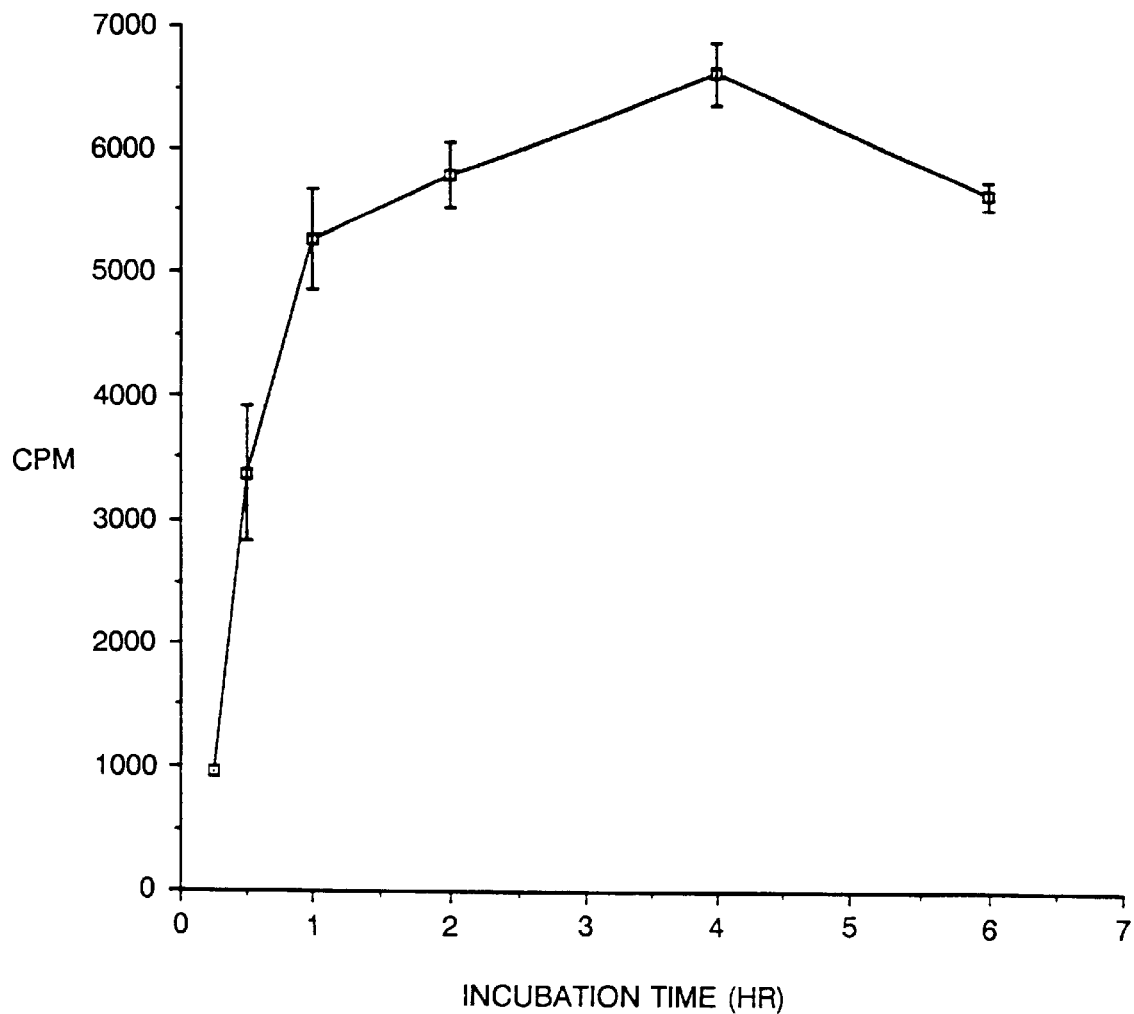
FIG. 1 is a graph which illustrates the time-dependent hydrolysis of N-[$^3$H]acetyl-S-farnesyl-L-cys-L-val-L-ile-L-ser N-[$^3$H]acetyl-S-farnesyl-(SEQ ID NO: 1) in the presence of a bovine liver microsomal membrane preparation. N-[$^3$H]acetyl-S-all-trans-farnesyl-L-cysteine released (cpm) is plotted as a function of incubation time (min).

Described below is the characterization of a microsomal enzymatic activity which can specifically cleave the tetrapeptide N-acetyl-S-farnesyl-L-cys-L-val-L-ile-L-ser or N-[$^3$H]acetyl-S-farnesyl-(Seq. ID NO: 1) between the isoprenylated cysteine residue and the valine residue. This activity is likely to be similar to the activity responsible for the carboxyl-terminal proteolysis step of the above-described post-translational modification of -CAAX motif proteins. Also described are certain compounds which are characterized by the ability to inhibit this proteolysis. The compounds may be either classic competitive inhibitors or, in a less preferred alternative, an enzyme substrate that has Km low enough to cause an effective reduction in proteolysis of the normal protein substrate (e.g. the ras gene product). Such compounds will be useful for inhibiting the activity of certain proteins, e.g., ras proteins. Standard assays may be used to determine Km for substrates and Ki for inhibitors. Generally preferred compounds have small values of Ki or Km. The values of Ki and Km are calculated from kinetic assays by conventional means (Fersht, Enzyme Structure and Mechanism, W.H. Freeman and Co., New York, 1984). Examples are provided below to illustrate suitable assays, and are not intended to limit the invention. Also described is a method for using the microsomal enzymatic activity to screen compounds for their ability to inhibit complete post-translation modification.

For all experiments described herein amino acids and dipeptides were purchased from Bachem Inc. β-mercaptoethanol, o-phthalaldehyde, all-<u>trans</u>-farnesyl bromide, all-<u>trans</u>-farnesol, 4,4-dimethylaminopyridine, general 1-hydroxybenzotriazole hydrate, 1-(3-dimethylamino)propyl-3-ethyl carbodiimide hydrochloride, N-methylmorpholine, and 1-hydroxybenzotriazole hydrate were purchased from the Aldrich Chemical Co. All-<u>trans</u>-geranylgeraniol was from TCI, Inc. HPLC solvents were from J. T. Baker Inc. All chemicals and solvents purchased were of the highest purity available. [$^3$H]-L-serine and [$^3$H]-acetic anhydride were from New England Nuclear Inc. Dog pancreatic microsomes were purchased from Promega Inc. Fresh bovine calf liver was obtained from a slaughter house. Cys-Val-Ile and t-butylthio Cys-Val-Ile were synthesized by a automated peptide synthesizer and were isoprenylated as described below.

Enzymatic Hydrolysis of a Synthetic Tetrapeptide

N-acetyl-S-farnesyl-L-cysteine-L-val-L-ile-L-ser (AFC-val-ile-ser or N-[$^3$H]acetyl-S-farnesyl-(SEQ ID NO: 1); all L amino acids; synthesis described below) 1 was chosen as a synthetic substrate for the protease. This sequence is taken from the carboxyl terminus of the γ subunit of the retinal heterotrimeric G protein transducing. The γ subunit of transducing has previously been shown to be farnesylated and methylated (Fukada et al., Nature 346:658, 1990).

Incubation of the above mentioned tetrapeptide (labelled with an $^3$H-acetyl group) with a calf liver microsomal enzyme preparation led to the time dependent formation of N-acetyl-S-all-trans-farnesyl-L-cysteine (AFC).

Figure 2:
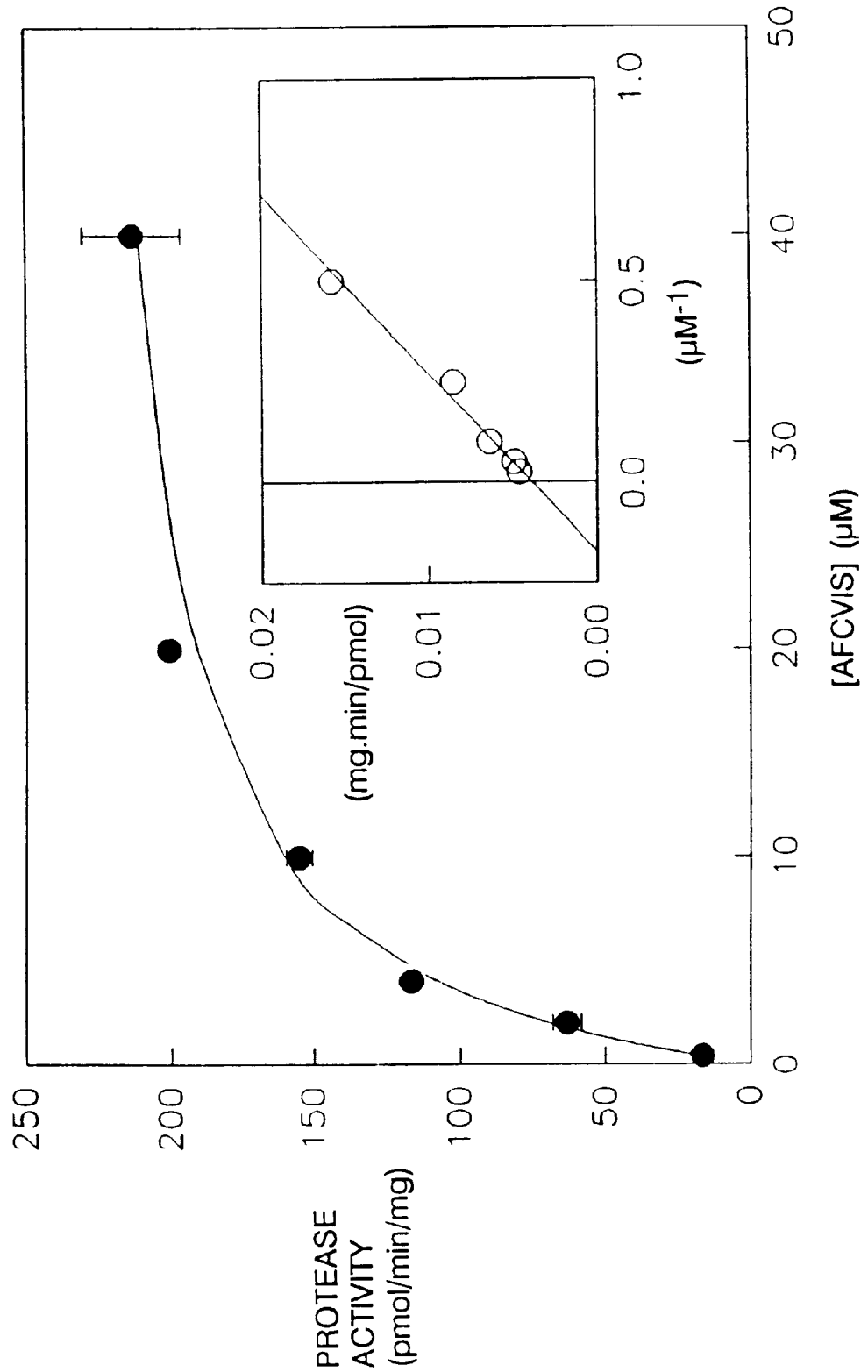
FIG. 2 is a pair of graphs illustrating the kinetics of the formation of N-[$^3$H]acetyl-S-all-trans-farnesyl-L-cysteine (N-[$^3$H]-AFC) as a function of N-[$^3$H]-acetyl-S-farnesyl-L-cys-L-val-L-ile-L-ser (AFCVIS) or N-[$^3$H]acetyl-S-farnesyl-(SEQ ID NO: 1) concentration. Protease activity (pmol/min/mg) is plotted as a function of AFCVIS concentration ($\mu$M) in panel A. Panel B is an Eadie-Hofstee plot of the same data. Symbols represent mean values of two determinations and error bars represent the standard deviation from the mean. Error bars not shown are within symbols.

Briefly, N-[$^3$H]-Acetyl-S-farnesyl-L-cys-L-val-L-ile-L-ser or N-[$^3$H]acetyl-S-farnesyl-(SEQ ID NO: 1) at a concentration of 10 μM was incubated with bovine liver microsomal membranes (preparation described below). Periodically, 50 μL aliquots were withdrawn from the incubation mixture and the reaction was quenched with 500 μL of chloroform/methanol (1:1, v/v). N-[$^3$H]-AFC was extracted after thoroughly mixing the mixture for 1 minute and extracting with chloroform. Phase separation was achieved by adding 500 μL of 1M citric acid. The chloroform layer was evaporated under nitrogen, resuspended in hexane/isopropanol/TFA (85:15:0.1), and authentic AFC standard was added for detection at 210 nm. The sample was injected on a silica HPLC column (Dynamax 60A, Rainin, Woburn, Mass.) and eluted with the same solvent. Radioactivity was counted with an on-line Berthold (Nashua, N.H.) LB 506-C HPLC radioactivity monitor. The results are presented in FIG. 1. When the concentration of substrate 1 was varied, saturation was observed, and the $K_M$ and $V_{max}$ were measured to be 4.8±0.6 μM and 0.236±0.008 nmol/min/mg protein respectively (FIG. 2).

AFC formation did not occur when the tetrapeptide was D-AFC-val-ile-ser (synthesis described below) 2, nor when the carboxyl group of the serine residue was methylated. These data demonstrate that the proteolysis is stereospecific, and that a free carboxyl terminal group is required in the substrate.

Figure 3:
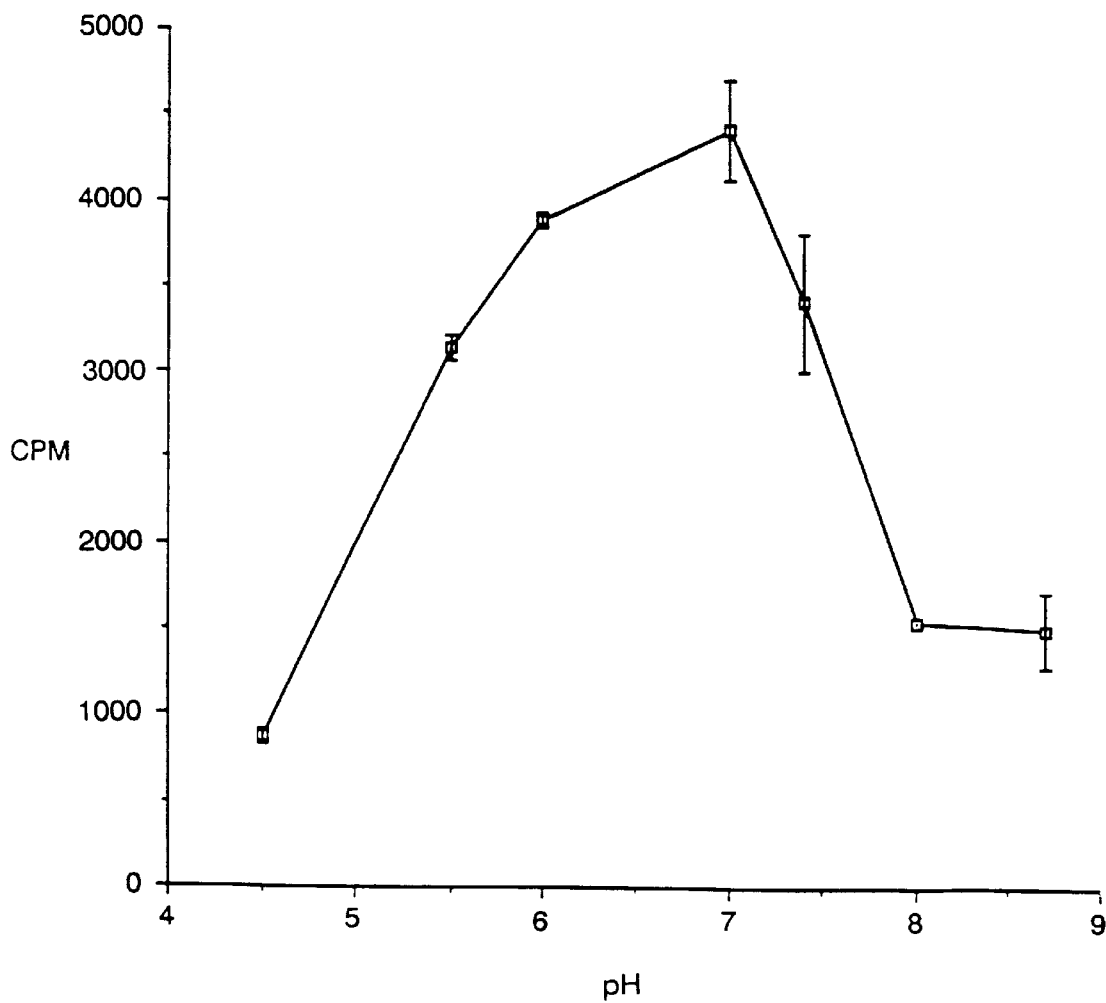
FIG. 3 is a graph depicting the dependence of protease activity on pH. Symbols represent mean values of two determinations and error bars represent the standard deviation from the mean. Error bars not shown are within symbols.
Figure 4:
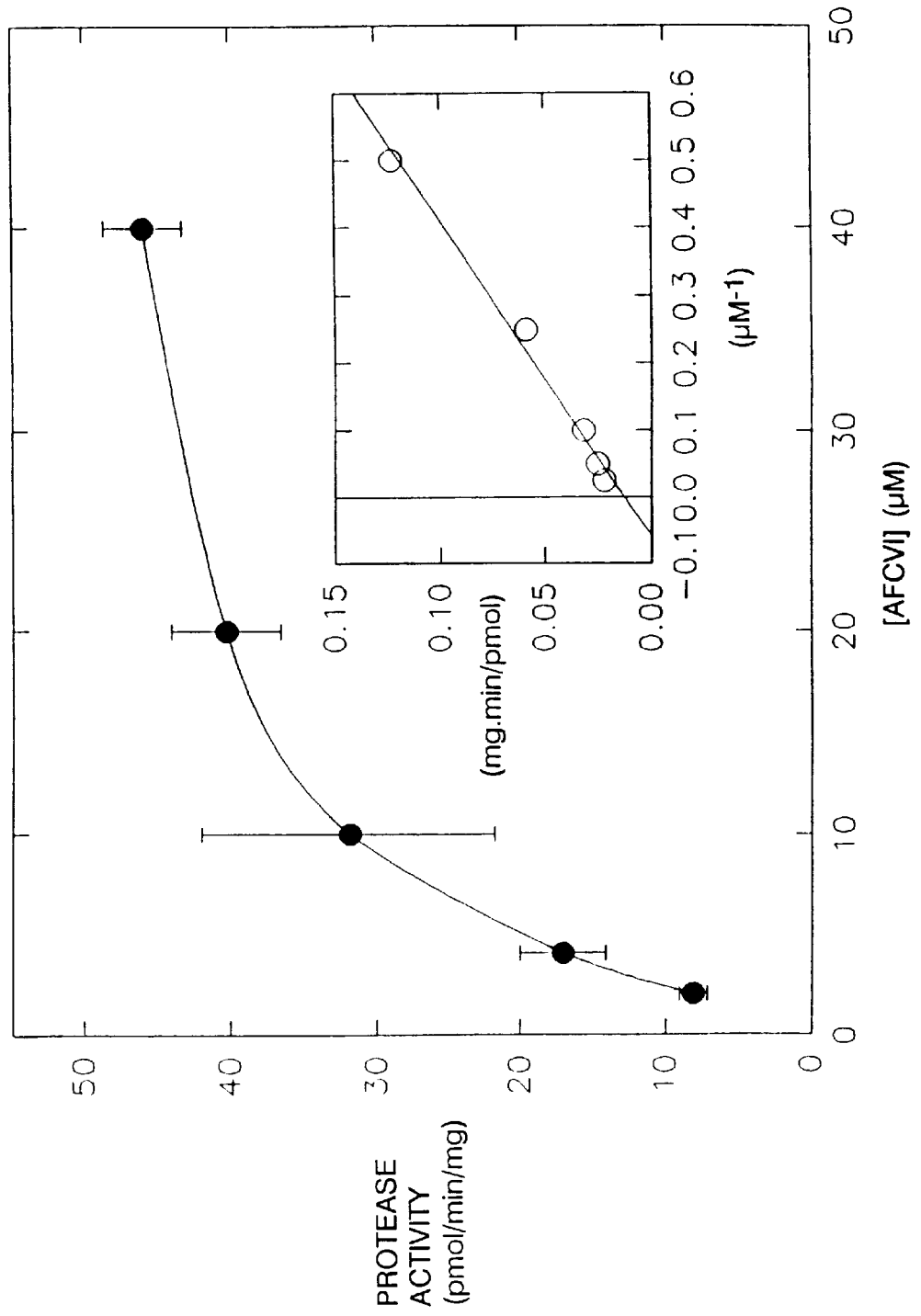
FIG. 4 is a pair of graphs illustrating the kinetics of the formation of N-[$^3$H]-AFC as a function of N-[$^3$H]-Ac-S-farnesyl-L-cys-L-val-L-ile (AFCVI) concentration. Protease activity (pmol/min/mg) is plotted as a function of AFCVI concentration ($\mu$M) in panel A. Panel B is an Eadie-Hofstee plot of the same data. Symbols represent mean values of two determinations and error bars represent the standard deviation from the mean. Error bars not shown are within symbols.

A pH versus rate profile for the proteolysis reaction showed a broad maximum at approximately pH 7. Briefly, the protease activity was determined with 4 μM N-[$^3$H]-Acetyl-S-farnesyl-L-cys-L-val-L-ile-L-ser or N-[$^3$H]acetyl-S-farnesyl-(SEQ ID NO: 1) as substrate in the following buffers: sodium acetate (pH 4.5 and 5.5), sodium phosphate (pH 6.0 and 7.0), Hepes (pH 7.4), and Tris (pH 8.0 and 8.7). Incubation time was 30 minutes. The results of this analysis are presented in FIG. 3.

A similar stereospecific proteolytic enzymatic activity was also found in dog pancreatic microsomes. Under extended incubation conditions, where 54% of the tetrapeptide substrate 1 was cleaved by these microsomes, no proteolysis of D-AFC-val-ile-ser 2 could be detected (<1%). Dog pancreas microsomes have already been shown to process farnesylated but unproteolyzed ras protein into the mature protein containing the carboxyl terminal farnesylated cysteine residue (Hancock et al. *EMBO J.* 10:641, 1991).

Characterization of Membrane-Bound Isoprenylated Protein Endoprotease

The membrane isoprenylated endoprotease activity from bovine microsomal membranes (Ma & Rando, 1992) is successfully solubilized in the detergent CHAPSO and partially purified. The partially purified enzyme is characterized by using both reversible and irreversible inhibitors as well as enzyme kinetic analysis and chromatographic properties. Sensitivity to inhibitors suggests that the enzyme is a cysteine protease. From the characterization of the solubilized enzyme, it appears that some of the classic protease affinity labeling agents—halomethyl ketones—selectively and irreversibly inhibited the endoprotease (Chen, 1995).

For example, Nα-tosly-L-phe-nylalanine chloromethyl ketone (TPCK), a classic irreversible inhibitor for serine proteases (e.g., α-chymotrypsin) (Schoellmann & Shaw, 1963; Powers, 1977, Prorok et al., 1994) and cysteine proteases (e.g., papain) (Bender & Brubacker, 1966; Whitaker & Perez-Villasenor, 1968; Drenth et al., 1976; Shaw, 1990), irreversibly inhibits the endoprotease with a second-order rate constant $K_{inh}/K_1$=77±6 M$^{-1}$ min$^{-1}$, while Nα-tosyl-L-lysine chloromethyl ketone (TLCK), an inhibitor for trypsin and trypsin-like enzymes, does not inhibit the enzyme activity under the same conditions. Furthermore, a new chloroketone containing a farnesyl moiety (BFCCMK) was prepared and shown to be a much more potent inactivator of the endoprotease than TPCK is. These haloketone derivatives are the first specific irreversible inhibitors known for the endoprotease. Analogs of this type are useful both for the molecular identification of the endoprotease and for studies designed to uncover the functional role(s) of the endoprotease.

Preparation and Solubilization of the Membrane-Bound Endoprotease

Bovine liver microsomal membranes were prepared according to the method of Walter and Blobel (1983). A typical adapted procedure was briefly as follows: the frozen bovine liver (100 g) was thawed and minced into small pieces which were placed in the chamber of a Waring blender (model 5010s). Three volumes of cold buffer A were added to the liver, and the liver was blended for 1 min. three times. The supernatant was transferred to eight centrifugation tubes (each 45 mL) and centrifuged for 10 min. at 1000 g (Beckman JA-20 rotor). Floating fatty materials were removed, and the rest of the supernatant was further centrifuged at 1000 g for 10 min. The supernatant (7 mL in each tube) was collected and mixed with 1 mL of 2.0 M sucrose in each tube. The mixture was centrifuged at 113000 g for 2.5 hrs. (Beckman Ti 50 rotor). The supernatant of 113000 g was discarded, and the pellets were rinsed with buffer B (2×2 mL in each tube). The pellets were then suspended in buffer C (70 mL) and homogenized three strokes with a Talboys electrical homogenizer which consists of a Tline Laboratory Stirrer, Model 101, a shaft with a Teflon Pestle, and a glass tube (Talboys Engineering Corp., Emerson, N.J.). The homogenized microsomal membranes were centrifuged at 113000 g for 1 hr. (Beckman Ti 50 rotor). The pellets were suspended in 20 mL of buffer C and homogenized three strokes with an electric homogenizer. The homogenized bovine liver microsomal membranes were stored at −80° C. The membrane preparation was incubated in 20 mM Tris-HCl (pH 7.0), 1 mM EDTA, 0.1 mM PMSF, 1 mM DTT, and 1% CHAPSO at 4° C. for 1 hour. The mixture was centrifuged at 4° C. for 2.5 hours at 11300 g (Beckman Ti 50 rotor) or for 45 minutes at 304000 g (Beckman TLA-100.3 rotor). The clear supernatant was carefully collected; ca 40% of membrane proteins were solubilized (e.g., for a typical run, 16 mg of solubilized proteins were obtained form 44 mg of membranes.

Partial Purification of the Isoprenylated Protein Endoprotease

All purification steps were carried out at 4° C.

Ion Exchange Chromatography

The solubilized protein preparation (16 mg) was chromatographed on a Resource Q column (6 mL) (Pharmacia)

using an FPLC system (Pharmacia LKB Biotechnology). The chromatography was performed as described in the legend of FIG. 13A. Fractions between 0.4 and 0.5 M NaCl contained the majority of the isoprenylated protein endoprotease activity. These fractions (63–69) were pooled; the pool was concentrated by an Amicon CentriPrep-10 concentrator; the final concentrate (2.2 mg) was stored at −80° C.

Superose 12 Column

The concentrate (2.2 mg) from the Resource Q column was applied to a Superose 12 column (124 mL) equilibrated with 20 mM Tris-HCl (pH 7.0) containing 1 mM EDTA, 100 mM NaCl, and 0.1% CHAPSO. The endoprotease activity was eluted as described in the legend of FIG. 13B.

Protease Activity Assay

The solubilized endoprotease activity was assayed, adapting from the published method for assay of the activity in membrane preparations (Ma & Rando, 1992). AN aliquot (1.0 μL) of the solubilized protein preparation was diluted in 47 μL of buffer D (See materials) at 4° C. Radioactive tetrapeptide substrate [$^3$H]AFCVIM (N-[$^3$H]acetyl-S-farnesyl-L-cysteinyl-L-valyl-L-isoleucyl-L-methionine or N-[$^3$H]acetyl-S-farnesyl-(SEQ ID NO: 2) of specific activity 2.2 Ci/mmol) in DMSO (2 μL) was added at time zero (final concentration was 2 μM for most assays). After the reaction mix was vortexed well, it was incubated at 37° C. for 30 minutes. The reaction was quenched with 0:5 mL of chloroform/methanol (1/1, v/v) and 0.5 mL of 1 M citric acid. After mixing thoroughly for 2 minutes, the organic layer was separated and evaporated by nitrogen steam. The residue starting substrate and enzymatic product (N-[$^3$H]acetyl-S-farnesycysteine, [$^3$H]-AFC) was analyzed on a normal phase HPLC column (Dynamaz 60A, Rainin) with hexane/isopropyl alcohol/TFA (92/8/0.0001, by volume) and a Berthold LB 506-C HPLC radioactivity monitor.

Figure 15:
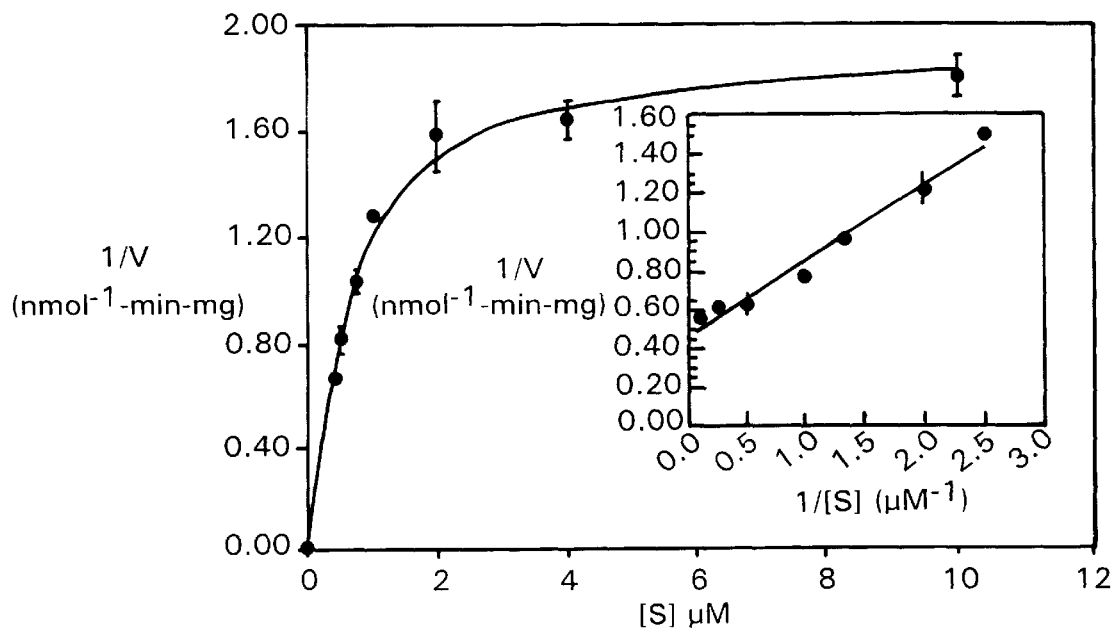
FIG. 15. is a substrate saturation chruve for the enzyme.

Determination of $K_m$ and $V_{max}$ $K_m$ and $V_{max}$ values for [$^3$H]AFCVIM (SEQ ID NO: 2) in the presence of 425 ng of the partially purified protein preparation in 50 μL of reaction solution were obtained by fitting the saturation experimental data points to the Michaelis-Menten equation (Lineweaver-Burke plots gave essentially the same $K_m$ and $V_{max}$ values) (FIG. 15).

Polyacrylamide Gel Electrophoresis

SDS-PAGE was performed using a Hoefer minigel SE-250 or standard gel apparatus and discontinuous 10% analytical gels, prepare according to the method of Laemmli (1970). Protein bands were detected by either Coomassie Blue or silver stain.

Protein Concentration Determination

Protein concentrations were determined by the modified Lowry Assay (Lowry et al., 1951) using the Bio-Rad DC Protein Assay kit.

Inhibition of the Isopreylated Protein Endoprotease by Halomethyl Ketones

A typical procedure of inhibition is given here to illustrate the details of this procedure. A CHAPSO-solubilized protein preparation (2.5 mg/mL) or a partially buffered protein preparation (0.17 mg/mL) was incubated with chloromethyl ketone inhibitors at 37° C. for 30 minutes. Aliquots were removed at timed intervals and diluted with assay buffer E for the solubilized preparation of with assay buffer D for the partially purified protein preparation in 20-fold. The final protein and substrate concentrations were 0.12 mg/mL (or 8.5 μg of partially purified protein preparation per milliliter) and 2.0 μM, respectively, except as otherwise noted; the residual enzyme activity was assayed as described above. TPCK and BFC-CMK were characterized by kinetic measurements. The bimolecular rate constant $K_{inh}/K_1$ and pseudo-first-order kinetic rate constant $K_{inh}$ were obtained using the Kitz-Wilson method (Kitz & Wilson, 1962). According to Kitz-Wilson method, the irreversible modification of an enzyme by an active-site directed inhibitor is given by

(I)

where $K_1=[E]\cdot[I]/[E\cdot I]$ and $-d([E]+[E\cdot I])/dt=K_{inh}[E\cdot I]$. [I] and [E] are inhibitor and enzyme concentrations at a certain time, respectively. Under conditions here $[I]>>[E_o]$, which is the enzyme concentration at time zero, [I] is constant. Under conditions where the enzyme-inhibitor solution is extensively diluted before the assay, a simplified equation 2 can be obtained as follows:

$$\ln [E]/[E_o] = -K_{app} t \tag{2}$$

Where $[E]/[E_o]$ is remaining enzyme activity (%) (REA %) after the enzyme is preincubated for time "t" under the conditions and where $K_{app}=K_{inh}/(1+K_1/[I])$. Equation 2 shows that the remaining enzyme activity (%) vs time in the irreversible inhibition reaction is governed by first order kinetics.

From equation 2, $$1/K_{app}=1/K_{inh}+K_1/K_{inh}[I] \tag{3}$$

If [I] is close to $K_1$, a plot in accordance with equation 3 should be a straight line that intercepts the positive y-axis. The interception is equal to $1/K_{inh}$; the slope of the line is equal to $K_1/K_{inh}$.

Solubilization of the Endoprotease Activity

Initial experiments were aimed at determining whether the protease behaved as an integral membrane protein or as a protein weakly associated with the membrane. Homogenized bovine microsomal membranes stored at −80° C. were thawed at 4° C. and mixed with 20 mM Tris-CCL buffer at pH 7.0. The mixture was homogenized manually and incubated at 4° C. for 45 minutes. The incubated membranes at 4° C. were centrifuged at 304000 g for 45 minutes. Both pellets and supernatant were assayed for the endoprotease activity. As expected, it was found that the main enzymatic activity remained in the membrane pellets (Ma & Rando, 1992); no appreciable activity was released to supernatant (Table I). In addition, both of the chaotropic agent sodium bromide (0.5 M) in the above buffer containing 0.05% Tween-20 and the strong denaturing agent urea (4 M) in the above buffer were used separately to extract the membranes. After the supernatant from 0.5 M nABr and 4 M urea treatments were dialyzed against buffer D. No appreciable proteolytic activity was found in either of the supernatant (Table I). These findings are consistent with the notion that the endoprotease from bovine microsomal membranes is an integral membrane protein.

Figure 11A:
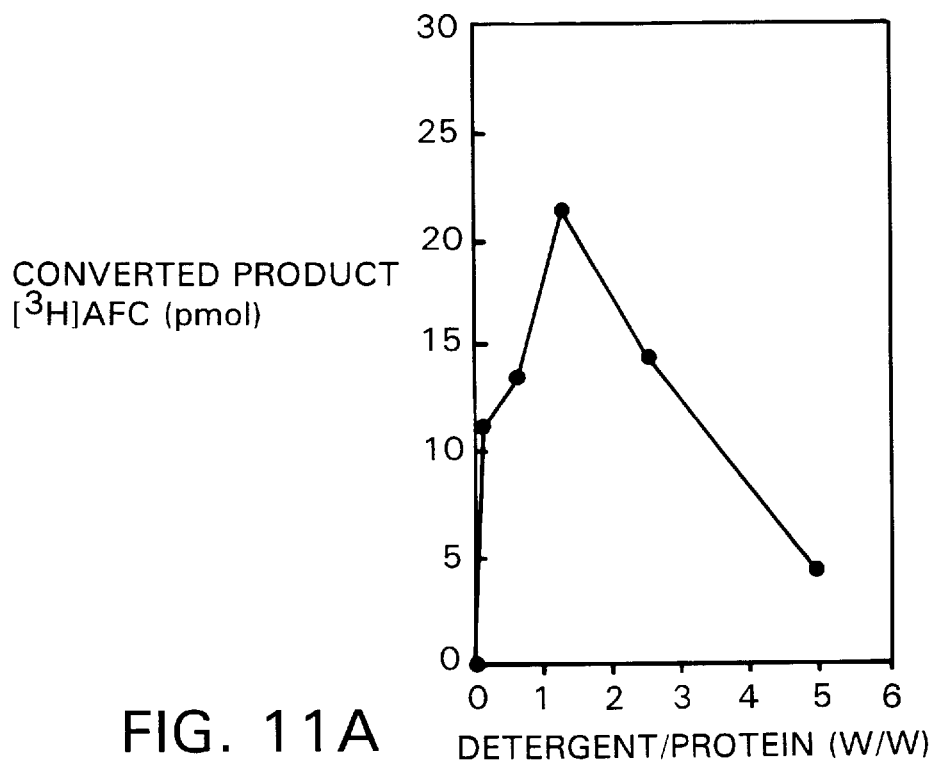
FIGS. 11A and 11B illustrate CHAPSO solubilization of the enzyme and the effect of CHAPSO concentration on the enzyme.
Figure 11B:
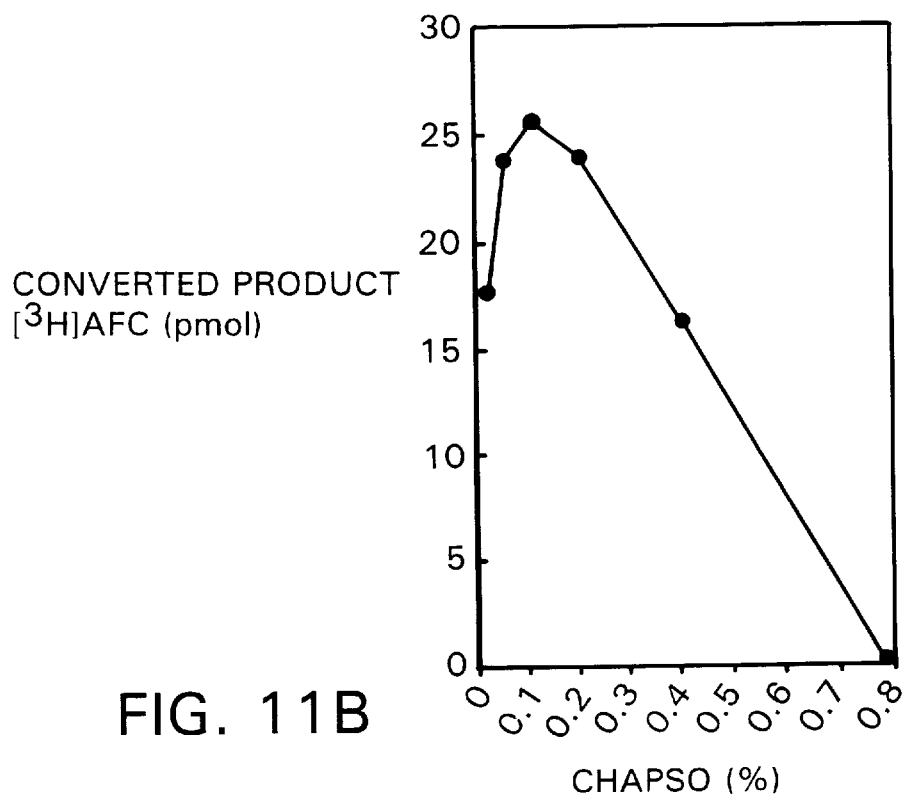

Initial studies on a variety of detergents showed that the endoprotease activity was extensively solubilized from bovine microsomal membranes by octyl glucoside, Triton X-100, CHAPS, CHAPSO. sodium cholate, and by CTAB. CHAPSO effectively released 77% of the endoprotease activity from membranes at its optimum conditions (vide infra). Moreover, CHAPSO has a high CMC value (8 mM at 0–0.05 M Na$^+$) (Hjelmeland et al., 1983) and does not interfere with the monitoring of columns at 280 nm. FIG. 11A shows that the ratio of detergent to protein (w/w) is critical for efficient solubilization; the optimum ratio for 8.1 mg of protein/mL was 1.2/1 (16 mM CHAPSO). The solubilized endoprotease is stable in a broad range of detergent concentrations. The endoprotease activity was maximal at 0.1% CHAPSO in 20 mM Tris-HCl buffer at pH 7.0 with 1 mM EDTA (FIG. 11B). At this concentration, the enzyme activity remained in supernatant after it was centrifuged for 11300 g for 1 hour.

Figure 12:
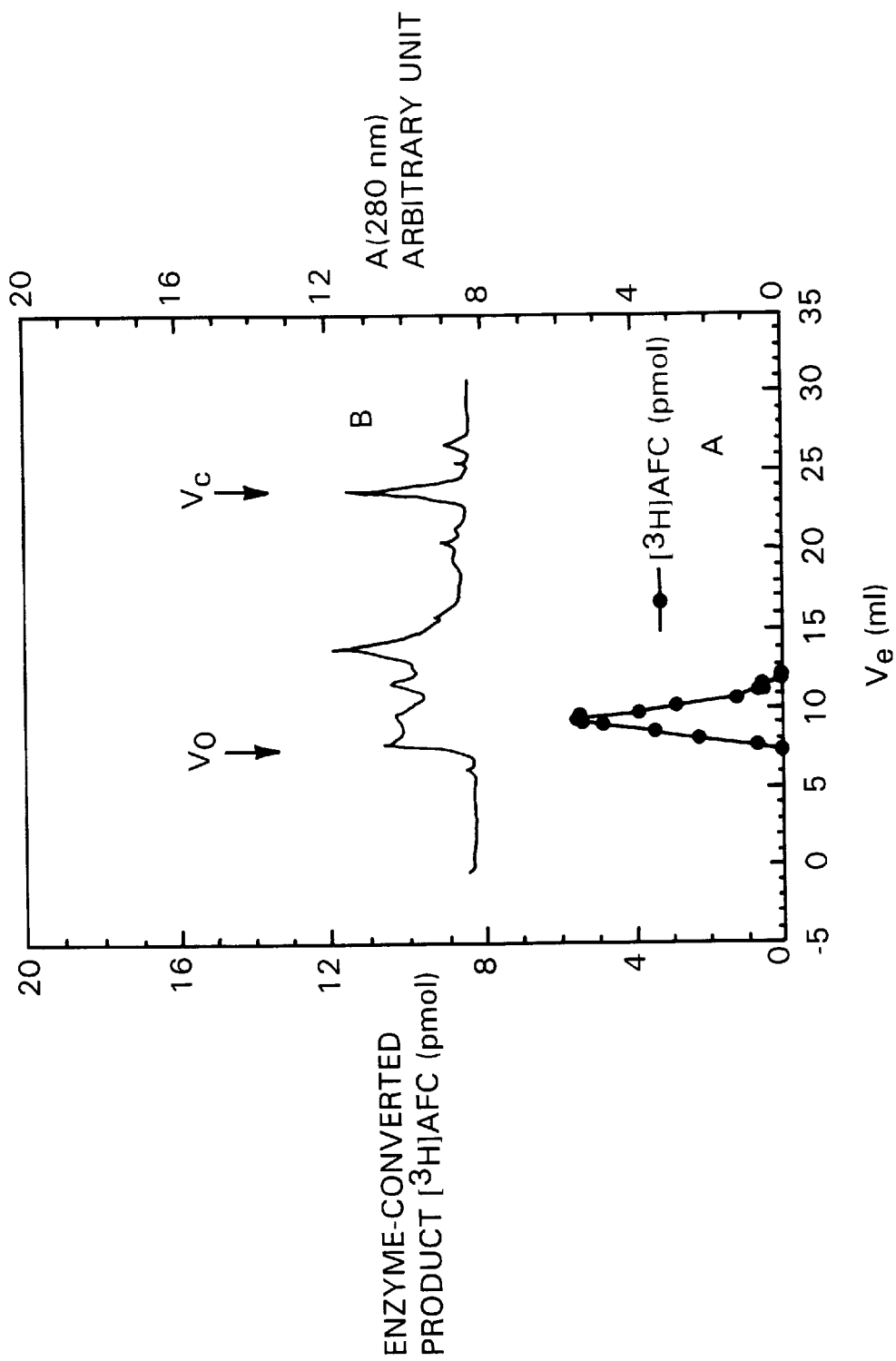
FIG. 12 illustrates gel filtration chromatography of the enzyme.

These properties of CHAPSO make it ideal, among the detergents tested, for the solubilization of the endoprotease. Three conventional criteria were used to demonstrate that enzyme was successfully solubilized by CHAPSO: (i) the endoprotease activity was maintained in the supernatant after centrifugation both at 304000 g for 45 minutes and at 113000 g for 2.5 hours; (ii) the CHAPSO-solubilized enzyme activity passed through a Millex GV 0.22 $\mu$m filter (Millipore) with ~100% recovery; (iii) after chromatography of the supernatant on a Sephadex 200 HR 10/30 column, the endoprotease activity was detected between the void volume and the column volume (FIG. 12). It should be noted that a second small amount of proteolytic activity was also found with an apparent molecular mass of approximately 60 kDa, which amounted to approximately 10% of the major peak, but which chromatographed at a smaller molecular size than the major peak. This smaller peak was not investigate further, for several reasons. Quantitatively, it is not significant. The activity is potently inhibited by 1,10-$\phi$, a metal chelator without effect on the primary peak of activity and without effect on the previously described mammalian (Ma & Rando, 1992) and yeast endoproteolytic activity (Ashby et al., 1992). It also is no known if the smaller peak of activity i s comprised of an endoproteolytic activity or is simply made up of nonspecific proteases. Finally, the major peak of activity is profoundly inhibited by the reduced peptide inhibitor RPI (Ma et al., 1993), which also blocks ras processing in vivo. All further studies described here will be relevant to the major solubilized peak of activity.

Partial Purification of the Isoprenylated Protein Endoprotease

Chromatography of the Endoprotease by Ion Exchange Chromatography

Figure 13A:
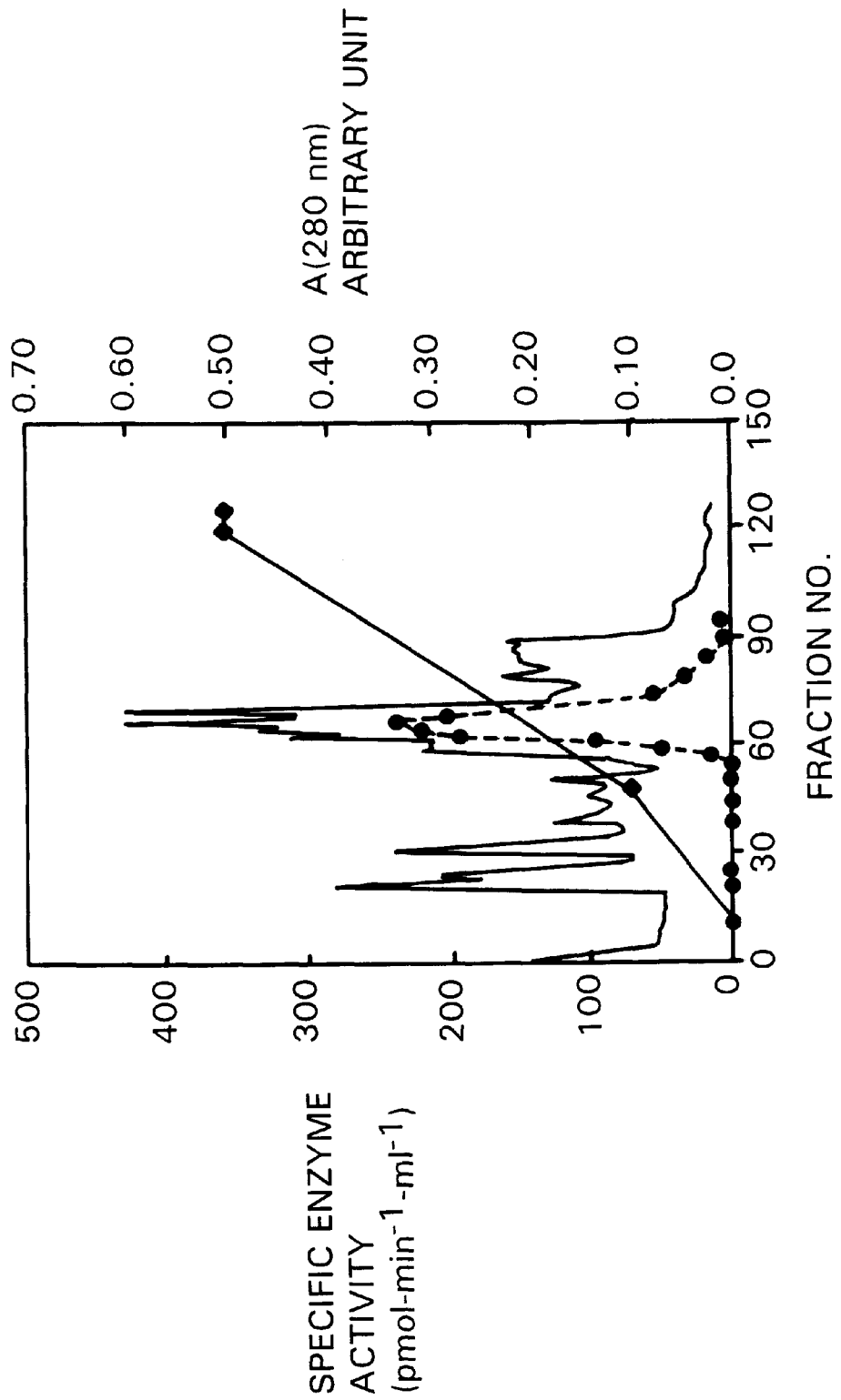
FIGS. 13A and 13B illustrate column chromatography of the enzyme.

Solubilized microsomal membrane protein (16 mg) was chromatographed on a Resource Q anion exchange column (6 mL). FIG. 13A shows the elution profile of the isoprenylated protein endoprotease activity from the column. The activity of fractions was assayed in the presence of buffer E. The activity appeared as a single sharp peak that was eluted at approximately 0.4 M sodium chloride. The peak fractions from the Resource Q column were pooled and concentrated for gel filtration chromatography (vida infra).

Chromatography of the Endoprotease on a Gel Filtration Column

Figure 13B:
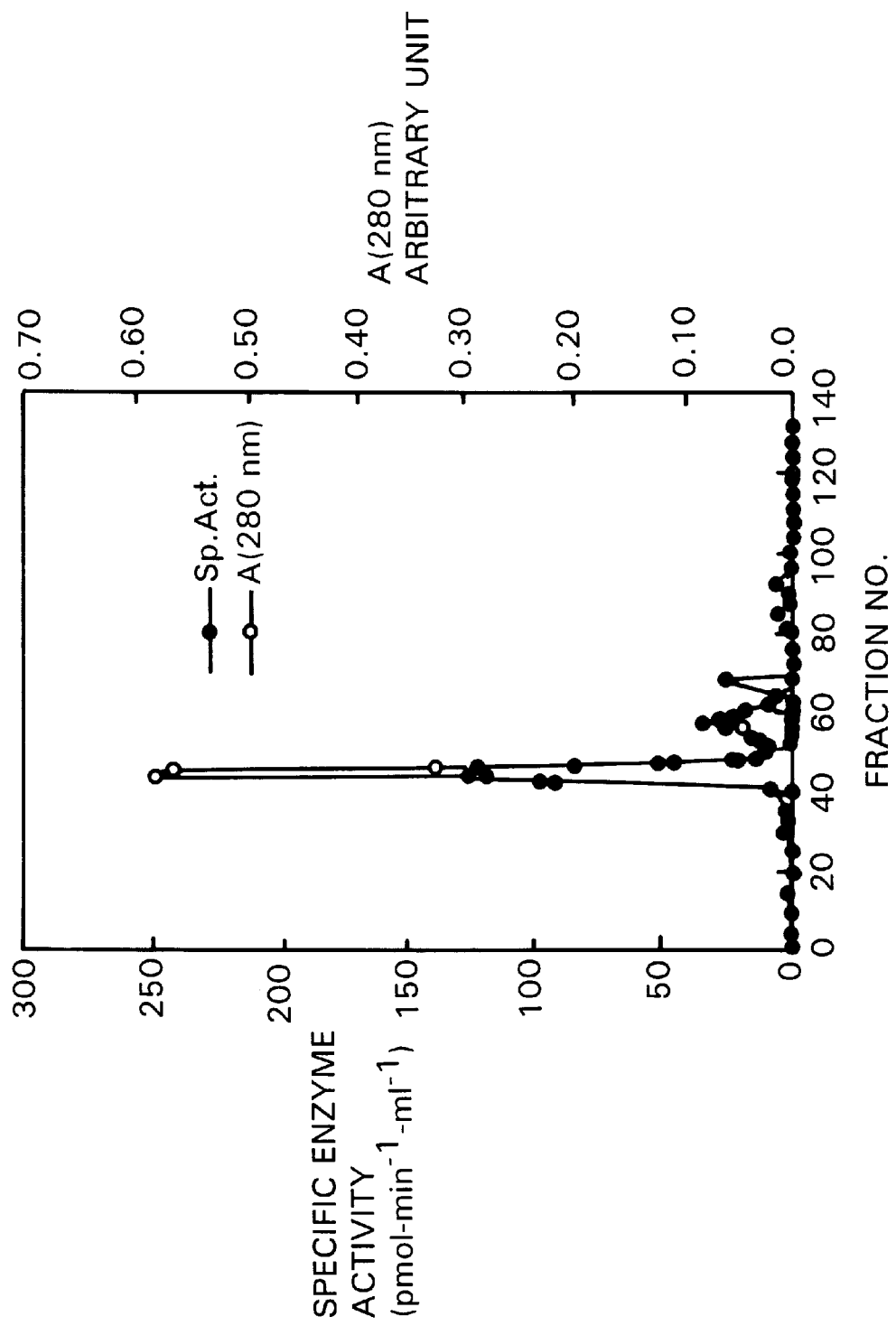

The pool from the Resource Q column was chromatographed on a Superose 12 column (124 mL). FIG. 13B shows the elution profile of the endoprotease activity from the gel filtration column. The activity was eluted at the high molecular weight end, and no low molecular weight activity was observed (vide supra). The peak fractions were pooled and saved at –80° C. for later use.

Table II summarizes the results of a typical purification procedure that started with 44 mg of bovine liver microsomal membrane proteins. After detergent extraction, Resource Q chromatography, and Superose 12 gel filtration chromatography, the endoprotease was partially purified to 9-fold activity with a yield of approximately 10%. The final specific activity was 1.8 nmol of [$^3$H]AFC per min per milligram of protein (in the presence of 10 $\mu$M of [$^3$H]-AFCVIM (SEQ ID NO: 2) tetrapeptide substrate).

Figure 14:
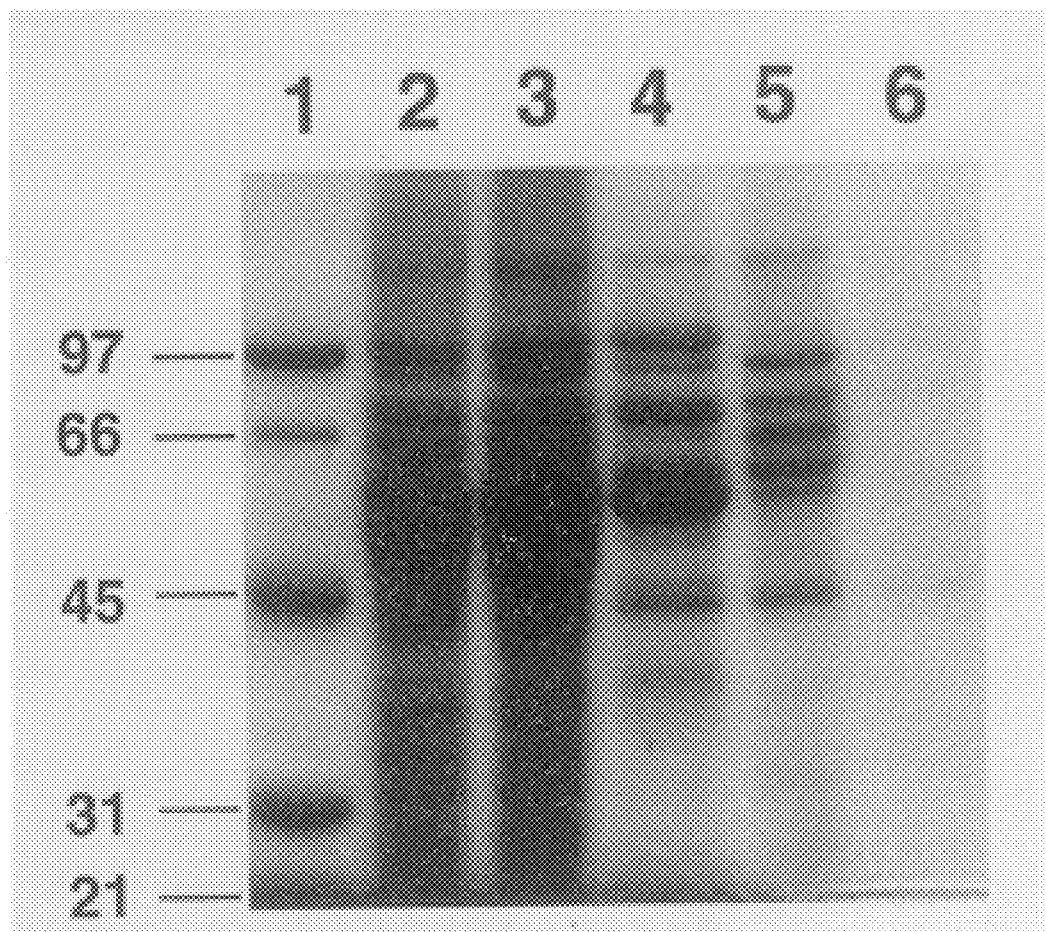
FIG. 14 illustrates partial purification of the enzyme on a gel.

The low recovery of activity reported above, coupled with relatively modest purification of the endoprotease, suggests that the enzyme becomes relatively unstable as it is purified. Several other column materials were tested for further purification, with very modest results. Column studies included Thiopropyl Sepharose 4B, Zn$^{2+}$-charged chelating column, DEAE, and hydrophobic interaction columns. Among the tested hydrophobic columns, a Butyl Agarose column was the best; it produced 2.0-fold purifications with 63% recovery of activity. None of these purification efforts produced a more highly purified enzyme than the scheme shown in Table II. Attempts at enzyme purification by affinity chromatography using reduced peptide inhibitors (Ma et al., 1993) met with no success. Purified enzyme could not be eluted from the column, under a variety of conditions (A. Chaudhuri, unpublished experiments). Another procedure, which led to about the same level of purification as shown in Table II, utilized Thiopropyl Sepharose 4B, DEAE, and Mono Q columns. This procedure produced a 7-fold purification. FIG. 14 shows SDS-PAGE gel analysis of the protein bands from this purification procedure. Only a few protein bands in this gel were visualized by Coomassie Blue after this purification procedure (FIG. 14). By comparison of SDS-PAGE analysis from the product of the last step of purification in Table II with FIG. 14, the two preparations gave different band patterns. Two more column steps from the purification scheme in FIG. 14 did not proved a greater purification than the procedures used in Table II in terms of specific activity although the product from the purification scheme shown in FIG. 14 was less complex with respect to the numbers of protein bands on the SDS-PAGE gel.

Kinetic Experiments

The partially endoprotease was used to determine the $V_{max}$ and $K_m$ values for the radioactive tetrapeptide substrate, [$^3$H]AFCVIM (SEQ ID NO: 2). FIG. 15 shows that the enzyme was saturated by the substrate. The experimental data points fit the Michaelis-Menten equation well, as described in Methods. $K_m$ and $V_{max}$ values for $^3$H]AFCVIM were measured to be 0.65±0.08 $\mu$M and 1.96±0.07 nmol/(min-mg of protein), respectively. The results are to be contrasted with results obtained with whole membranes (Ma et al., 1992).

Characteristics of the Solubilized Endoprotease Activities

The solubilized protein materials can be stored at –80° C. for a few months without significant loss of endiprotease activity. Neither DTT (1–5 mM) nor glycerol (20%) affects the enzyme's activity. A variety of inhibitors was tested on the CHAPSO-solubilized preparations and on the partially purified enzyme from the purification scheme shown in Table II (Table III). The membrane-bound enzyme proved to be relatively insensitive to a wide spectrum of protease inhibitors (Ma et al., 1993). However, after the endoprotease was solubilized, it became more sensitive to some of the inhibitors. A typical example is p-chloromercuribenzoate (PCMB), which inhibited the endoprotease 41% at 0.5 mM, when membrane-bound (Ma et al., 993). The solubilized enzyme is completely inactivated by 100 μM PCMB (Table III). DTT (5 mM) was able to regenerate 44% of the inhibited enzyme activity from the detergent extract after it was inhibited completely by 0.5 mM PCMB (Table III), while no regeneration of the inhibited activity was observed after extensive dialysis and dilution. It appeared that the purer the enzyme, the greater the sensitivity to PCMB. The partially purified enzyme activity was inhibited to 67% by 5 μM PCMB (Table III). The partially purified enzyme was however, not inhibited by chymostatin (0.33 mM), 1,10-φ (1 mM), or DTT (5 mM) (Table III). These latter results are interesting because they serve to differentiate clearly between the microsomal enzyme described here and the putative soluble endoprotease from extracted pig brain which is sensitive to these inhibitors (Akopyan, 1994).

Synthesis of N-[$^3$H]-acetyl-S-all-trans-farnesyl-L-Cys-L-Val-L-Ile-L-uSer or N-[$^3$H]acetyl-S-farnesyl-(SEQ ID NO: 1)

A solution of N-[$^3$H]-acetyl-S-all-trans-farnesyl-L-Cys-L-Val-L-Ile (1.12 μmol, 250 mCi/mmol), L-serine hydrochloride methyl ester (20 mg, 0.13 mmol), and 1-hydroxybenzotriazole hydrate (17.4 mg, 0.13 mmol) in 3 mL of DMF was cooled to 0° C. 1-(3-Dimethylamino)propyl-3-ethyl carbodiimide hydrochloride (17.2 mg, 0.09 mmol) and N-methylmorpholine (14.1 μL, 13 mg, 0.13 mmol) were added at 0° C. The mixture was stirred at 0° C. under argon for 2 hours and at room temperature for 24 hours. Water (20 mL) was added and the mixture was extracted with ethyl acetate (4×20 mL). The combined organic layer was washed with 10% HCl, saturated sodium bicarbonate, and water, dried over anhydrous magnesium sulfate, filtered, and evaporated. The residue was dissolved in 3 mL of acetonitrile and 3 mL of 10% aqueous sodium carbonate was added. The mixture was stirred at room temperature for 24 h. 10% HCl was added to adjust the pH to 2. The mixture was then extracted with ethyl acetate (3×20 mL), and the combined organic layer was washed with water, dried over anhydrous magnesium sulfate, filtered, and evaporated. Purification was carried out by HPLC on a Rainin silica 4.6×250-mm column at a flow rate of 1.5 mL/min, using hexane/isopropanol/TFA 85:15:0.1 as eluant. UV detection was at 210 nm. Recovery of radioactivity was 28.2 μCi, 1.13×10$^{-4}$ mmol. Retention time was 6.49 min. Data from $^1$H-NMR (500 MHz, DMSO-d$_6$) of the authentic non-radioactive peptide are as follows: δ 8.14 (1H, d, J=8 Hz), 7.97 (1H, d, J=7 Hz), 7.86 (1H, d, J=9 Hz), 7.76 (1H, d, J=8.5 Hz), 5.16 (1H, t, J=8.5 Hz), 5.05 (2H, m), 4.48 (1H, brdd, J=6.5, 14 Hz), 4.25 (1H, t, J=8 Hz), 4.20 (1H, brt, J=8 Hz), 4.10 (1H, brd, J=7 Hz), 3.66 (1H, dd, J=6, 11 Hz), 3.56 (1H, dd, J=4, 11 Hz), 3.08 (2H, m), 2.73 (1H, dd, J=5.5, 13.5 Hz), 2.52 (1H, dd, J=4, 11 Hz), 1.90–2.10 (8H, m), 1.84 (3H, s), 1.73 (2H, m), 1.62 (3H, s), 1.60 (3H, s), 1.54 (6H, s), 1.41 (1H, m), 1.30 (1H, m), 0.80 (12H, m).

Synthesis of N-[$^3$H]-acetyl-S-all-trans-farnesyl-D-Cys-L-Val-L-Ile-L-Ser or N-[$^3$H]acetyl-S-farnesyl-(SEQ ID NO: 1)

This isomer was prepared by the same method as described above, starting with N-[$^3$H]-acetyl-S-all-trans-farnesyl-D-Cys-L-Val-Ile. The D compound was purified by HPLC. The eluting solvent was hexane/isopropanol/TFA 88:12:0.1 using a Rainen silica column, 4.6×250 mm. Flow rate: 1.5 mL/min with UV detection at 210 nm. Under these conditions, the retention time was 10.7 min. Data from $^1$H-NMR (DMSO-d6, 500 MHz) of the authentic nonradioactive peptide are as follows: δ 8.32 (1H, d, J=8 Hz), 8.05 (1H, d, J=7.5 Hz), 7.99 (1H, d, J=10 Hz), 7.95 (1H, d, J=8 Hz), 5.13 (1H, t, J=7 Hz), 5.04 (2H, dt, J=2, 7 Hz), 4.59 (1H, dd, J=8, 12 Hz), 4.42 (1H, dd, J=4, 9 Hz), 4.24 (2H, m), 3.69 (1H, dd, J=6, 10.5 Hz), 3.60 (1H, dd, 5, 10.5 Hz), 3.17 (2H, t, J=6.5 Hz), 2.63 (1H, dd, J=8, 14 Hz), 2.54 (1H, dd, J=7, 14 Hz), 2.06–1.88 (10H, m), 1.81 (3H, s), 1.61 (6H, s), 1.53 (6H, s), 1.22 (1H, m), 1.09 (1H, m), 0.82 (12H, m).

Measurement of Proteolytic Activity

Bovine liver microsomes were prepared according to Walter et al. (*Meth. Enzym.* 96:84, 1983). Kinetic measurements were performed by incubating 0.2 mg/mL protein with peptide substrates in 200 mM HEPES buffer containing 100 mM NaCl and 5 mM MgCl$_2$ at pH 7.4, all in a final volume of 50 μL. The peptide substrates were added in DMSO to a final concentration of 4% (v/v) at 37°. The enzymatic reaction was quenched at the appropriate time by the addition of 0.5 mL of chloroform/methanol (1/1, v/v). Phase separation was achieved by adding 0.5 mL 1M citric acid. The chloroform layer was separated and evaporated under nitrogen and the residue was dissolved in n-hexane/2-propanol/TFA containing cold AFC. The formation of the product $^3$H-AFC was followed by HPLC analysis at 210 nm according to Perez-Sala et al. (*Proc. Nat'l Acad. Sci. USA* 88:3043, 1991). The samples were injected onto a normal phase HPLC column (Dynamax 60, Rainin, Woburn, Mass.) connected to a model LB 506-C on-line radioactivity monitor (Berthold, Nashua, N.H.). The column was eluted with n-hexane/2-propanol/TFA[85:15:0.1 (v/v/v)] at 1.5 mL/min.

Synthesis of N-[$^3$H]-acetyl-S-all-trans-farnesyl-L-cys-L-val-L-ile and N-[$^3$H]-acetyl-S-all-trans-farnesyl-D-cys-L-val-L-ile A mixture of S-all-trans-farnesyl-L-Cys-L-Val-L-Ile methyl ester (20 mg, 36 μmol), $^3$H-acetic anhydride (0.02 mmol, ≈10 mCi, 500 mCi/mmol), triethylamine (3.3 μL, 0.024 mmol), and a catalytic amount of 4,4-dimethylaminopyridine in 20 mL of methylene chloride was stirred at room temperature overnight. The mixture was filtered and the solvent was evaporated. The residue was separated by HPLC (Rainin silica, 250×4.6 mm, 1.5 mL/min, hexane/isopropanol (85:15), detection at 210 nm, retention time: 4.27 min, yield: 3.57 mCi, 14.28 μmol, 719.) Data from $^1$H-NMR (CDCl$_3$, 500 MHz) of the authentic non-radioactive peptide methyl ester: 6.87 (1H, d, J=8 Hz), 6.47 (1H, d, J=8 Hz), 6.41 (1H, d, J=7 Hz), 5.27 (1H, dt, J=1, 7.5 Hz), 5.09 (2H, dt, J=1.5, 6 Hz), 4.56 (2H, m), 4.27 (1H, dd, J=6, 8.5 Hz), 3.74 (3H, s), 3.23 (2H, dd, J=1.5, 8 Hz), 2.91 (1H, dd, J=6, 13.5 Hz), 2.77 (1H, dd, J=7.5, 13.5 Hz), 2.22 (1H, m), 2.03 (3H, s), 2.10–1.96 (8H, m), 1.89 (1H, m), 1.67 (6H, s), 1.58 (6H, s), 1.40 (1H, m), 1.18 (1H, m), 0.90 (12H, m).

N-[$^3$H]-acetyl-S-all-trans-farnesyl-L-Cys-L-Val-L-Ile methyl ester (1.19 mCi, 4.76 μmol, 250 mCi/mmol) was dissolved in 12 mL of methanol. KOH/MeOH (5%, 12 mL) was added at 0° C. and the mixture was stirred at 0° C. for 1 h and then at room temperature for 18 h. Basic hydrolysis under these conditions served to specifically racemize the chiral center at the cysteine residue. Acetic acid was added to pH 7. The methanol was evaporated and the residue was extracted with ethyl acetate twice. The combined organic phase was washed with 10% HCl, then with water, then dried over anhydrous sodium sulfate, filtered, and evaporated. Total activity: 1.04 mCi (87%). Purification was carried out by HPLC on Rainin silica 250×4.6 mm column at a flow rate of 1.5 mL/min, using hexane/isopropanol/TFA 92:8:0.01 as eluant. UV detection was at 210 nm. The retention time of the D-L-L isomer was 8.1 min and for the L-L-L isomer it was 10.2 min. Data from $^1$H-NMR (DMSO-$d_6$, 500 MHz) of the authentic non-radioactive peptides: N-Ac-S-all-trans-farnesyl-L-Cys-L-Val-L-Ile: δ 8.13 (1H, d, J=8.5 Hz), 7.91 (1H, d, J=8 Hz), 7.79 (1H, d, J=9 Hz), 5.14 (1H, t, J=8 Hz), 5.04 (2H, brs), 4.46 (1H, dd, J=6, 10 Hz), 4.25 (1H, dd, J=6, 9 Hz), 4.11 (1H, dd, J=6, 8 Hz), 3.12 (2H, d, J=7.5 Hz), 2.72 (1H, dd, J=6, 14 Hz), 2.52 (1H, dd, J=7.5. 14 Hz), 2.06–1.88 (9H, m), 1.83 (3H, s), 1.74 (1H, m), 1.61 (3H, s), 1.59 (3H, s), 1.53 (6H, s), 1.38 (1H, m), 1.17 (1H, m), 0.78–0.86 (9H, m). N-Ac-S-all-trans-farnesyl-D-Cys-L-Val-L-Ile: δ 8.09 (1H, d, J=8 Hz), 8.07 (1H, d, J=10 Hz), 7.95 (1H, d, J=8 Hz), 5.15 (1H, t, J=8 Hz), 5.04 (2H, t, J=6 Hz), 4.57 (1H, dd, J=6.5, 8 Hz), 4.28 (1H, dd, J=7, 9 Hz), 4.09 (1H, dd, J=6, 8 Hz), 3.16 (2H, dd, J=4, 8 Hz), 2.65 (1H, dd, J=6.5, 13.5 Hz), 2.51 (1H, dd, J=7.5, 13.5 Hz), 2.04–1.88 (9H, m), 1.81 (3H, s), 1.75 (1H, m), 1.61 (6H, s), 1.53 (6H, s), 1.40 (1H, m), 1.19 (1H, m), 0.78–0.88 (9H, m).

Specific Enzymatic Cleavage Occurs at the Modified Cysteine Residue

The data described above show that the tetrapeptide 1 is enzymatically processed by microsomal preparations to generate AFC. All studies described below were done with the calf liver microsomal preparation, since it could be obtained readily. It was of special interest to determine where the initial cleavage reaction took place. To accomplish this, the tetrapeptide 1 was synthesized with a tritiated serine residue at the carboxyl terminus (preparation described below). This tetrapeptide was subjected to proteolysis by the microsomal enzyme, and the products were treated with ophthalaldehyde and mercaptoethanol to generate the fluorescently tagged peptides (Trepman et al. Arch. Biochem. Biophys. 204:524, 1980).

These peptides could be separated easily on reverse-phase HPLC. This analysis demonstrated that the initial incubation produced virtually only the tripeptide Val-Ile-Ser. Further incubation with the enzyme caused further proteolysis of the tripeptide, to produce the dipeptide. The analysis demonstrated that the initial proteolytic cut is between the AFC moiety and the adjacent valine residue. Further processing of the tripeptide probably occurs by means on nonspecific proteases.

Farnesylated Di- and Tripeptide Substrates of the Protease

The experiments described above demonstrate that the protease is stereospecific at the scissile bond and also requires a free terminal carboxyl group in the tetrapeptide substrate. Substrate specificity was further explored using the tripeptide AFC-val-ile and the dipeptide AFC-val (synthesis described below). The measured $K_M$ and $V_{max}$ values for the tripeptide are 9.2±0.21 μM and 58±4.9 pmol/min/mg respectively. The tripeptide is a weaker substrate for the protease than the tetrapeptide. Kinetic constants were not obtained for the dipeptide AFC-val, but it is clearly a substrate for the protease as well. Stereospecificity is also observed with both the dipeptides and tripeptides, because substitution of D-AFC for L-AFC in these molecules led to the complete abolition of substrate activity. Finally, AFC amide is not a substrate for the enzyme, demonstrating that a second amino acid moiety is required, in addition to AFC, in the substrate.

As expected, the proteolysis of [$^3$H]-AFC-val-ile-ser or [$^3$H]-(SEQ ID NO: 1) was inhibited by the dipeptide substrate (AFC-val) and by the tripeptide substrate (AFC-val-ile). Incubation of 4 μM substrate along with either 20 μM of the dipeptide or tripeptide led to an approximately 50% diminution in substrate cleavage. Interestingly, deletion of the farnesyl moiety from the tetrapeptide substrate to yield AC-val-ile-ser (SEQ ID NO: 1) did not produce an inhibitor of the enzyme. Incubation of the tetrapeptide substrate with a 5-fold excess of AC-val-ile-ser did not interfere with the processing of the substrate. This result strongly suggests that the isoprenyl moiety is important in enabling the substrate to bind to the enzyme.

A Isoprenoid Moiety is Important for Substrate Activity

The importance of the isoprenoid Moiety was studied by testing whether the isoprenoid structure affects the ability of various tripeptides to serve as substrates.

For these experiments the substrates were dissolved in DMSO and incubated with calf liver microsomal membranes (0.2 mg of protein/mL) (Walter et al., supra) as described above. The amount of radioactive product was determined as described above. The reaction was quenched with 500 μL of CHCl$_3$/MeOH (1:1, v/v), and the radioactive N-terminal amino acid, i.e. N-[$^3$H]AFC, was extracted after thoroughly agitating this mixture. Phase separation was achieved by adding 500 μL of 1M citric acid. After the chloroform layer was evaporated under nitrogen the residue was resuspended in n-hexane/isopropanol/TFA (90:10:0.01) and non-radioactive AFC was added as a standard for UV detection (210 nm). The sample was injected on a normal-phase HPLC column (Dynamax 60A, Rainin), and elution was performed with the same solvent at flow rate 1.5 ml/min. Radioactivity was counted with an on-line Berthold (Nashua, N.H.) LB 506-C HPLC radioactivity monitor. The limit of efficiency of this assay was 3× the background counts/min (~150 cpm), which permits detection of products from substrates whose activities are 0.4% of the $V_{max}$ of AFC-Val-Ile-Ser (SEQ ID NO: 1) (1.13 pmol/min/mg). The retention times for AGC, AFC, and AGGC are 7.58, 7.26, and 7.00 min respectively, and for AGC-Val-Ile, AFC-Val-Ile, and AGGC-Val-Ile, they are 5.48, 6.54, and 5.08 min respectively.

Because the experiments described above demonstrate that acetyl-S-all-trans-farnesyl-L-Cys-Val-Ile (AFC-Val-Ile) can serve as a substrate for the protease, the all-trans-geranyl-geranyl derivative (AGGC-Val-Ile) and the all-trans-geranyl derivative (AGC-Val-Ile) were prepared and tested. Both analogs were good substrates for the protease.

The geranylgeranyl derivative was hydrolyzed with a $K_M$ was 14.6 μM and the Vmax was 19.35 pmol/min/mg respectively (Table 1). As expected, stereospecificity was observed with respect to the isoprenylated amino acid, because no measurable protease activity was observed with neither D-AGGC-Val-Ile or D-AGC-Val-Ile as a substate (Table 1).

The experiments described above demonstrate that the protease exhibits a broad substrate specificity profile with respect to isoprenoid side chains. To resolve is whether or not the isoprenoid side-chain is essential, the following non-isoprenylated were prepared and studied: the cysteine analog C-V-I and the t-butylthio derivative of C-V-I. Neither analog was measurably processed by cleavage between the cysteine and valine residues (Table 1). These experiments demonstrate than an isoprenoid moiety is important for activity.

Sterospecificity Requirements of Substrates

Various stereoisomers of AFC-Val-Ile were prepared and tested for their ability to serve as a substrate for the protease.

The L-D-L and L-L-D analogs did not have substrate activity (Table 1). The same specificity was observed for the AFC-val-ile-ser (SEQ ID NO: 1) series. Further, all analogs studied in the AFC-val-ile series in which there was more than one D amino acid (e.g. D-D-D, D-D-L, D-L-D and L-D-D) were inactive. The stereospecificity at the X position of -CAAX was explored using L-AFC-Val-Ile-D-Met (SEQ ID NO: 2) and L-AFC-Val-Ile-L-Met (SEQ ID NO: 2). As shown in Table 1, only the all L tetrapeptide proved to be a good substrate for the enzyme. However, the L-L-L-D derivative proved to be processed to some extent, although the minimal amount of product formed precluded kinetic analysis. These data taken together show that the protease is stereospecific with respect to the CAA moieties, and stereoselective with respect to X.

TABLE 1

| SUBSTRATE | ISOMER | $K_M$ ($\mu$M) | $V_{max}$ (pmol/min/mg) |
|---|---|---|---|
| AFC—Val—Ile (1) | L—L—L | 9.2 ± 0.2 | 57.7 ± 5 |
| AGGC—Val—Ile (2) | L—L—L | 4.01 ± 0.4 | 26.20 ± 0.97 |
|  | D—L—L |  | inactive* |
| AGC—Val—Ile (3) | L—L—L | 14.60 ± 2.14 | 19.35 ± 1.12 |
|  | D—L—L |  | inactive* |
| Cys—Val—Ile (4) | L—L—L |  | inactive* |
| t-butylthio-Cys—Val—Ile (5) | L—L—L |  | inactive* |
| AFC—Val—Ile (6) | D—L—L |  | inactive* |
| AFC—Val—Ile (7) | L—D—L |  | inactive* |
| AFC—Val—Ile (8) | L—L—D |  | inactive* |
| AFC—Val—Ile—Met (9) | L—L—L—L | 2.96 +/− 0.35 | 126.3 +/− 4.7 |
| AFC—Val—Ile—Met (10) | L—L—L—D |  | weakly active** |

Values given are average values of two determinations ±S.D. Compound 1 had $K_M$ and $V_{max}$ values of 12.6 $\mu$M and 65.6 pmol/min/mg. These values are slightly lower than those reported here. However, the former measurement was performed on a different microsome preparation from a different animal. The measurements reported in this table were all determined using the same enzyme preparation.

*Analogs referred to as inactive did not show detectable activity as substrate when used at concentration of 10 mM and prolonged incubation time (16 hours). The sensitivity of the assay used allows the detection of protease activities above 1.13 pmol/min/mg (0.4% of the activity seen with AFC-V-I-S (SEQ ID NO: 1). **Where marginal activity is noted, detectable activity is observed under prolonged incubation periods, but the activity is <5% that observed with AFC-V-I-S.

Synthesis of N-[$^3$H]-Acetyl-S-trans-geranyl-L-Cys-L-Val-L-Ile and N-[$^3$H]-Acetyl-S-trans-geranyl-D-Cys-L-Val-L-Ile A mixture of S-trans-geranyl-L-cys-L-val-L-ile methyl ester (20 mg, 41 $\mu$mol), [$^3$H]-acetic anhydride (6 $\mu$mol, 3 mCi, 500 mCi/mmol), and a catalytic amount of 4,4-dimethylaminopyridine in 6 mL of methylene chloride was stirred at room temperature overnight. The mixture was filtered and the solvent was evaporated. The residue was purified by HPLC (Rainin silica, 250×4.6 $\mu$m, 1.5 mL/min, hexane/isopropanol 85:15, uv detection was at 210 nm). Retention time: 4.13 min. Yield: 1.079 mCi, 4.32 $\mu$mol, 72%.

$^1$HNMR (CDCl$_3$,500 MHz) of the authentic non-radioactive peptide methyl ester: 6.88 (1H,d,J=8 Hz), 6.50 (1H,d,J=9 Hz), 6.43(1H, d, J=7.5 Hz), 5.26(1H,t, J=7 Hz), 5.06(1H,t,J=7 Hz), 4.56(2H,m), 4.28(1H,dd,J=6.5,8.5 Hz), 3.72(3H,s), 3.23 (2H,dd,J=2,8 Hz), 2.91(1H,dd,J=5,13.5 Hz), 2.77(1H,dd,J=8,13.5 Hz), 2.21(1H,m), 2.04(3H,s), 2.08–2.02(4H,m), 1.90(1H,m), 1.68(3H,s), 1.67(3H,s), 1.59 (3H,s), 1.41(1H,m), 1.18(1H,m), 0.88–0.96(12H,m).

A suspension of N-[$^3$H]-acetyl-S-trans-geranyl-L-cysteine-L-valine-L-isoleucine methyl ester (1.079 mCi, 4.32 $\mu$mol, 250 mCi/mmol) and 0.25M barium hydroxide in methanol-water(1:1.5 mL) was stirred at room temperature for 2 days. 10% HCl was added to pH=2. The mixture was extracted with ethyl acetate (3×30 mL). The combined organic phase was washed with water, dried over anhydrous magnesium sulfate, filtered, and evaporated. The residue was separated by HPLC (Rainin silica, 250×4.6 mm, 1.5 mL/min, hexane/isopropanol/TFA 92:8:0.01, UV detection was at 210 nm). The retention time of the D-L-L isomer was 7.17 min. and for the L-L-L isomer it was 9.65 min. Recovery of radioactivity:D-L-L:0.22 mCi, L-L-L:0.18 mCi.

$^1$HNMR(DMSO-d$_6$,500 MHz) of the authentic non-radioactive peptides:

N-acetyl-S-trans-geranyl-L-Cys-L-Val-L-Ile 8.11(1H,d,J=8 Hz), 7.89(1H,d,J=8 Hz), 7.76(1H,d,J=8.5 Hz), 5.15(1H,t,J=8 Hz), 5.03(1H,t,J=6.5 Hz),4.46(1H,dd,J= 8.5,9 Hz), 4.25(1H,dd,J=7,9 Hz), 4.12(1H,dd,J=6,8 Hz), 3.13(2H,t,J=9 Hz), 2.72(1H,dd,J=6,14 Hz), 2.53(1H,dd,J=9, 14 Hz), 1.94–2.08(5H,m), 1.96(1H,m), 1.83(3H,s), 1.61(3H, s), 1.59 (3H,s), 1.54(3H,s), 1.40(1H,m), 1.18(1H,m), 0.78–0.88(12H,m).

N-acetyl-S-trans-geranyl-D-Cys-L-Val-Ile 8.07(1H,d,J=7 Hz), 8.04(1H,d,J=9 Hz), 7.93(1H,d,J=7.5 Hz), 5.15(1H,t,J=7 Hz), 5.03(1H,t,J=6.5 Hz), 4.56(1H,dd,J= 8, 14.5 Hz), 4.28(1H,dd,J=7,9 Hz), 4.10(1H,dd,J=5.5, 7.5 Hz), 3.16(2H,dd,J=2,8 Hz), 2.67(1H,dd,J=7,13.5 Hz), 2.53 (1H,dd,J=7.5,13.5 Hz), 1.96–2.05(5H,m), 1.96(1H,m), 1.82 (3H,s), 1.61(3H,s), 1.60(3H,s), 1.54(3H,s), 1.41(1H,m), 1.18(1H,m), 0.80–0.86(13H,m).

Synthesis of N-$^3$H]-Acetyl-S-all-trans-geranylgeranyl-L-Cys-L-Val-L-Ile and N-[$^3$H]-Acetyl-S-all-trans-geranylgeranyl-D-cys-L-Val-L-Ile A mixture of S-all-trans-geranylgeranyl-L-Cys-L-Val-L-Val-L-Ile methyl ester (20 mg, 32 $\mu$mol), [$^3$H]-acetic anhydride ($\mu$mol, 2.5 mCi, 500 mCi/mmol), and a catalytic amount of 4,4-dimethylaminopyridine in 4 mL of methylene chlroride was stirred at room temperature overnight. The solvent was evaporated and the residue was partitioned between water and ethyl acetate. The aqueous layer was extracted with ethyl acetate (2×30 mL). The combined organic phase was washed with 10% HCl, saturated sodium bicarbonate, and water, dried over anhydrous magnesium sulfate, filtered, and evaporated. The residue was purified by HPLC (Rainin silica, 250×4.6 mm, 1.5 mL/min, hexane/isopropanol/TFA 90:10:0.01, uv detection was 210 nm). Retention time: 4.70 min. Yield: 0.40 mCi, 1.6 μmol, 32%.

$^1$HNMR (CDCI$_3$,500 MHz) of the authentic non-radioactive peptide methyl ester: 6.92(1H,d,J=9 Hz), 6.57 (1H,d,J=8.5 Hz), 6.47(1H,d,J=7 Hz), 5.26(1H,t,J=8 Hz), 5.09(3H,t,J=5 Hz), 4.57(2H,m), 4.30(1H,dd,J=6,8 Hz), 3.76 (3H,s), 3.22(2H,dd,J=2,7 Hz), 2.90(1H,dd,J=5,13.5 Hz), 2.77(1H,dd,J=7.5, J=7, 14 Hz), 3.16(2H,d,J=8 Hz), 2.66(1H, dd,J=5, 12.5 Hz), 2.52 (1H,dd,J=7.5,12.5 Hz), 1.96–2.08 (13H,m), 1.81(3H,s), 1.78(1H,m), 1.61(6H,s), 1.54(9H,s), 1.42(1H,m), 1.18(1H,m), 0.78–0.86(12H,m).

Syntheses of N-[$^3$H]-acetyl-S-all-trans-farnesyl-L-Cys-D-Val-L-Ile and N-[$^3$H]-acetyl-S-all-trans-farsenyl-D-Cys-D-Val-L-Ile A solution of N-[$^3$H]-acetyl-S-all-<u>trans</u>-farnesyl-cysteine (0.31 mCi, 124 μmol, 250 mCi/mmol, prepared by acetylation of all-<u>trans</u>-farnesyl-L-cysteine), D-valine-L-isoleucine p-nitrobenzyl ester tosylate (40.6 mg, 76 μmol), and 1-hydroxybenzotriazole hydrate (12 mg, 89 μmol) in 6 mL of DMF was cooled to 0° C. N-methylmorpholine (10 mL, 9.2 mg, 91 μmol) and 1-(3-dimethylamino)propyl-3-ethyl carbodiimide hydrochloride (15.2 mg, 80 μmol) were added at 0° C. The mixture was stirred under argon at 0° C. for 2 hours and at room temperature for 22 hours. Water (20 mL) was added and the mixture was extracted with ethyl acetate (3×30 mL). The combined organic phase was washed with 10% HCl, saturated sodium bicarbonate, water, dried over anhydrous magnesium sulfate, filtered, and evaporated. The residue was redissolved in 8 ml of 90% aqueous acetic acid. Zinc dust (500 mg) was added and the mixture was stirred at room temperature for 29 hours. Ethyl acetate (30 mL) was added and the aqueous layer was extracted with ethyl acetate (2×30 mL). The combined organic phase was washed with water, dried over anhydrous magnesium sulfate, filtered, and evaporated. The residue was separated by HPLC (Rainin silica, 4.6×250 mm, hexane/isopropanol/TFA 92:8:0.01, 1.5 mL/min, UV detection was at 210 nm). The recovery of radioactivity was 0.19 mCi for the L-D-L isomer and 0.08 mCi for the D-D-L isomer. The HPLC retention times for the L-D-L and D-D-L isomers were 8.60 min and 6.26 min respectively. $^1$HNMR (DMSO-d$_6$, 500 MHz) of authentic non-radioactive peptides:

N-acetyl-S-all-trans-farnesyl-L-Cys-D-Val-L-Ile 8.11 (1H,d,J=9.5 Hz), 8.09(1H,d,J=7.5 Hz), 8.01(1H,d,J= 7.5 Hz), 5.15(1H,t,J=8 Hz), 5.04(2H,t,J=8 Hz), 4.59(1H,dd, J=8,15 Hz), 4.34(1H,dd,J=6,9 Hz), 4.18(1H,dd,J=6.5, 8.5 Hz), 3.17(2H,dd,J=4,7.5 Hz),2.65(1H,dd,J=6.5,13.5 Hz), 2.51(1H,dd,J=7.5,13.5 Hz), 2.08–1.90(9H,m), 1.80(3H,s), 1.79(1H,m,) 1.61(3H,s), 1.60(3H,s), 1.54(6H,s), 1.38(1H, m), 1.19(1H,m), 0.79–0.87(12H,m).

N-acetyl-S-all-trans-farnesyl-D-Cys-D-Val-L-Ile 8.19(1H,d,J=8.5 Hz), 7.89(1H,brs), 7.77(1H,d,J=8.5 Hz), 5.14(1H,t,J=8 Hz), 5.04(2H,t,J=6 Hz), 4.46(1H,dd,J=7,9 Hz), 4.26(1H,dd,J=6,13 Hz), 4.15(1H,brs), 3.15(1H,d,J=8 Hz), 3.12(1H,d,J=Hz)2.73(1H,dd,J=5.5,12.5 Hz), 2.51(1H, dd,J=8.5,12.5 Hz), 2.06–1.90(9H,m), 1.83(3H,s), 1.78(1H, m), 1.61(3H,s), 1.60(3H,s), 1.53(6H,s), 1.39(1H,m), 1.18 (1H,m), 0.79–0.84(12H,m).

Synthesis of N-[$^3$H]-acetyl-S-all-trans-farnesyl-L-Cys-L-Val-D-Ile 1-(3-Dimethylamino)propyl-3-ethyl carbodiimide hydrochloride (15.2 mg, 80 μmol) were added to a stirred solution of N-[$^3$H]-acetyl-S-all-<u>trans</u>-farnesyl-cysteine (0.31 mCi, 1.24 μmol, 250 mCi/mmol, prepared by acetylation of all-trans-farnesyl-L-cysteine), L-valine-D-isoleucine p-nitrobenzyl ester tosylate (40.6 mg, 76 μmol), 1-hydroxybenzotriazole hydrate (12 mg, 89 μmol), and N-methylmorpholine (10 μL, 9.2 mg, 91 μmol) in 6 mL of DMF at 0° C. The mixture was stirred under argon at 0° C. for 2 hours and at room temperature for 22 hours.

Water (20 mL) was added and the mixture was extracted with ethyl acetate (3×30 mL). The combined organic phase was washed with 10% HCl, saturated sodium bicarbonate, water, dried over anhydrous magnesium sulfate, filtered, and evaporated. The residue was redissolved in 8 mL of 90% aqueous acetic acid. Zinc dust (500 mg) was added and the mixture was stirred at room temperature for 25 hours. The aqueous mixture was extracted with ethyl acetate (3×30 mL). The combined organic phase was washed with water, dried over anhydrous magnesium sulfate, filtered, and evaporated. The residue was separated by HPLC (Rainin silica, 4.6×250 mm, hexane/isopropanol/TFA 92:8:0.01, 1.5 mL/min, UV detection was at 210 nm). The recovery of radioactivity was 0.21 mCi for the L-L-D isomer and 0.07 mCi for the D-L-D isomer. The HPLC retention times for the L-L-D and D-L-D isomers were 8.19 min and 6.42 min respectively. $^1$HNMR (DMSO-d$_6$, 500 MHz) of authentic non-radioactive peptides: L-L-D is same as D-D-L above. D-L-D is same as L-D-L above.

Synthesis of N-[$^3$H]-Acetyl-S-thio-t-butyl-L-Cys-L-Val-L-Ile

A mixture of S-thio-t-butyl-L-Cys-L-Val-L-Ile (5 mg, 11.9 μmol), 16.6 mL of ten times diluted triethylamine with anhydrous methylene chloride (1.1 eqv) and 3.2 mL[$^3$H]-acetic anhydride (4 mmol, 2 mCi, 500 mCi/mmol) in 3.3 mL methylene chloride solution and stirred overnight at room temperature under argon. The mixture was evaporated and the product was separated from the unreacted starting material by reverse phase HPLC on a Dynamax (Rainin), C-18, particle size: 8μ, pore size: 60 A, column size: 10×250 mm. The mobil phase was 10 mM TFA in 1:1 acetonitrile/water and the flow rate was 2.0 mL/min. with detection at 210 nm. The retention time of the product was 14.75 min. and the yield was 94%.

$^1$H NMR (DMSO-d$_6$, 500 MHz): 8.24(1H,d,J=8.0 Hz), 7.93(1H,d,J=7.5 Hz), 7.83(1H,d,J=80 Hz), 4.53(1H,ddd,J= 3.5,8.5,11.5 Hz), 4.23(1H,dd,J=8.5,8.5 Hz), 4.11(1H,dd,J= 6.0,8.0 Hz), 3.03(1H,dd,J=4.5,12.5 Hz), 2.88(1H,dd,J=9, 12.5 Hz), 1.95(1H,m), 1.84(3H,s), 1.35(1H,m), 1.26(9H,s), 1.26–1.17(2H,m), 0.84–0.76(12H,m).

Synthesis of N-[$^3$H]-Acetyl-L-Cys-L-Val-L-Ile

N-[$^3$H]-Acetyl-S-thio-t-butyl-L-Cys-L-Val-L-Ile (0.25 mCi, 250 mCi/mmol, 1 mmol) was stirred with a 10-fold excess of tributyl phosphine in 500 μL of 20% aqueous n-propanol (w/w) under argon at room temperature for 48 h.

The reaction mixture was then freeze-dried and the product was purified from the residue by reverse phase HPLC as described above. The purified compound gave positive DTNB test for free sulfhydryl group and had a retention time of 7.27 min. The yield of purified material was 15%.

N-[$^3$H]-acetyl-S-all-trans-farnesyl-L-Cys-L-Val-L-Ile-D-Met or N-[$^3$H]acetyl-S-all-trans-farnesyl-L-(SEQ ID NO: 2) methyl ester A mixture of S-all-trans-farnesyl-L-cysteine-L-valine-L-isoleucine-D-methionine methyl ester (20 mg, 26 μmol), [$^3$H]-acetic anhydride (4 μmol, 2 mCi, 500 mCi/mmol), and a catalytic amount of 4,4-dimethylaminopyridine in 3.2 mL of methylene chloride was stirred at room temperature overnight. Water was added and the mixture was extracted with ethyl acetate three times. The combined organic phase was washed with 10% HCl saturated sodium bicarbonate, water, dried over anhydrous magnesium sulfate, filtered, and evaporated. The residue was purified by HPLC (Rainin silica, 250×4.6 mm, 1.5 mL/min, hexane/isopropanol 85:15, uv detection was at 210 nm). Retention time: 5.15 min. Yield: 0.134 mCi, 0.54 μmol, 13.4%.

$^1$HNMR (CDCl$_3$, 500 MHz) of the authentic non-radioactive peptide methyl ester: 6.96(2H, brs), 6.58(2H,brs) 5.25(1H,t,J=7 Hz), 5.09(2H,t,J=6 Hz), 4.72–4.62(2H,m), 4.44(1H,dd,J=6,12 Hz), 4.08(1H,t,J=8 Hz), 3.76(3H,s), 3.25 (2H,t,J=8 Hz), 2.93(1H,dd,J=5,14 Hz), 2.83(1H,dd,J=8,14 Hz), 2.54(2H,m), 2.30(1H,m), 2.18–2.04(9H,m), 2.08(3H, s), 2.04(3H,s), 1.97(2H,m), 1.69(3H,s), 1.68(3H,s), 1.58 (6H,s), 1.44(1H,m), 1.10(1H,m), 0.93(12H,m).

N-[$^3$H]-acetyl-S-all-trans-farnesyl-L-Cys-L-Val-L-Ile-D-Met or N-[$^3$H]acetyl-S-all-trans-farnesyl-L-(SEQ ID NO: 2)

A solution of N-[$^3$H]-acetyl-S-all-trans-farnesyl- L-cysteine-L-valine-L-isoleucine-D-methi\ onine methyl ester (0.134 mCi,0.54 μmol,250 mCi/mmol) and 10% sodium carbonate (10 mL) in acetonitrile (10 mL) was stirred at room temperature of 36 hours. 10% HCl was added to pH=2. The mixture was extracted with ethyl acetate (3×30 mL). The combined organic phase was washed with water, dried over anhydrous magnesium sulfate, filtered, and evaporated. The residue was separated by HPLC (Rainin silica, 250×4.6 mm, 1.5 mL/min, hexane/isopropanol/TFA 90:10:0.01, UV detection was at 210 nm). The retention time was 9.38 min. Recovery of radioactivity: 0.094 mCi, 70%.

$^1$HNMR (DMSO-d$_6$, 500 MHz) of the authentic non-radioactive peptide: 8.15(1H,d,J=8 Hz), 8.13(1H,d,J=8.5 Hz), 7.86(1H,d,J=9 Hz), 7.75(1H,d,J=8.5 Hz), 5.15(1H,t,J= Hz), 5.04(2H,d,J=3.5 Hz), 4.46(1H,dd,J=8,14 Hz), 4.28–4.16(3H,m), 3.13(2H,d,J=7.5 Hz), 2.71(1H,dd,J=6,14 Hz), 2.51(1H,dd,J=8.5,14 Hz), 2.46–2.39(3H,m), 1.99(3H, s), 2.03–1.90(10H,m), 1.82(3H,s), 1.68(1H,m), 1.61(3H,s), 1.59(3H,s), 1.53(6H,s), 1.39(1H,m), 1.03(1H,m), 0.78(12H, m).

N-[$^3$H]-acetyl-S-all-trans-farnesyl-L-Cys-L-Val-L-Ile-L-Met or N-[$^3$H]acetyl-S-all-trans-farnesyl-L-(SEQ ID NO: 2) methyl ester A mixture of S-all-trans-farnesyl-L-cysteine-L-valine-L-isoleucine-L-meth ionine or S-all-trans-farnesyl-L-(SEQ ID NO: 2) methyl ester (20 mg, 26 μmol), [$^3$H]-acetic anhydride (10 μmol, 5 mCi, 500 mCi/mmol, and a catalytic amount of 4,4-dimethylaminopyridine in 8 ml of methylene chloride was stirred at room temperature overnight. Water was added and the mixture was extracted with ethyl acetate three times. The combined organic phase was washed with 10% HCl, saturated sodium bicarbonate, water, dried over anhydrous magnesium sulfate, filtered, and evaporated. The residue was purified by HPLC (Rainin silica, 250×4.6 mm, 1.5 ml/min, hexane/isopropanol 85:15, uv detection was at 210 nm). Retention time: 4.26 min. Yield: 0.588 Ci, 2.5 μmol, 12%.

$^1$HNMR (DMSO-d$_6$, 500 MHz) of the authentic non-radioactive peptide methyl ester:8.31(1H,d,J=6.5 Hz), 8.13 (1H,d,J=8 Hz), 7.81(2H,d,J=8.5 Hz), 5.15(1H,t,J=8 Hz), 5.04(2H,m), 4.45(1H,ddd,J=2,9,14.5 Hz), 4.36(1H,ddd,J=2, 5,9.5 Hz), 4.18(1H,dd,J=6.5,8.5 Hz), 4.15(1H,t,J=9 Hz), 3.13(2H,d,J=7.5 Hz), 2.71(1H,dd,J=6,13.5 Hz), 2.50(1H,dd, J=8,13.5 Hz), 2.49(1H,m),2.41(1H,m), 2.03–1.89(10H,m), 2.00(3H,s), 1.82(3H,s), 1.68(1H,m), 1.61(3H,s), 1.59(3H,s), 1.53(6H,s), 1.41(1H,m), 1.05(1H,m), 0.79(12H,m).

N-[$^3$H]-acetyl-S-all-trans-farnesyl-L-Cys-L-Val-L-Ile-L-Met or N-[$^3$H]acetyl-S-all-trans-farnesyl-L-(SEQ ID NO: 2)

A solution of N-[$^3$H]-acetyl-S-a ll-trans-farnesyl-L-cysteine-L-valine-L-isoleucine-L-methi onine methyl ester (0.588 mCi, 2.35 mmol, 250 μmmol, 250 μCi/mmol) and 10% sodium carbonate (10 mL) in acetonitrile (10 mL) was stirred at room temperature for 36 hours. 10% HCl was added to pH=2. The mixture was extracted with ethyl acetate (3×30 mL). The combined organic phase was washed with water, dried over anhydrous magnesium sulfate, filtered, and evaporated. The residue was separated by HPLC (Rainin silica, 250×4.6 mm, 1.5 mL/min, hexane/isopropanol/TFA 90:10:0.01, uv detection was at 210 nm). The retention time was 6.68 min. Recovery of radioactivity:0.29 mCi, 49%.

$^1$HNMR (DMSO-d$_6$, 500 MHz) of the authentic non-radioactive peptide: 8.14(1H,d,J=8 Hz), 8.12(1H,d,J=8 Hz), 7.85(1H,d,J=8.5 Hz), 7.81(1H,d,J=9.5 Hz), 5.15(1H,t,J=8 Hz), 5.05(2H,m), 4.46(1H,ddd,J=2,6, 14.5 Hz), 4.39(1H,dd, J=5.5,9.5 Hz), 4.33(1H,ddd,J=5,10,14 Hz), 4.23(1H,dd,J=7, 8.5 Hz), 3.17(1H,dd,J=8,14 Hz), 3.12(1H,dd,J=7.5,14 Hz), 2.74(1H,dd,J=6,13.5 Hz), 2.52(1H,dd,J=7.5,13.5 Hz), 2.46–2.35(3H,m), 2.00(3H,s), 2.04–1.90(10H,m) 1.83(3H, s), 1.61(3H,s), 1.60(3H,s), 1.53(6H,s), 1.24(2H,m), 1.08 (1H,m), 0.80(12H,m).

Design and Screening of Inhibitors

The structure/activity studies described above suggest that the isoprenylated cysteine residue is an important determinant of substrate activity. The fact that AFC-val-ile-ser, AFC-val-ile, and AFC-val are substrates for the enzyme, although the latter two peptides are weaker substrates than the tetrapeptide, suggests that the nature of the amino acid residues attached to the modified cysteine residue is not of critical importance. The fact that an isoprenoid moiety is required for substrate activity suggests that inhibitors preferably include such a moiety. The observed steroselectivity and sterospecificity of the protease activity suggest that the L isomer is preferred for any amino acids or amino acid derivatives.

Preferred inhibitors are related to AFC-tripeptides wherein the bond between the cysteine and the peptide is resistant to proteolytic digestion. The design of protease resistant bonds is well known to those skilled in the art.

Figure 5:
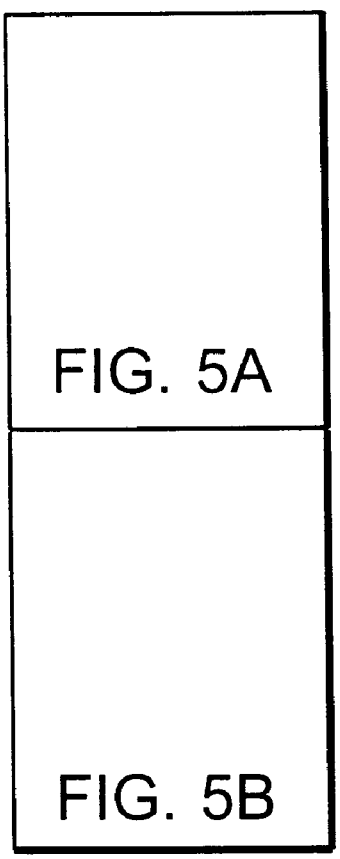
FIG. 5 is a set of schematic drawings of various inhibitors and, for some the measured Ki.
Figure 10:
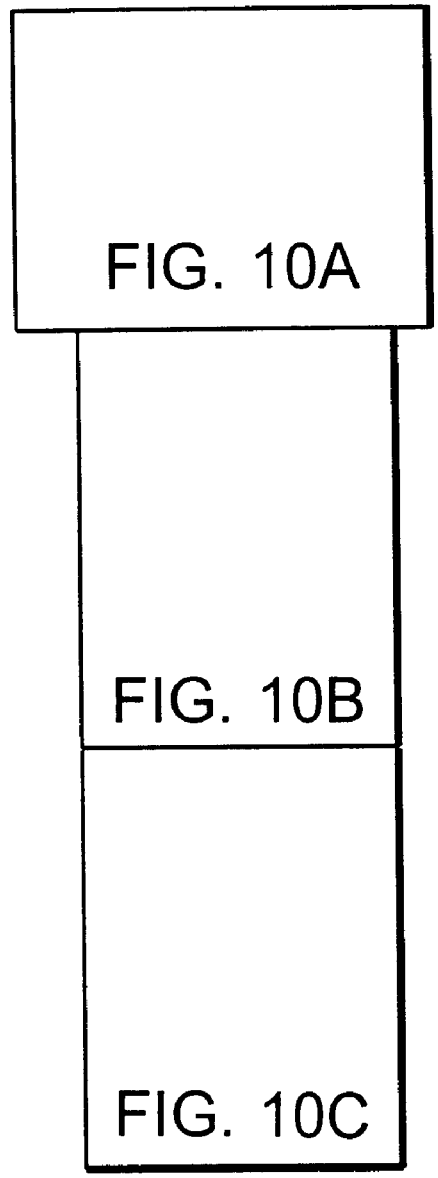
FIG. 10 is a schematic illustration of the synthesis of N-Boc-S-Farnesyl statine derivatives.
Figure 5A:
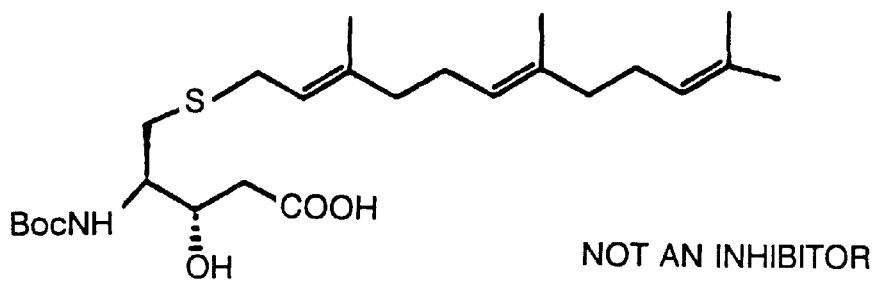
Figure 5A:
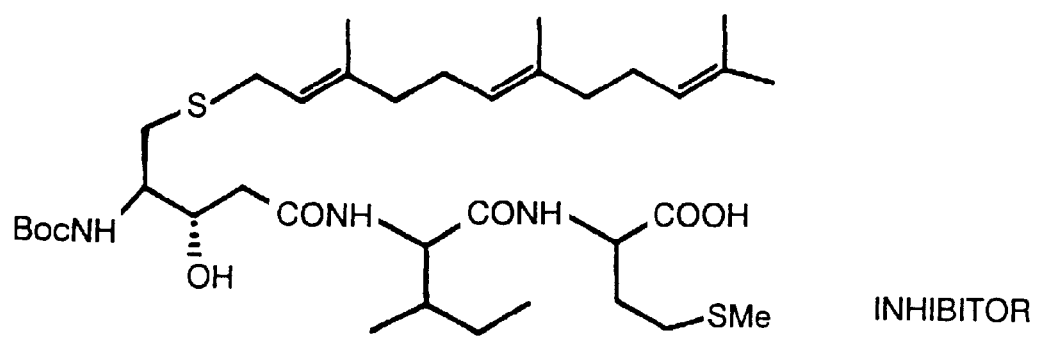
Figure 5A:
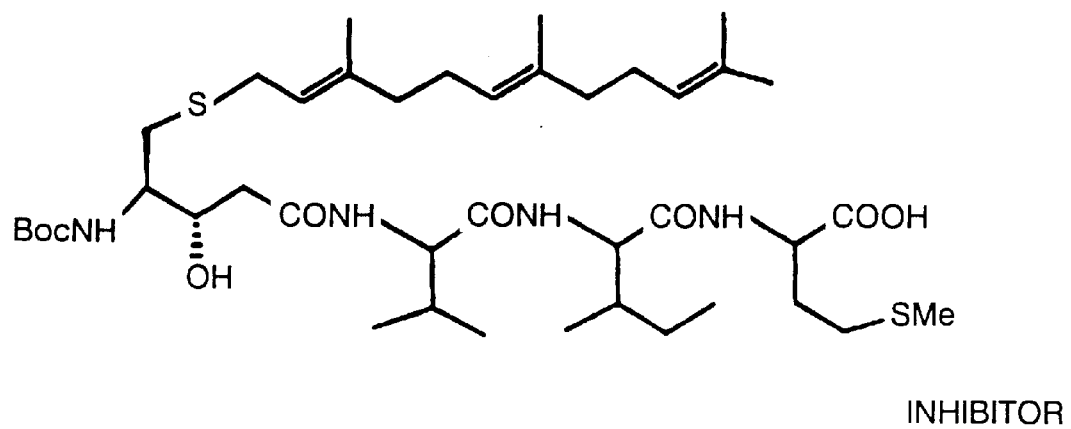
Figure 5B:
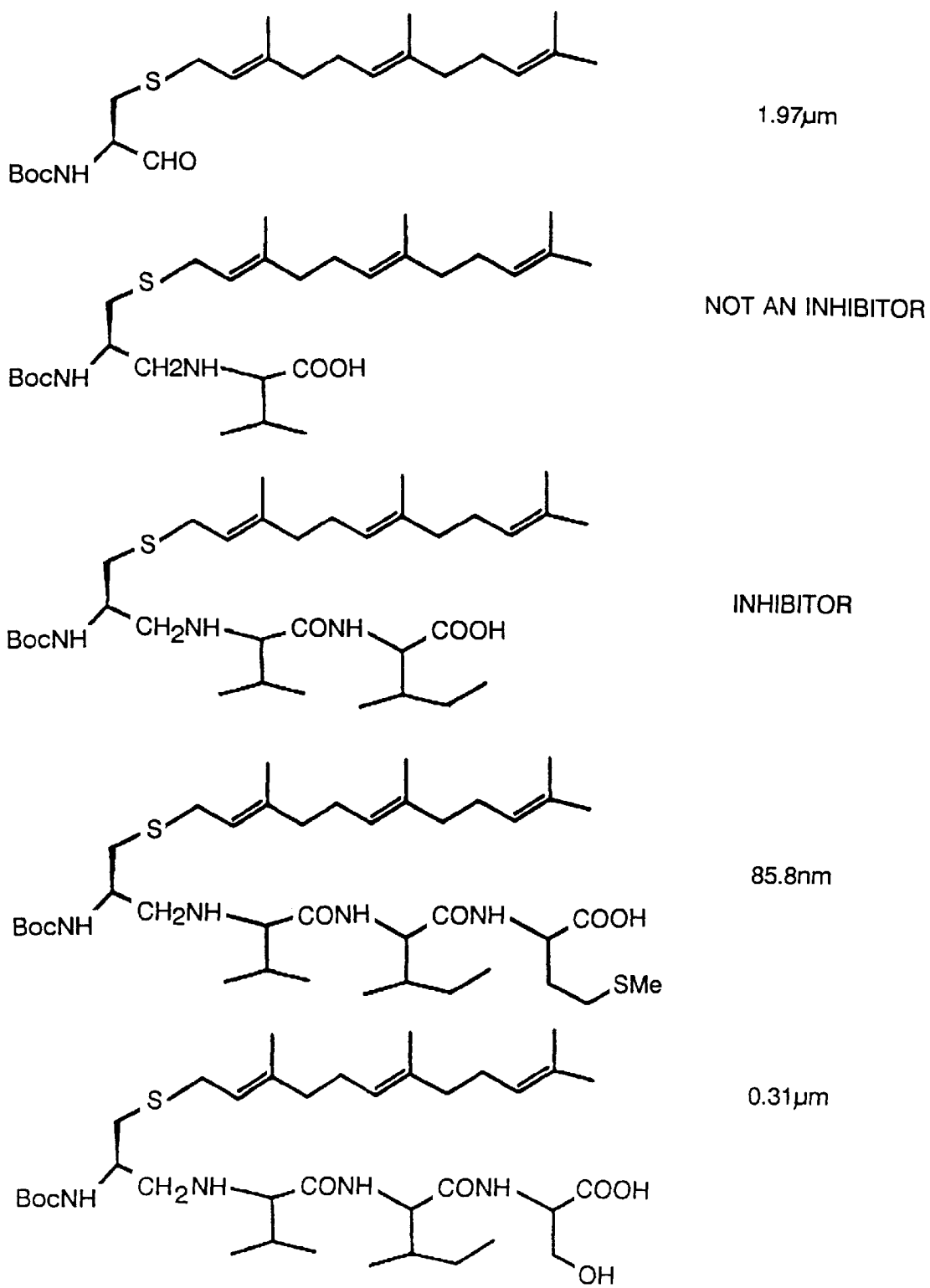
Figure 6:
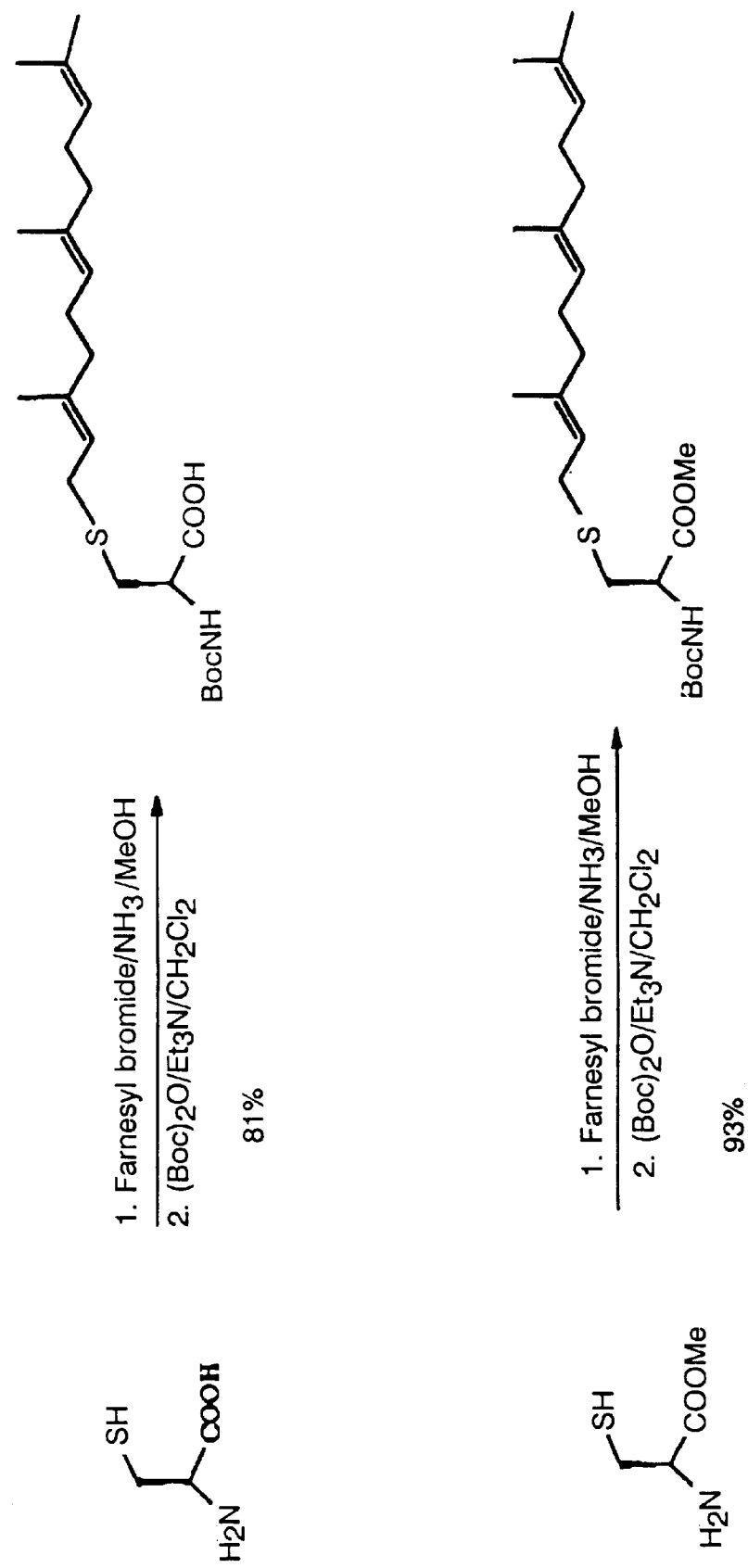
FIG. 6 is a schematic illustration of the synthesis of Boc-S-Farnesyl L-cys and its methyl ester.

Using these guidelines the compounds listed in FIG. 5 were prepared. The ability of these compounds to act as inhibitors was tested as described above. These molecules illustrate some of the possible inhibitors; the list is not intended to limit the invention.

Synthesis and Structure Confirmation

N-[$^3$H]-Acetyl-S-all-trans-farnesyl-L-Cys-D-Val-L-Ile

The peptide was purified by HPLC (Rainin silica, 4.6×250 mm, hexane/isopropanol/TFA 92:8:0:0.01 as eluant at a flow rate of 1.5 mL/min with UV detection at 210 nm). The retention time of the L-D-L isomer was 8.60 min.

$^1$HNMR (DMSO-d$_6$, 500 MHz):8.11 (1H,d,J=9.5 Hz), 8.09 (1H,d, J=7.5 Hz), 8.01 (1H,d,J=7.5 Hz), 5.15 (1H,t,J=8 Hz), 5.04 (2H,t,J=8 Hz), 5.04 (2H,t,J=8 Hz), 4.59 (1H,dd, J=8,15 Hz), 4.34 (1H,dd, J=6, 9 Hz), 4.18 (1H,dd, J=6.5, 8.5 Hz), 3.17(2H,dd, J=4,7.5 Hz), 2.65 (1H,dd,J=6.5,13.5 Hz), 2.51 (1H,dd,J=7.5, 13.5 Hz), 2.08–1.90 (9H,m), 1.80 (3H,s), 1.79 (1H,m), 1.61 (3H,s), 1.60(3H,s), 1.54 (6H,s), 1.38 (1H,m), 1.19(1H,m), 0.79–0.87 (12H,m).

N-[$^3$H]-Acetyl-S-all-trans-farnesyl-L-Cys-L-Val-D-ile

The retention time of the L-L-D isomer was 8.19 min, $^1$HNMR (DMSO-d$_6$, 500 MHz) 8.19(1H,d,J=8.5 Hz), 7.89 (1H, brs), 7.77 (1H, d, J=8.5 Hz), 5.14 (1H, t, J=8 Hz), 5.04 (2H, t, J=6 Hz), 4.46 (1H, dd, J=7, 9 Hz), 4.26 (1H,dd,J=6, 13 Hz), 4.15 (1H,brs), 3.15(1H,d,J=8 Hz), 3.12 (1H,d,J=8 Hz), 2.73(1H,dd,J=5.5, 12.5 Hz), 2.51 (1H, dd, J=8.5, 12.5 Hz), 2.06–1.90 (9H,m), 1.83 (3H,s), 1.78 (1H, m), 1.61 (3H,s), 1.60 (3H,s),1.53(6H,s), 1.39(1H,m), 1.18 (1H,m), 0.79–0.84(12H,m).

N-[$^3$H]-Acetyl-S-all-trans-farnesyl-L-Cys-L-Val-L-ile-D-Met or N-[$^3$H]acetyl-S-all-trans-farnesyl-L-(SEQ ID NO: 2)

The peptide was purified by HPLC chromatography (Rainin silica, 250×4.6 mm, 1.5 ml/min, hexane/isopropanol/TFA 90:10:0.01, uv detection was at 210 nm). The retention time was 9.38 min.

$^1$HNMR: (DMSO-d$_6$, 500 MHz) 8.15 (1H,d, J=8 Hz), 8.13 (1H, d, J=8.5 Hz), 7.86 (1H, d, J=9 Hz), 7.75 (1H, d, J=8.5 Hz), 5.15 (1H, t, J=7 Hz), 5.04 (2H, d, J=3.5 Hz), 4.46 (1H, dd, J=8, 14 Hz), 4.28–4.16 (3H, m), 3.13 (2H, d, J=7.5 Hz), 2.71 (1H,dd,J=6, 14 Hz), 2.51 (1H, dd, J=8.5, 14 Hz), 2.46–2.39(3H, m), 1.99 (3H,s), 2.03 –1.90 (10H,m), 1.82 (3H,s), 1.68 (1H,m), 1.61 (3H,s), 1.59 (3H,s), 1.53 (6H,s), 1.39 (1H,m), 1.03(1H,m), 0.78 (12H,m).

N-[$^3$H]-Acetyl-S-all-trans-farnesyl-L-Cys-L-Val-L-ile-L-Met or N-[$^3$H]acetyl-S-all-trans-farnesyl-L-(SEQ ID NO: 2)

The peptide was purified by HPLC (Rainin silica, 250×4.6 mm, 1.5 ml/min, hexane/isopropanol/TFA 90:10:0.01, uv detection was at 210 nm). The retention time was 6.68 min.

$^1$HNMR:(DMSO-d$_6$, 500 MHz) 8.14 (1H, d, J=8 Hz), 8.12 (1H, d, J=8 Hz), 7.85 (1H, d, J=8.5 Hz), 7.81 (1H,d, J=9.5 Hz), 5.15(1H,t,J=8 Hz), 5.05(2H,m), 4.46 (1H,ddd,J=2,6, 14.5 Hz), 4.39(1H,dd,J=5.5, 9.5 Hz), 4.33(1H,ddd,J=5, 10,14 Hz), 4.23 (1H,dd,J=7,8.5 Hz), 3.17(1H,dd,J=8,14 Hz), 3.12(1H,dd,J=7.5,14 Hz), 2.74(1H,dd,J=6,13.5 Hz), 2.52 (1H,dd,J=7.5,13.5 Hz),2.46–2.35 (3H,m), 2.00(3H,s), 2.04–1.90(10H,m), 1.83(3H,s), 1.61(3H,s), 1.60(3H,s), 1.53 (6H,s), 1.24(2H,m), 1.08(1H,m), 0.80(12H,m).

N-[$^3$H]-Acetyl-S-trans-geranyl-L-Cys-L-Val-L-ile

The peptide was purified by HPLC (Rainin silica, 250×4.6 mm, 1.5 ml/min, hexane/isopropanol/TFA 92:8:0.01; uv detection was at 210 nm). The retention time of the L-L-L isomer was 9.65 min.

$^1$HNMR (DMSO-d$_6$, 500 MHz):8.11 (1H,d,J=8 Hz), 7.89 (1H,d,J=8 Hz), 7.76 (1H, d,J=8.5 Hz), 5.15(1H,t,J=8 Hz), 5.03(1H,t,J=6.5 Hz), 4.46(1H,dd,J=8.5,9 Hz), 4.25(1H,dd, J=7,9 Hz), 4.12(1H,dd,J=6,8 Hz), 3.13 (2H,t,J=9 Hz),2.72 (1H,dd,J=6,14 Hz),2.53(1H,dd,J=9,14 Hz), 1.94–2.08(5H, m), 1.96(1H,m), 1.83(3H,s), 1.61 (3H,s), 1.59(3H,s), 1.54 (3H,s), 1.40(1H,m), 1.18(1H,m), 0.78–0.88(12H,m).

N-[$^3$H-Acetyl-S-all-trans-geranylgeranyl-L-Cys-L-Val-L-ile

The peptide was purified by HPLC (Rainin silica, 250×4.6 mm, 1.5 ml/min, hexane/isopropanol/TFA 92:8:0.01; uv detection was at 210 nm). The retention time of the L-L-L isomer was 7.08 min.

$^1$HNMR (DMSO-d$_6$, 500 MHz):8.11 (1H,d,J=8 Hz), 7.89 (1H,d,J=8 Hz), 7.76 (1H,d,J=8.5 Hz), 5.15(1H,t,J=8 Hz), 5.03(1H,t,J=6.5 Hz), 4.46 (1H,dd, J=8.5,9 Hz), 4.25(1H,t, J=7 Hz), 4.11 (1H,t,J=6 Hz), 3.12(2H,d,J=6.5 Hz), 2.73(1H, dd,J=5.5, 13.5 Hz), 2.53(1H,dd,J=8.5,13.5 Hz), 1.92–2.08 (13H,m), 1.83(3H,s, 1.76(1H,m), 1.61(3H,s), 1.60(3H,s), 1.54(9H,s), 1.41(1H,m), 1.17(1H,m), 0.78–0.86(12H,m).

N-[3H]-acetyl-S-all-trans-farnesyl-L-Cys-L-Val-L-Ile-L-Met

A solution of N-[$^3$H]-acetyl-S-all-trans-farnesyl-L-Cys-L-Val-L-Ile-L-Met methyl ester (Ma et al., 1992 supra) (0.588 mCi, 2.35 μmol, 250 mCi/mmol) in aqueous 10% Na$_2$CO$_3$ (10 mL) in CH$_3$OH:CH$_3$CN (1:1, 10 mL) was stirred at room temperature for 16 h. The reaction mixture was acidified to pH=2 with aqueous 10% HCl. The combined organic layers were washed with brine, dried over anhydrous MgSO$_4$, filtered, and evaporated. The residue was purified by normal phase HPLC (Rainin silica, 250×4.6 mm, 1.5 mL/min, hexane/isopropanol/TFA (90:10:0.01), UV detection was at 210 nm). The retention time was 6.68 min. Recovery of radioactivity: 0.29 mCi, 49%.

$^1$H NMR (DMSO-d$_6$, 500 MHz) of the authentic non-radioactive peptide: 8.14 (1H, d, J=8 Hz), 8.12 (1H, d, J=8 Hz), 7.85 (1H, d, J=8.5 Hz), 7.81 (1H, d, J=9.5 Hz), 5.15 (1H, t, J=8 Hz), 5.05 (2H, m), 4.46 (1H, ddd, J=2, 6, 14.5 Hz), 4.39 (1H, dd, J=5.5, 9.5 Hz), 4.33 (1H, ddd, J=5, 10, 14 Hz), 4.23 (1H, dd, J=7, 8.5 Hz), 3.17 (1H, dd, J=8, 14 Hz), 3.12 (1H, dd, J=7.5, 14 Hz), 2.74 (1H, dd, J=6, 13.5 Hz), 2.52 (1H, dd, J=7.5, 13.5 Hz), 2.46–2.35 (3H, m), 2.00 (3H, s), 2.04–1.90 (10H, m), 1.83 (3H, s), 1.61 (3H, s), 1.60 (3H, s), 1.53 (6H, s), 1.24 (2H, m), 1.08 (1H, m), 0.80 (12H, m).

N-Boc-S-all-trans-farnesyl-L-cysteine

To a solution of cysteine (1.07 g, 8.83 mmol) in saturated NH$_3$—MeOH (40 mL) at 0° C. was added all-trans-farnesyl bromide (2.39 mL, 2.52 g, 8.83 mmol) in one portion (Brown et al., 1991). The mixture was stirred at 0° C. for 1 h, then at room temperature overnight. The solvent was evaporated and the residue dried under vacuum. The residue was dissolved in DCM (45 mL), followed by the addition of di-tert-butyl dicarbonate (2.89 g, 13.2 mmol) and triethylamine (1.85 mL, 1.34 g, 13.2 mmol). The mixture was stirred at room temperature for 18 h. The solvent was evaporated and the residue extracted with EtOAc (3×100 mL). The combined organic layer was washed with aqueous 5% HCl, then with brine, then dried over anhydrous MgSO$_4$, filtered, and evaporated. The residue was purified by silica gel chromatography (hexane/acetone 80:20, 70:30) to give the title compound (2.95 g, 79%).

$^1$H NMR (CDCl$_3$, 500 MHz): 5.34 (1H, brs), 5.22 (1H, t, J=8 Hz), 5.09 (2H, t, J=6 Hz), 4.49 (1H, brs), 3.20 (2H, m), 2,96 (1H, dd, J=4, 13.5 Hz), 2.88 (1H, dd, J=5, 13.5 Hz), 2.12–2.02 (6H, m), 1.96 (2H, t, J-9 Hz), 1.67 (3H, s), 1.66 (3H, s), 1.59 (6H, s), 1.45 (9H, s).

N-Boc-S-all-trans-farnesyl-L-cysteine Methyl Ester

To a solution of cysteine methyl ester hydrochloride (1.16 g, 6.78 mmol) in saturated NH$_3$—MeOH (40 mL) at 0° C. was added all-trans-farnesyl bromide (1.84 mL, 1.93 g, 6.78 mmol) in one portion (Brown et al., 1991). The mixture was stirred at 0° C. for 1 h, then at room temperature overnight. The solvent was evaporated and the residue dried under vacuum. The residue was dissolved in DCM (40 mL) followed by the addition of di-tert-butyl dicarbonate (2.22 g, 10.1 mmol) and triethylamine (1.42 mL, 1.03 g, 10.1 mmol). The mixture was stirred at room temperature for 16 hours. The solvent was evaporated and the residue extracted with EtOAc (3×100 mL). The combined organic layers were washed with aqueous 5% HCl, saturated NaHCO$_3$, brine, dried over anhydrous MgSO$_4$, filtered, and evaporated. The residue was purified by silica gel chromatography (hexane/acetone 80:20) to give the title compound (2.77 g, 93%).

$^1$H NMR (CDCl$_3$, 500 MHz): 5.30 (1H, d, J=7.5 Hz), 5.21 (1H, t, J=7.5 Hz), 5.09 (2H, brs), 4.52 (1H, brs), 3.76 (3H, s), 3.16 (2H, m), 2.91 (1H, dd, J=3.5, 13.5 Hz), 2.85 (1H, dd, J=6, 13.5 Hz), 2.12–1.95 (8H, m), 1.68 (3H, s), 1.66 (3H, s), 1.60 (6H, s), 1.44 (9H, s).

N-Boc-S-all-trans-farnesyl-L-cysteine Aldehyde (2)

To a solution of N-Boc-S-all-trans-farnesyl-L-cystein methyl ester (1.40 g, 3.19 mmol) in dry toluene (10 mL) at −60° C. was added diisobutylaluminum hybride (McNulty & Still, 1992) (1.0 M in toluene, 8.00 mL, 8.00 mmol) over a 90 min period. After 2 h at −60° C., dry methanol (2.0 mL) was carefully added, followed by aqueous 10% potassium sodium tartrate tetrahydrate (20 mL, 7.00 g, 24.8 mmol). The mixture was stirred at room temperature for 2 h until two layers formed. The toluene layer was separated and the aqueous layer extracted with EtOAc (3×100 mL). The combined organic layers were washed with aqueous 5% HCl, and with brine, dried over anhydrous MgSO$_4$, filtered, and evaporated. Due to the compound's relative instability, the crude material was used directly in the next step without further purification.

$^1$H NMR (CDCL$_3$, 500 MHz): 9.67 (1H, d, J=8 Hz), 5.34 (1H, brs), 5.22 (1H, t, J=8 Hz), 5.09 (2H, t, J=6 Hz), 4.49 (1H, brs), 3.20 (2H, m), 2,96 (1H, dd, J=4, 13.5 Hz), 2.88 (1H, dd, J=5, 13.5 Hz), 2.12–2.02 (6H, m), 1.98–1.90 (2H, m), 1.67 (3H, s), 1.66 (3H, s), 1.59 (6H, s), 1.45 (9H, s).

N-Boc-S-all-trans-farnesyl-L-Cys-$^\Psi$(CH$_2$—NH)-L-Val(7)

To a mixture of N-Boc-S-all-trans-farnesyl-L-cysteinal (668 mg, 1.63 mmol) and L-valine (230 mg, 1.97 mmol) in 1% AcOH—MeOH (7.0 mL) was added dropwise a solution of sodium cyanobrohydride (Rodriguez, 1986) (240 mg, 3.87 mmol) in MeOH (3.0 mL) over a 30 min period. The reaction mixture was stirred for an additional 2 h, then concentrated under reduced pressure. The residue was dissolved in saturated aqueous NaHCO$_3$ (20 mL) and extracted with EtOAc (3×50 mL). The combined organic layers were washed with aqueous 5% HCl, and with brine, dried over anhydrous MgSO$_4$, filtered, and evaporated. The residue was purified by normal phase HPLC (Rainin silica, 250×4.6 mm, 2.5 mL/min, hexane/isopropanol/TFA (95:5:0.01), UV detection was at 210 nm). The retention time was 4.80 min.

$^1$H NMR (DMSO-d6, 500 MHz): 8.80 (1H, brs), 8.53 (1H, brs), 6.71 (1H, d, J=8.9 Hz), 5.14 (1H, t, J=7.9 Hz), 5.04 (2H, t, J=5.9 Hz), 3.55 (1H, brs), 3.28 (2H, d, J-11.5 Hz), 3.09 (1H, d, J=7.9), 2.83 (1H, d, J=5.5 Hz), 2.62–2.52 (2H, m), 2.42–2.32 (2H, m), 2.06–1.92 (6H, m), 1.94–1.86 (2H, m), 1.61 (3H, s), 1.59 (3H, s), 1.53 (6H, s), 1.35 (9H, s), 0.83 (6H, t, J=7 Hz).

N-Boc-S-all-trans-farnesyl-L-Cys-$^\Psi$(CH$_2$—NH)-L-Val-L-Ile(8)

To a mixture of N-Boc-S-all-trans-farnesyl-L-cysteinal (602 mg, 1.47 mmol) and L-Val-L-Ile (406 mg, 1.76 mmol) in 1% AcOH—MeOH (6.0 mL) was added dropwise a solution of sodium cyanoborohydride (220 mg, 3.54 mmol) in MeOH (2.0 mL) over a 30 min period. The reaction mixture was stirred for an additional 2 h, then concentrated under reduced pressure. The residue was dissolved in saturated aqueous NaHCO$_3$ (30 mL) and extracted with EtOAc (3×50 mL). The combined organic layers were washed with aqueous 5% HCl, and with brine, dried over anhydrous MgSO$_4$, filtered, and evaporated. The residue was purified by normal phase HPLC (Rainin silica, 250×4.6 mm, 2.5 mL/min, hexane/isopropanol/TFA (95:5:0.01), UV detection was at 210 nm). The retention time was 3.50 min.

$^1$H NMR (DMSO-$d_6$, 500 MHz): 8.84 (1H, d, J=7.9 Hz), 8.57(1H, brs), 6.94 (1H, d, J=8.9 Hz), 5.16 (1H, t, J-7.9 Hz), 5.05 (2H, t, J=5.9 Hz), 4.25 (1H, dd, J=8, 6 Hz), 3.88–3.76 (2H, m), 3.18 (1H, dd, J=13, 8 Hz), 3.11 (1H, dd, J=13, 8 Hz), 2.97 (1H, brs), 2.89 (1H, brs), 2.52 (2H, d, J=7 Hz), 2.28–2.16 (1H, m), 2.06–1.92 (6H, m), 1.94–1.88 (2H, m), 1.86–1.80 (1H, m), 1.61 (3H, s), 1.59 (3H, s), 1.53 (6H, s), 1.38 (9H, s), 1.22–1.19 (1H, m), 1.15 (3H, t, J=7 Hz), 1.01 (3H, d, J=7 Hz), 0.92 (3H, d, J=7 Hz), 0.88–0.83 (5H, m).

N-Boc-S-all-trans-farnesyl-L-Cys-$^\Psi$(CH$_2$—HN)-L-Val-L-Ile-L-Ser or N-Boc-S-all-trans-farnesyl-L-Cys-$^\Psi$(CH$_2$—HN)-(SEQ ID NO: 1) Methyl Ester To a mixture of N-Boc-S-all-trans-farnesyl-L-cysteinal (818 mg, 2.00 mmol) and L-Val-L-Ile-L-Ser methyl ester hydrochloride (820 mg, 2.19 mmol) in 1% AcOH—MeOH (7.0 mL) was added dropwise a solution of sodium cyanoborohydride (255 mg, 4.13 mmol) in MeOH (2.0 mL) over a 30 min period. The reaction mixture was stirred for an additional 2 h, then concentrated under reduced pressure. The residue was dissolved in saturated aqueous NaHCO$_3$ (30 mL) and extracted with EtOAc (3×50 mL). The combined organic layers were washed with 5% HCl, brine, dried over anhydrous MgSO$_4$, filtered, and evaporated. The residue was purified by normal phase HPLC (Rainin silica, 250×4.6 mm, 2.5 mL/min, hexane/isopropanol/TFA (97:3:0.01), UV detection was at 210 nm). The retention time was 8.91 min.

$^1$H NMR (DMSO-d6, 500 MHz): 8.18 (1H, d, J=8 Hz), 8.10 (1H, d, J=8 Hz), 7.76 (1H, d, J=8.5 Hz), 7.79 (1H, d, J=9.5 Hz), 5.15 (1H, t, J=8 Hz), 5.05 (2H, m), 4.46 (1H, ddd, J=2, 6, 14.5 Hz), 4.39 (1H, dd, J=5.5, 9.5 Hz), 4.33 (1H, ddd, J=5, 10, 14 Hz), 4.23 (1H, dd, J=7, 8.5 Hz), 3.17 (1H, dd, J=8, 14 Hz), 3.12 (1H, dd, J=7.5, 14 Hz), 2.74 (1H, dd, J=6, 13.5 Hz), 2.52 (1H, dd, J=7.5, 13.5 Hz), 2.46–2.35(3H, m), 2.00 (3H, s), 2.04–1.90 (10H, m), 1.83 (3H, s), 1.61 (3H, s) 1.60 (3H, s), 1.53 (6H, s), 1.24 (2H, m), 1.08 (1H, m), 0.80 (12H, m).

N-Boc-S-all-trans-farnesyl-L-Cys-$^\Psi$(CH$_2$—NH)-L-Val-L-Ile-L-Ser or N-Boc-S-all-trans-farnesyl-L-Cys-$^\Psi$(CH$_2$—HN)-(SEQ ID NO: 1)

A mixture of N-Boc-S-all-trans-farnesyl-L-Cys-$^\Psi$(CH$_2$—NH)-L-Val-L-Ile-L-Ser methyl ester (110 mg, 0.13 mmol) and 10% $Na_2CO_3$ (10 mL) in $CH_3OH:CH_3CN$ (1:1, 10 mL) was stirred at room temperature for 16 h. The reaction mixture was acidified to pH=2 with aqueous 10% HCl. The solution was extracted with EtOAc (3×40 mL) and the combined organic layers were washed with brine, dried over anhydrous $MgSO_4$, filtered and evaporated. The residue was purified by normal phase HPLC (Rainin silica, 250×4.6 mm, 2.5 mL/min, hexane/isopropanol/TFA (90:10:0.01), UV detection was at 210 nm). The retention time was 10.10 min.

$^1$H NMR (DMSO-d6, 500 MHz): 8.86 (1H, brs), 8.62 (1H, brs), 8.14 (1H, d, J=8 Hz), 8.12 (1H, d, J=8 Hz), 7.85 (1H, d, J=8.5 Hz), 7.81 (1H, d, J=9.5 Hz), 5.15 (1H, t, J=8 Hz), 5.05 (2H, m), 4.46 (1H, ddd, J=2, 6, 14.5 Hz), 4.39 (1H, dd, J=5.5, 9.5 Hz), 4.33 (1H, ddd, J=5, 10, 14 Hz), 4.23 (1H, dd, J=7, 8.5 Hz), 3.17 (1H, dd, J=8, 14 Hz), 3.12 (1H, dd, J=7.5, 14 Hz), 2.74 (1H, dd, J=6, 13.5 Hz), 2.52 (1H, dd, J=7.5, 13.5 Hz), 2.46–2.35 (3H, m), 2.00 (3H, s), 2.04–1.90 (10H, m), 1.83 (3H, s), 1.61 (3H, s), 1.60 (3H, s), 1.53 (6H, s), 1.24 (2H, m), 1.08 (1H, m), 0.80 (12H, m).

N-Boc-S-all trans-farnesyl-L-cysteine-$^\Psi$($CH_2$—NH)-L-Val-Ile-L-Met or N-Boc-S-all-trans-farnesyl-L-Cys-$^\Psi$($CH_2$—HN)-(SEQ ID NO: 2) Methyl Ester To a mixture of N-Boc-S-all-trans-farnesyl-L-cysteinal (690 mg, 1.69 mmol) and L-Val-L-Ile-L-Met methyl ester hydrochloride (830 mg, 2.01 mmol) in 1% AcOH—MeOH (6.0 mL) was added dropwise a solution of sodium cyanoborohydride (250 mg, 4.02 mmol) in MeOH (3.0 mL) over a 30 min period. The reaction mixture was stirred for an additional 2 h, then concentrated under reduced pressure. The residue was dissolved in saturated aqueous $NaHCO_3$ (20 mL) and extracted with EtOAc (3×50 ml). The combined organic layers were washed with aqueous 5% HCl, and with brine, dried over anhydrous $MgSO_4$, filtered, and evaporated. The residue was purified by normal phase HPLC (Rainin silica, 250×4.6 mm, 1.5 mL/min, hexane/isopropanol/TFA (97:3:0.01), UV detection was at 210 nm). The retention time was 11.80 min.

$^1$H NMR (DMSO-d6, 500 MHz): 8.14 (1H, d, J=8 Hz), 8.12 (1H, d, J=8 Hz), 7.85 (1H, d, J=8.5 Hz), 7.81 (1H, d, J=9.5 Hz), 5.15 (1H, t, J=8 Hz), 5.05 (2H, m), 4.46 (1H, ddd, J=2, 6, 14.5 Hz), 4.39 (1H, dd, J=5.5, 9.5 Hz), 4.33 (1H, ddd, J=5, 10, 14 Hz), 4.23 (1H, dd, J=7, 8.5 Hz), 3.17 (1H, dd, J=8, 14 Hz), 3.12 (1H, dd, J=7.5, 14 Hz), 2.74 (1H, dd, J=6, 13.5 Hz), 2.52 (1H, dd, J=7.5, 13.5 Hz), 2.46–2.35 (3H, m), 2.00 (3H, s), 2.04–1.90 (10H, m), 1.83 (3H, s), 1.61 (3H, s), 1.60 (3H, s), 1.53 (6H, s), 1.24 (2H, m), 1.08 (1H, m), 0.80 (12H, m).

9 N-Boc-S-all-trans-farnesyl-L-Cys-$^\Psi$($CH_2$—NH)-L-Val-L-Ile-L-Met or N-Boc-S-all-trans-farnesyl-L-Cys-$^\Psi$($CH_2$—HN)-(SEQ ID NO: 2)

A mixture of N-Boc-S-all-trans-farnesyl-L-Cys-$^\Psi$($CH_2$—NH)-L-Val-L-Ile-L-Met methyl ester (50 mg, 0.06 mmol) and aqueous barium hydroxide (Serafinowski., 1985) (0.25 M, 200 μL, 4.4 mmol) in MeOH (5.0 mL) was stirred at room temperature for 32 h. The reaction mixture was acidified to pH-2 with aqueous 10% HCl. The solution was extracted with EtOAc (3×40 mL), the combined organic layers were washed with brine, dried over anhydrous $MgSO_4$, filtered, and evaporated. The residue was purified by normal phase HPLC (Rainin silica, 250×4.6 mm, 1.5 mL/min, hexane/isopropanol/TFA (97:3:0.01), UV detection was at 210 nm). The retention time was 21.20 min.

$^1$H NMR (DMSO-d6, 500 MHz): 9.94 (1H, brs), 8.57(1H, brs), 8.37(1H, d, J=7 Hz), 7.86(1H, d, J=8 Hz), 6.68 (1H, d, J=9 Hz), 5.15 (1H, t, J=7.9 Hz), 5.05 (2H, t, J=5.9 Hz), 4.39–4.34(1H. m), 4.22 (1H, t, J=8 Hz), 3.88–3.76 (2H, m), 3.18 (1H, dd, J=13, 8 Hz), 3.11 (1H, dd, J=13, 8 Hz), 2.87 (1H, brs), 2.89 (1H, brs), 2.52 (2H, d, J=7 Hz), 2.28–2.16 (1H, m), 2.06–1.92 (6H, m), 1.94–1.88 (2H, m), 1.86–1.80 (1H, m), 1.61 (3H, s), 1.59 (3H, s), 1.53 (6H, s), 1.44–1.40 (1H, m), 1.35 (9H, s), 1.12–1.04 (1H, m), 1.15 (3H, t, J=7 Hz), 0.84–0.77 (12, m).

N-Boc threo-4-hydroxy-5-(s-all-trans-farnesyl)thiomethyl-pyrrolidin-2-one

To a solution of N-Boc-S-all-trans-farnesyl cystein (1.54 g, 3.62 mmol) in DCM (40 mL) was added Meldrum's acid (Jouin et al., 1987) (cycloisopropylidene malonate, 575 mg, 3.99 mmol) and dimethylaminopyridine (DMAP, 1.02 g, 8.34 mmol). The mixture was cooled at −5° C., and a solution of isopropenyl chloroformate (IPCF, 435 μL, 480 mg, 3.92 mmol) in DCM (5.0 mL) was added dropwise with stirring. The mixture was stirred for 5 h. The reaction was quenched with cold 5% aqueous potassium bisulfate (25 mL), the organic layer separated, washed with bine, dried over anhydrous $MgSO_4$, filtered, and evaporated. The residue was dissolved in EtOAc (50 mL) and heated at reflux for 1 h. The solvent was evaporated and the residue dissolved in DCM:AcOH (10:1, 30 mL). The mixture was cooled to 0° C., and sodium borohydride (252 mg, 6.69 mmol) was added in one portion. The mixture was stirred at room temperature for 6 h. The reaction was quenched with water (10 mL), the organic layer separated, and washed with brine, dried over anhydrous $MgSO_4$, filtered, and evaporated. The residue was purified by silica gel chromatography (hexane/EtOAc 80:20, 70:30) to provide the title compound (642 mg).

$^1$H NMR ($CDCl_3$): 5.26 (1H, t, J=8 Hz), 5.09 (2H, brs), 4.62 (1H, brd, J=6.5 Hz), 4.31 (1H, ddd, J=2.5, 8.5, 15.5 Hz), 3.25 (2H, dd, J=4, 7 Hz), 3.07 (1H, dd, J=3, 13 Hz), 2.89 (1H, dd, J=10, 13 Hz), 2.77 (1H, dd, J=7.5, 17.5 Hz), 2.66 (1H, dd, J=7, 17,5 Hz), 2.57 (1H, brd, J=3 Hz), 2.12=1.94 (8H, m), 1.68 (6H, s), 1.59 (6H, s), 1.53 (9H, s).

(3S,4S)-N-Boc-4-amino-3-hydroxy-5-(S-all-trans-farnesyl)-pentanoic acid

To a solution of N-Boc threo-4-hydroxy-5-(S-all-trans-farnesyl)thiomethyl-pyrrolidin-2-one (470 mg) in acetone (10 mL) was added 1N sodium hydroxide (2.0 mL) at 0° C. The mixture was stirred at 0° C. for 1 h, then acidified to pH=6 with aqueous 10% HCl. The solvent was evaporated and the residue extracted with EtOAc (3×30 mL). The combined organic layers were washed with brine, dried over anhydrous $MgSO_4$, filtered, and evaporated. The residue was purified by silica gel chromatography (hexane/acetone 80:20) to give the title compound (370 mg).

$^1$H NMR ($CDCl_3$, 500 MHz): 5.23 (1H, t, J=8 Hz), 5.09 (1H, t, J=7 Hz), 5.01 (1H, d, J=9.5 Hz), 4.35 (1H, d, J=10 Hz), 3.66 (1H, dd, J=7, 15 Hz), 3.19 (2H, d, J=8 Hz), 2.71 (1H, dd, J=8, 13.5 Hz), 2.64 (2H, m), 2.53 (1H, dd, 3, 16.5 Hz), 2.12–1.95 (8H, m), 1.67 (3H, s), 1.66 (3H, s), 1.59 (6H, s), 1.55 (9H, s).

(3S,4S)-N-Boc-4-amino-3-hydroxy-5-(s-all-trans-farnesyl)-1-(L-isoleucine-L-methionine)pentanoic amide A solution of (3S,4S)-N-BOc-4-amino-3-hydroxy-5-(S-all-trans-farnesyl)-1-(methyl L-isoleucine-L-methionine)-pentanoic amide (53 mg) and aqueous 10% sodium carbonate in CH₃OH:CH₃CN (1:1, 10 mL) was stirred at room temperature for 16 h. The reaction mixture was acidified to pH-2 with aqueous 10% HCl, extracted with EtOAc (3×40 mL). The combined organic layers were washed with brine, drived over anhydrous MgSO₄, filtered and evaporated. The residue was separated by silica gel chromatography (hexane/acetone 70:30, hexane/acetone/methanol 70:30:10) to give the title compound as a white solid (40 mg): ¹HNMR (DMSO-d6): 7.50 (1H, brs), 6.34 (1H, brs), 5.16 (1H, t, J=8 Hz), 5.04 (2H, dd, J=6, 11.5 Hz), 4.10 (1H, dd, J=6.5, 8.5 Hz), 3.92 (1H, s), 2.49 (1H, dd, J=7, 15 Hz), 3.15 (2H, dd, J=4.5, 6.5 Hz), 2.60 (1H, dd, J=6, 14 Hz), 2.37 (3H, m), 1.96 (3H, s), 2.04–1.89 (10H, m), 1.81 (1H, m), 1.61 (3H, s), 1.60 (2H, s), 1.54 (6H, s), 1.41 (1H, m), 1.32 (9H, brs), 1.08 (1H, m), 0.80 (3H, d, J=6.5 Hz), 0.77 (3H, t, J=7.5 Hz).

(3S,4S)-N-Boc-4-amino-3-hydroxy-5-(s-all-trans-farnesyl)-1-(methyl Ile-Met)pentanoic amide To a mixture of (3S,4S)-N-Boc-4-amino-3-hydroxy-5-(S-all-trans-farnesyl)-pentanoic acid (185 mg, 0.394 mmol), L-Ile-L-Met methyl ester hydrochloride (231 mg, 0.592 mmol), 1-hydroxybenzotriazole monohydrate (80 mg, 0.59 mmol) and N-methylmorpholine (65 µL, 60 mg, 0.59 mmol) in DMF (10 mL) at 0° C. was added 1-ethyl-3-(3-dimethylamino-propyl)carbodiimide hydrochloride (98 mg, 0.51 mmol) in one portion. The mixture was stirred at 0° C. for 2 h, then at room temperature for 46 h. The reaction was quenched with water (20 mL) and extracted with EtOAc (3×40 mL). The combined organic layer were washed with aqueous 10% HCl, saturated NaHCO₃, brine, dried over anhydrous MgSO₄, filtered, and evaporated. The residue was purified by silica gel chromatography (hexane/acetone 70:30, 60:40) to give the title compound (188 mg, 66%). ¹H NMR (CDCl₃, 500 MHz): 6.93 (1H, d, J=8 Hz), 6.66 (1H, d, J=8.5 Hz), 5.22 (1H, t, J=8 Hz), 5.08 (2H, t, J=4.5 Hz), 5.04 (1H, d, J=9.5 Hz), 4.70 (1H, dd, J=7.5, 12.5 Hz), 4.32 (1H, t, J=6.5 Hz), 4.27 (1H, brd, J=9 Hz), 4.18 (1H, s), 3.74 (2H, s), 3.64 (1H, dd, J=8, 15.5 Hz), 3.17 (2H, dd, J=4.5, 6.5 Hz), 2.71 (1H, dd, J=8, 13.5 Hz), 2.64 (1H, dd, J=6, 13.5 Hz), 2.50 (2H, t, J=7 Hz), 2.47 (1H), 2.34 (1H, dd, J=3, 16 Hz), 2.08 (2H, s), 2.17–1.94 (10H, m), 1.87 (2H, m), 1.66 (3H, s), 1.65 (3H, s), 1.58 (6H, s), 1.52 (1H, m), 1.44 (9H, s), 1.15 (1H, m), 0.92 (3H, d, J=6.5 Hz), 0.90 (3H, t, J=8 Hz).

(3S,4S)-N-Boc-4-amino-3-hydroxy-5-(S-all-trans-farnesyl)-1-(methyl L-Val-L-Ile-L-Met)pentanoic Amide To a mixture of (3S,4S)-N-Boc-4-amino-3-hydroxy-5-(S-all-trans-farnesyl)-pentanoic acid (185 mg, 0.394 mmol), L-Val-L-Ile-L-Met methyl ester hydrochloride (289 mg, 0.592 mmol), 1-hydroxybenzotriazole monohydrate (80 mg, 0.59 mmol) and N-methylmorpholine (65 µl, 60 mg, 0.59 mmol) in DMF (10 mL) at 0° C. was added 1-ethyl-3-(3-dimethylaminopropyl)carbodiimide hydrochloride (98 mg, 0.51 mmol) in one portion. The mixture was stirred at 0° C. for 2 h, then at room temperature for 25 h. The reaction was quenched with water (20 mL) and extracted with EtOAc (3×40 mL). The combined organic layer were washed with aqueous 10% HCl, saturated NaHCO₃, brine, dried over anhydrous MgSO₄, filtered, and evaporated. The residue was purified by silica gel chromatography (hexane/acetone 70:30, 60:40, 50:50) to give the title compound (228 mg, 70%).

¹H NMR (CDCl₃, 500 MHz): 7.42 (1H, brs), 7.20 (1H, brs), 7.16 (1H, brs), 5.23 (1H, t, J=7 Hz), 5.10 (2H, t, J=5 Hz), 4.74 (1H, ddd, J=4.5, 7.5, 12.5 Hz), 4.43 (2H, m), 4.26 (1H, d, J=10 Hz), 3.75 (3H, s), 3.60 (1H, dd, 8, 15 Hz), 3.17 (2H, t, J=7.5 Hz), 2.72 (1H, dd, J-8, 14 Hz), 2.64 (1H, dd, 6, 14 Hz), 2.53 (1H, dd, J-9.5, 14.5 Hz), 2.47 (2H, t, J=7 Hz), 2.42 (1H), 2.05 (3H, s), 2.16–1.96 (13H, m), 1.82 (1H, m), 1.67 (3H, s), 1.65 (3H, s), 1.59 (3H, s), 1.58 (3H, s), 1.53 (1H, m), 1.43 (9H, s), 1.10 (1H, m), 0.90 (12H, m).

(3S,4S)-N-Boc-4-amino-3-hydroxy-5-(S-all-trans-farnesyl)-1-(L-Val-L-Ile-L-Met)pentanoic Amide A mixture of (3S,4S)-N-Boc-4-amino-3-hydroxy-5-(S-all-trans-farnesyl)-1-(methyl L-Val-L-Ile-L-Met)pentanoic amide (228 mg) and 10% Na₂CO₃ (20 mL) in CH₃OH:CH₃CN (1:1, 10 mL) was stirred at room temperature for 40 h. The reaction mixture was acidified to pH=2 with aqueous 10% HCl. The solution was extracted with EtOAc (3×40 mL and the combined organic layers were washed with brine, dried over anhydrous MgSO₄, filtered, and evaporated. The residue was separated by silica gel chromatography (hexane/acetone 70:30, hexane/acetone/methanol 70:30:10) to give the title compound (174 mg) as a white solid.

¹H NMR (DMSO-d6, 500 MHz): 7.92 (1H, d, J=8 Hz), 7.82 (1H, d, J=7 Hz), 7.40 (1H, brs), 6.40 (1H, d, J=9 Hz), 5.15 (1H, t, J=8 Hz), 5.04 (1H, dd, J=6.5, 12.5 Hz), 4.91 (1H, brs), 4.22 (1H, t, J=8 Hz), 4.10 (1H, t, J=8 Hz), 3.94 (1H, brs), 3.88 (1H, s), 3.51 (1H, dd, J=9, 16 Hz), 3.10 (2H, d, J=6.5 Hz), 2.59 (1H, dd, J=5, 13 Hz), 2.32 (3H, m), 1.95 (3H, s), 2.12=1.88 (10H, m), 1.74 (3H, m), 1.61 (3H, s), 1.59 (3H, s), 1.53 (6H, s), 1.40 (1H, m), 1.36 (9H, s), 1.04 (1H, m), 0.79 (12H, m).

(4S)-N-Boc-4-amino-2-difluoro-3-hydroxy-5-(S-all-trans-farnesyl)-pentanoate Ethyl Ester To a suspension of zinc dust (764 mg, 11.7 mmol) in anhydrous THF (30 mL) was added one crystal of I₂ (Doherty et al., 1992). The reaction mixture heated to reflux and ethyl bromodifluoroacetate (100 µL) was added to initiate the reaction. After 2 min, a mixture of the N-BOc-S-all-trans-farnesyl-L-cysteinal (2.42 g, 5.86 mmol), ethyl bromodifluoroacetate (1.12 mL, 1.79 g, 8.83 mmol) in THF (15 mL) was added at such a rate as to control the reflux (as rapidly as possible). After heating at reflux for 30 minutes, the mixture was allowed to cool, then partitioned between EtOAc (100 mL) and aqueous 1M KHSO₄ (100 mL). The organic layer was separated, and the aqueous phase extracted with EtOAc (2×100 mL). The combined organic layers were washed with brine, dried over anhydrous MgSO₄. After concentration, the residue was purified by repeated silica gel chromatography (hexane/EtoAc 90:10, 85:15) to provide (N-Boc-S-all-trans-farnesyl)-L-cysteine methyl ester (844 mg), N-Boc-S-all-trans-farnesyl-L-cysteinol (1, 141 mg), and (4S)-N-Boc-4-amino-2,2-difluoro-3-hydroxy-5-(S-all-trans-farnesyl)pentanoic ethyl ester (531 mg).

N-Boc-S-all-trans-farnesyl-L-cysteinol

¹H NMR (CDCl₃, 500 MHz): 5.24 (1H, t, J=8 Hz), 5.09 (2H, t, J=7 Hz), 4.99 (1H, brs), 3.74 (3H, m), 3.18 (2H, dd, J=2, 8 Hz), 2.68 (1H, dd, J=6, 13 Hz), 2.63 (1H, dd, J=7, 13 Hz), 2.07 (6H, m), 1.97 (2H, t, J=8 Hz), 1.68 (3H, s), 1.67 (3H, s), 1.60 (6H, s), 1.45 (9H, s).

(4S)-N-Boc-4-amino-2-difluoro-3-hydroxy-5-(S-all-trans-farnesyl)pentanoate ethyl ester ¹H NMR (CDCl₃, 500 MHz): 5.24 (1H, t, J=7 Hz), 5.09 (2H, t, J=5.5 Hz), 5.04 (1H, brs), 4.35 (3H, m), 3.95 (1H, dd, J=7, 14 Hz), 3.87 (1H, brs), 3.20 (2H, dd, J-3, 8 Hz), 2.77 (2H, brs), 2.06 (6H, m), 1.96 (2H, t, J=8 Hz), 1.67 (6H, s), 1.59 (6H, s), 1.43 (9H, s), 1.36 (3H, t, J-7 Hz).

(4S)-N-Boc-4-amino-2,2-difluoro-3-hydroxy-5-(S-all-trans-farnesyl)-pentanoic acid A mixture of (4S)-N-Boc-4-amino-2,2-difluoro-3-hydroxy-5-(S-all-trans-farnesyl)pentanoate ethyl ester (141 mg) and aqueous 5% KOH in methanol (5.0 mL) was stirred at 0° C. for 2 h. The reaction was acidified to pH=2 with aqueous 10% HCl, and extracted with EtOAc (3×50 mL). The combined organic layers were washed with aqueous 10% HCl, brine, dried over anhydrous MgSO$_4$, filtered, and evaporated. The residue was purified by silica gel chromatography (hexane/EtOAc 80:20) to provide the title compound (131 mg).

$^1$H NMR (DMSO-d6, 500 MHz): 5.17 (1H, t, J=7 Hz), 5.05 (2H, t, J=5 Hz), 4.18 (1H, dd, J=7, 14 Hz), 3.87 (1H, t, J=5 Hz), 3.14 (2H, d, J=6 Hz), 2.55 (1H, dd, J=6, 13 Hz), 2.46 (1H, dd, J=8, 13 Hz), 2.04 (6H, m), 1.92 (2H, t, J=7 Hz), 1.68 (3H, s), 1.67 (3H, s), 1.57 (6H, s), 1.38 (9H, s).

(4S)-N-Boc-4-amino-2,2-difluoro-3-hydroxy-5-(S-all-trans-farnesyl)-1-(methyl L-Ile-L-Met)pentanoic Amide A mixture of (4S)-N-Boc-4-amino-2,2-difluoro-3-hydroxy-5-(S-all-trans-farnesyl)pentanoic acid (233 mg, 0.46 mmol), l-Ile-L-Met methyl ester hydrochloride (270 mg, 0.69 mmol), 1-hydroxybenzotriazole monohydrate (93 mg, 0.69 mmol) and N-methylmorpholine (76 µL, 70 mg, 0.69 mmol) in DMF (10 mL) at 0° C. was added 1-ethyl-3-(3-dimethylaminopropyl)carbodiimide hydrochloride (106 mg, 0.55 mmol) in one portion. The mixture was stirred at 0° C. for 2 h, then at room temperature for 13 h. The reaction was quenched with water (20 mL) and mixture extraced with EtOAc (3×50 mL). The combined organic layers were washed with aqueous 10% HCl, saturated NaHCO$_3$, brine, dried over anhydrous MgSO$_4$, filtered, and evaporated. The residue was purified by silica gel chromatography (hexane/EtOAc 85:15) to give the title compound (155 mg, 44%).

$^1$H NMR (CDCl$_3$, 500 MHz): 7.23 (1H, d, J=5.5 Hz), 7.18 (1H, d, J=8 Hz), 5.28 (1H, d, J=8.5 Hz), 5.22 (1H, t, J=8 Hz), 5.08 (2H, t, J=7 Hz), 4.71 (1H, dd, J=5, 13 Hz), 4.41 (1H, m), 4.34 (1H, t, J=6 Hz), 4.07 (1H, brs), 3.99 (1H, dd, J=7, 14 Hz), 3.73 (3H, s), 3.18 (2H, dd, J=3, 8 Hz), 2.80 (1H, dd, J=5.5, 12.5 Hz), 2.72 (1H, dd, J=7.5, 12.5 Hz), 2.51 (2H, t, J=7 Hz), 2.07 (3H, s), 2.19–1.93 (10H, m), 1.81 (1H, brs), 1.67 (3H, s), 1.65 (3H, s), 1.59 (6H, s), 1.53 (1H, m), 1.43 (9H, s), 1.18 (1H, m), 0.94 (6H, m).

(4S)-N-Boc-4-amino-2,2-difluoro-3-hydroxy-5-(S-all-trans-farnesyl)-1-(methyl L-Val-L-Ile-L-Met)pentanoic Amide A mixture of (4S)-N-Boc-4-amino-2,2-difluror-3-hydroxy-5-(S-all-trans-farnesyl)pentanoic acid (277 mg, 0.55 mmol), L-Val-L-Ile-L-Met methyl ester hydrochloride (402 mg, 0.82 mmol), 1-hydroxybenzotriazole monohydrate (111 mg, 0.82 mmol) and N-methylmorpholine (90 µl, 83 mg, 0.82 mmol) in DMF (8.0 mL) at 0° C. was added 1-ethyl-3-(3-dimethylaminopropyl)-carbodiimide hydrochloride (126 mg, 0.66 mmol) in one portion. The mixture was stirred at 0° C. for 2 h, then at room temperature for 21 h. The reaction was quenched with water (20 mL) and extracted with EtOAc (3×50 mL). The combined organic layers were washed with aqueous 10% HCl, saturated NaHCO$_3$, brine, dried over anhydrous MgSO$_4$, filtered, and evaporated. The residue was purified by silica gel chromatography (hexane/acetone 90:10, 85:15) to give the title compound (90 mg, 19%).

$^1$H NMR (CDCl$_3$, 500 MHz): 7.28 (1H, d, J-7 Hz), 7.18 (1H, d, J-9 Hz), 6.85 (1H, s), 5.32 (1H, d, J=7.5 Hz), 5.23 (1H, t, J=6.5 Hz), 5.08 (2H, s), 4.69 (1H, ddd, J=5, 8, 12.5 Hz), 4.35 (3H, m), 3.98 (1H, brd, J=5 Hz), 3.74 (3H, s), 3.19 (2H, d, J=7 Hz), 2.80 (1H, dd, J=6, 13 Hz), 2.73 (1H, dd, J=7, 13 Hz), 2.49 (2H, t, J=8 hz), 2.07 (3H, s), 2.25–194 (11H, m), 1.89 (1H, m), 1.67 (6H, s), 1.60 (6H, s), 1.51 (1H, m), 1.43 (9H, s), 1.15 (1H, m), 0.92 (12H, m).

(4S)-N-Boc-4-amino-2,2-difluoro-3-hydroxy-5-(S-all-trans-farnesyl)-1-(L-Ile-L-Metpentanoic Amide A mixture of (4S)-N-Boc-4-amino-2,2-difluoro-3-hydroxy-5-(S-all-trans-farnesyl)-1-(methyl L-Ile-L-Met) pentanoic amide (155 mg, 0.21 mmol) and aqueous 10% sodium carbonate (10 mL) in CH$_3$CN:CH$_3$OH (1:1, 10 mL) was stirred at room temperature for 36 h. The mixture was acidified to pH=2 with aqueous 10% HCl. The mixture was extracted with EtOAc (3×50 mL) and the combined organic layers were washed with aqueous 10% HCl, brine, dried over anhydrous Na$_2$SO$_4$, filtered, and evaporated. The residue was purified by silica gel chromatography (hexane/acetone 70:30, 50:50, acetone, methanol) to give the title compound (90 mg, 59%) as a solid.

$^1$HNMR (DMSO-d6, 500 MHz): 6.26 (1H, d, J=9 Hz), 5.15 (1H, t, J=8 Hz), 5.04 (2H, brd, J=6 Hz), 4.13 (3H, m), 3.92 (1H, dd, J=8, 16 Hz), 3.14 (2H, m), 2.54 (1H, dd, J=8, 13.5 Hz), 2.44 (1H, dd, J=7, 13.5 Hz), 2.41 (2H, t, J=8 Hz), 1.98 (3H, s), 2.05–1.78 (11H, m), 1.61 (6H, s), 1.53 (6H, s), 1.46 (1H, m), 1.34 (9H, s), 1.06 (1H, m), 0.84 (3H, d, J=7 Hz), 0.79 (3H, t, J=7 Hz).

(4S)-N-Boc-4-amino-2,2-difluoro-3-hydroxy-5-(S-all-trans-farnesyl)-1-(L-Val-L-Ile-L-Met)pentanoic Amide A mixture of (4S)-N-Boc-4-amino-2,2-difluoro-3-hydroxy-5-(S-all-trans-farnesyl)-1-(methyl L-Val-L-Ile-L-Met)pentanoic amide (90 mg) and aqueous 10% sodium carbonate (10 mL) in CH$_3$CN:CH$_3$OH (1:1, 10 mL) was stirred at room temperature for 60 h. The mixture was acidified to pH=2 with aqueous 10% HCl. The mixture was extracted with EtOAc (3×50 mL) and the combined organic layers were washed with aqueous 10% HCl, brine, dried over anhydrous Na$_2$SO$_4$, filtered, and evaporated. The residue was purified by silica gel chromatography (hexane/acetone 70:30, 50:50, acetone, methanol) to give the title compound (35 mg, 40%) as a solid.

$^1$H NMR (DMSO-d6, 500 MHz): 7.25 (2H, brs), 6.65 (2H, brs), 5.15 (1H, t, J=7 Hz), 5.04 (2H, t, J=5 Hz), 4.22 (1H, d, J=8 Hz), 4.16 (1H, dd, J=8, 21.5 Hz), 4.12 (1H, d, J=6.5 Hz), 3.91 (1H, t, J=9 Hz), 3,89 (1H, brs), 3.13 (2H, m), 2.54 (1H, dd, J=9, 13.5 Hz), 2.43 (1H, dd, J=7, 13.5 Hz), 2.35 (3H, m), 1.95 (3H, s), 2.07–1.88 (10H, m), 1.76 (1H, m), 1.61 (6H, s), 1.53 (6H, s), 1.41 (1H, m), 1.35 (9H, s), 1.08 (1H, m), 0.84 (3H, d, J=6.5 Hz), 0.08 (9H, m).

To further establish the specificity of the inactivation process, several commercially available haloketones were studies as putative inactivators of the endoprotease. The structures of these analogs are shown and their activities are shown in Table V. In these studies, the solubilized protein material was preincubated with a chloromethyl ketone inhibitor at 284 µM (unless otherwise noted) for 30 minutes;

then 2.5-μL aliquots of the incubated solution were taken and diluted 20-fold for assay of the residual enzyme activity. Of the chloromethyl ketone inhibitors tested, 2-Nal-Ala-CMK has a similar inhibitory potency to that of TPCK (Table IV). Save for the dipeptide derivatives (ZGGFCMK and ZAPFCMK) derived from TPCK, the other halomethyl ketones tested are virtually inert. In aggregate, these data demonstrate that the inactivation of the endoprotease by TPCK and BFCCMK is specific in nature.

Syntheses of Halomethylketone Endoprotease Inhibitors

S-all-trans-Farnesyl-L-cysteine, $\underline{N}$-Boc-S-all-trans-farnesyl-L-cysteine and $\underline{S}$-all-trans-farnesyl-L-cysteine methyl ester were prepared as reported (Ma et al., 1993, 1994). Nα-Biotinyl-Nα-tosyl-L-Lysine chloromethyl ketone (BTLCK) was prepared from (+)-biotin 4-nitrophenyl ester and Nα-tosyl-L-lysine chloromethyl ketone by the conventional solution peptide coupling method (Bodanszky & Bodanszky, 1994). The procedures for the preparations and the properties of the S-farnesylated inhibitors are given below. The overall synthetic schemes for BFCCMK and GGFCCMK are also shown below.

N-Boc-S-all-trans-Farnesyl-L-cysteine Diazomethyl Ketone (2) was prepared from N-Boc-S-all-trans-farnesyl-L-cysteine (1) (3.47 g, 8.15 mmol), NMM (0.9 mL, 824 mg, 8.15 mmol), and isobutyl chloroformate (1.06 mL, 1.113 g, 8.15 mmol), and isobutyl chloroformate (1.06 mL, 1.113 g, 8.15 mmol) in 30 mL of dry THF at −20° C. with stirring for 30 min, followed by the addition of ethereal diazomethane by the method of Green and Shaw (1981). The crude product was purified on a silica gel column (hexane/ethyl acetate, 90:10, v/v) to give a yellowish oil (2.35 g, 64%). $R_f$=0.58 (hexane/ethyl acetate, 2:1, v/v).

$^1$H NMR (CDCl$_3$, 500 MHz): 5.59 (1H, brs, COCH$\underline{N}_2$), 5.34 (1H, brs, NH), 5.22 (1H, t, J=7 Hz), 5.08 (2H, s), 4.29 (1H, brs, α-H), 3.18 (2H,m), 2.80 (2H,m), 1.96–2.06 (8H, m), 1.64 (6H,s), 1.58 (6H,s), 1.44 (9H,s). HRCIMS (NH$_3$ gas): 467.3056 (M+NH$_4^+$, calcd. for C$_{24}$H$_{39}$N$_3$O$_3$S, N-Boc-S-all-trans-Farnesyl-L-cysteine Chloromethyl Ketone (BFCCMK)

Was prepared from the diazomethyl ketone 2 (1.00 g, 2.22 mmol) in 20 mL of dry THF and ethereal hydrogen chloride (4.44 mL, 4.44 mmol) at room temperature by the method of Kettner and Shaw (1981). The crude product was purified on a silica gel column (hexane/ethyl acetate, 90:10, v/v) to give a yellowish oil (902 mg, 89%). $R_f$=0.65 (hexane/ethyl acetate, 2:1, v/v). $^1$H NMR (CDCl$_3$, 500 MHz): 5.30 (1H, brs, NH), 5.20 (1H, t, J=7 Hz), 5.08 (2H, t, J=5.5 Hz), 4.59 (1H, dd, J=5, 7.5 Hz, α-H), 4.34 (2H, s, COCH$_2$Cl), 3.17 (2H, m), 2.90 (1H, dd, J=5.5, 14 Hz), 2.82 TH, dd, J=6.5, 14 Hz), 2.12–1.94 (8H, m), 1.67 (6H, s), 1.59 (6H, s), 1.44 (9H, s). HRCIMS (NH$_3$ gas): 475.2961 (M+NH$_4^+$, calcd. for C$_{24}$H$_{40}$NO$_3$SCI, 457.2415, 8%), 439 (M+NH$_4^+$−Cl, 65%), 422 (M$^+$−Cl, 60%), 205 (100%).

N-Benzyloxycarbonylglycylglycyl-S-all-trans-farnesyl-L-cysteine Methyl Ester (5) was prepared from S-all-trans-farnesyl-L-cysteine methyl ester (4) (1.69 g, 4.75 mmol) and Z-Gly-Gly-OH (1.26 g, 4.75 mmol) by the conventional solution peptide coupling method (Bodanszky & Bodanszky, 1994). The crude product was purified on a silica gel column (hexane/acetone, 70:30<50:50, v/v) to give an oil (2.386 g, 86%). $R_f$=0.52 (hexane/acetone 1:1). $^1$H NMR (CDCl$_3$, 500 MHz):

7.34 (5H, m), 6.84 (1H, m, NH), 5.53 (1H, brs, NH), 5.18 (1H, t, J=7.5 Hz), 5.12 (2H, s), 5.08 (2H, t, J=6.5 Hz), 4.75 (1H, dd, J=6.5, 12.5 Hz), 4.02 (2H, m), 2.91 (2H, brs), 3.74 (3H,s), 3.18 (1H, dd, J=5, 15.5 112) 3.10 (1H, dd, J=7.5 7.5 Hz), 2.94 (1H, dd, J=5, 14.5 Hz), 2.83 (1H, dd, J=6, 14.5 Hz), 2.12–1.95 (8H, m), 1.67 (3H, s), 1.65 (3H,s), 1.59 (6H,s).

N-Benzyloxycarbonylglycylglycyl-S-all-trans-farnesyl-L-cysteine (6) was prepared by saponification of the methyl ester 5 (1.64 g, 2.79 mmol) with 40 mL of 10% solium carbonate/acetonitrile (1/1, v/v) with stirring at room temperature for 40 h. HCl (5%) was added to the mixture until pH 3 and then extracted with ethyl acetate (3×60 mL). The combined organic layer was washed with 5% HCl, with saturated solium bicarbonate, and with brine and then dried and evaporated to give a white solid (1.50 g, 94%). $R_f$=0.05 (hexane/acetone, 1:2, v/v). $^1$H NMR (DMSO-d$_6$, 500 MHz): 8.21 (1H, d, J=8 Hz, NH), 8.06 (1H, t, J=5.5 Hz), 7.48 (1H, t, J=6 Hz), 7.74 (3H, s), 7.29 (1H, brs), 5.14 (1H, t, J=7.5 Hz), 5.05 (2H, m), 5.01 (2H, s), 4.39 (1H, dd, J=6.5, 12.5 Hz), 3.75 (2H, brs), 3.64 (2H, d, J=5.5 Hz), 3.17 (1H, dd, J=8.5 13.5 Hz), 3.10 (1H, dd, J=7.5, 13.5 Hz), 2.80 (1H, dd, J=4.5, 13.5 Hz), 2.63 (1H, dd, J=8, 13.5 Hz), 2.40–1.88 (8H, m), 1.61 (3H, s), 1.60 (3H, s), 1.53 (6H, s).

N-Benzyloxycarbonylglycylglycyl-S-all-trans-farnesyl-L-cysteine Diazomethyl Ketone (7) was prepared from 6 (2.23 g, 3.90 mmol) by the same method as previously described for 2. The crude material was purified on a silica gel column (hexane/acetone 70:30, 60:40, 50:50, v/v) to give a yellowish gel (922 mg, 40%). $R_f$=0.70 (hexane/acetone 1:1, v/v). $^1$H NMR (CDCl$_3$, 500 MHz): 7.35 (5H, s), 7.03 (1H, d, J=6.5 Hz, NH), 6.85 (1H, brs, COCH$\underline{N}_2$), 5.54 (1H, brs, NH), 5.20 (1H, t, J=8 Hz), 5.12 2H, s), 5.08 (2H, t, J=4.5 Hz), 4.58 (1H, brs, α-H), 3.99 (2H, m), 3.88 (2H, d, J=4 Hz), 3.20 (1H, dd, J=9, 13.5 Hz), 3.13 (1H, dd, J=7, 13.5 Hz), 2.91 (1H, dd, J=4.5, 13.5 Hz), 2.78 (1H, dd, J=7, 13.5 Hz), 2.12–1.95 (8H, m), 1.67 (3H, s), 1.66 (3H, s), 1.59 (6H, s). HRFABMS: 620.2883 (M+Na$^+$, calcd. for C$_{31}$H$_{43}$N$_5$O$_5$SNa, 620.2880, 95%).

N-Benzyloxycarbonylglycylglycyl-S-all-trans-farnesyl-L-cysteine Chloromethyl Ketone (ZGGFCCMK)

was synthesized from 7 (900 mg, 1.51 mmol) by the same method described for BFCCMK. The crude product was purified on a silica gel column (hexane/acetone, 70:30, 60:40, 50:50, v/v) to give a yellowish solid (585 mg, 64%). $R_f$=0.75 (hexane/acetone, 1:1, v/v). $^1$H NMR (CDCl$_3$, 500 MHz): 7.35 (5H, s), 7.10 (1H, d, J=5.5 Hz, NH), 6.84 (1H, t, J=5.5 Hz, NH), 5.54 (1H, t, J=3.5 Hz, NH), 5.19 (1H, t, J=8 Hz), 5.12 (2H, s), 5.08 (2H, t, J=6 Hz), 4.83 (1H, dd, J=7, 13.5 Hz, α-H), 4.34 (2H, s, COCH$_2$Cl), 4.00 (2H, brs), 3.87 (2H, d, J=4.5 Hz), 3.19 (1H, dd, J=5.5, 14 Hz), 2.79 (1H, dd, J=7, 14 Hz), 2.12–1.95 (8H, m), 1.67 (3H, s), 1.66 (3H, s), 1.59 (6H, s). HRFABMS: 628.2588 (M+Na$^+$, cacld, for C$_{21}$H$_{44}$N$_3$O$_5$SCINa, 628.2588, 94%.

Inhibition of the Enzyme by Non-Halomethyl Ketone Inhibitors

An aliquot (1–5 μL) of the enzyme preparation was diluted with buffer D to 47 μL at 4° C. An inhibitor solution (1 μL) in DMSO was added, and the reaction solution was mixed well at time zero. After the reaction mix was incubated at 37° C. for 30 min. The residual enzyme activity was assayed as described above.

Inhibition of the Endoprotease Activity by Chloromethyl Ketones

One possible approach to identifying the endoprotease is the specific affinity labeling of the endoprotease. During the characterization of the solubilized enzyme, it was found that Nα-tosyl-L-Phenylalanine chloromethyl ketone (TPCK), a classic affinity irreversible inhibitor of the serine protease α-chymotrypsin, irreversibly inhibited the endoprotease activity with $K_{inh}K_1=77/\pm0.6)\times10^{-3}$ $S^{-1}$ (FIG. 16A), while Nα-tosyllysine chloromethyl ketone (TLCK), a specific irreversible inhibitor of trypsin and trypsin-like enzymes, did not inhibit the enzyme activity under the same conditions (FIG. 16B) (Chen, 1995).

The specificity of the inhibition of the endoprotease by TPCK was further explored. The finding that the inhibition with TPCK obeyed saturation kinetics (FIG. 16A) and that the chemically similar TLCK did not inactivate the enzyme already strongly suggests that the inhibition mechanism is specific in nature. The irreversible inhibition of the endoprotease activity by TPCK was blocked by the endoprotease-specific reversible inhibitor RPI. The enzyme activity was prevented from inhibition by 82% in the presence of 500 nM RPI, a potent competitive inhibitor of the endoprotease, shown above. However, if the enzyme was preincubated with TPCK first, and then 500 nM RPI was added, no enzyme activity was regenerated from the inhibited enzyme. The enzyme activity was not regenerated after a gel filtration chromatography of the inhibited enzyme solutions, which were preincubated with TPCK at different times, and after a 24-h dialysis of the inhibited enzyme solutions. The data presented above support the view that TPCK is a specific active-site-directed irreversible inhibitor for this endoprotease leading to other potent chloromethyl ketone inhibitors.

Figure 17A:
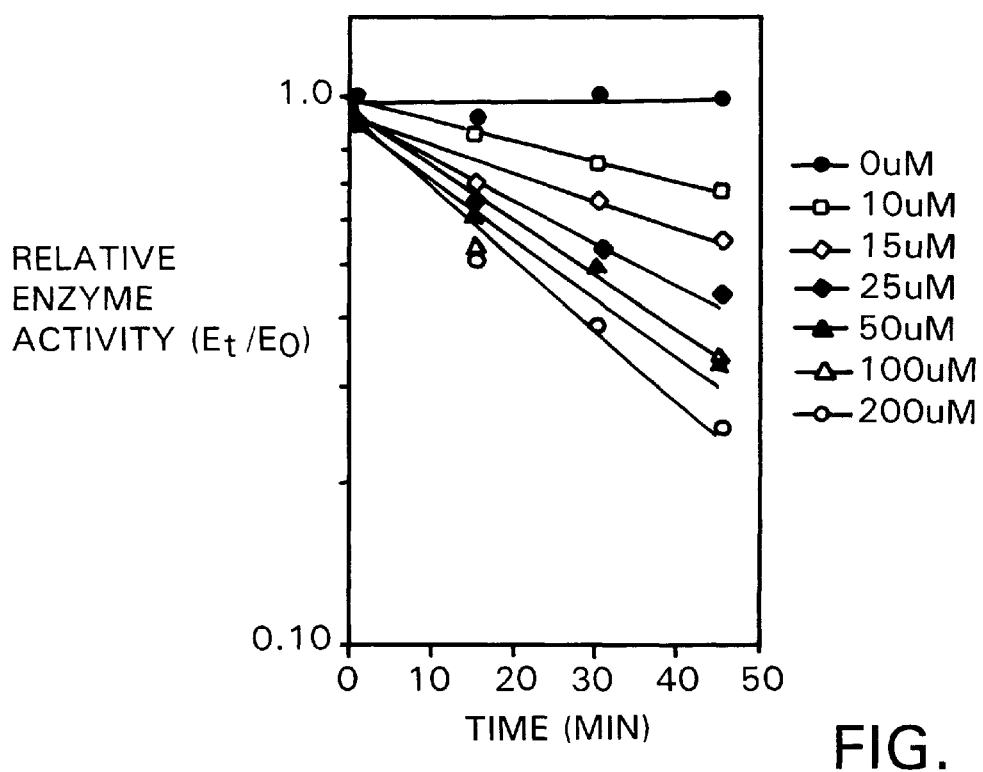
FIGS. 17A and 17B illustrate inhibition of the enzyme.
Figure 17B:
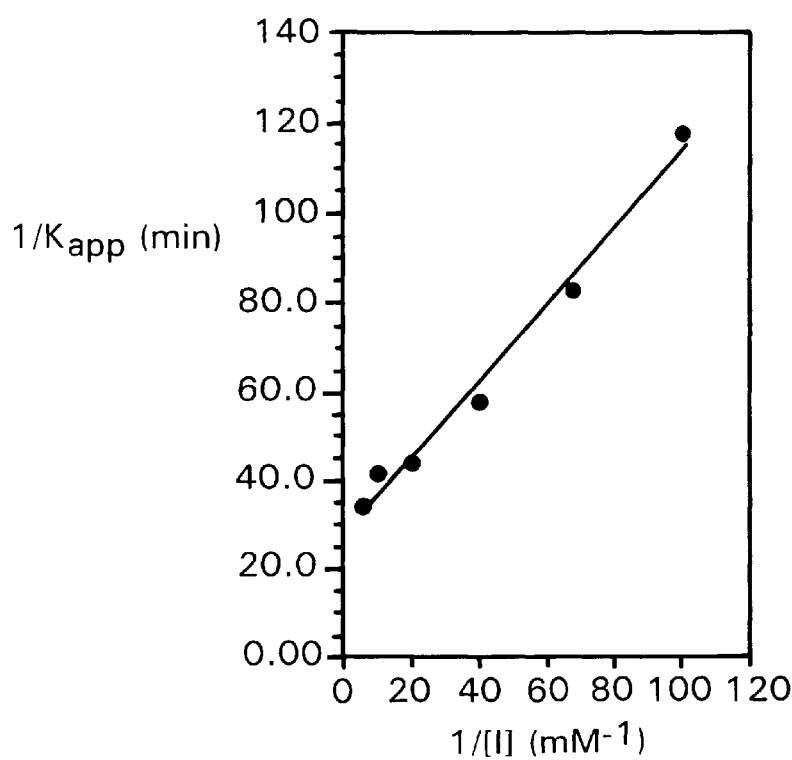
Figure 18:
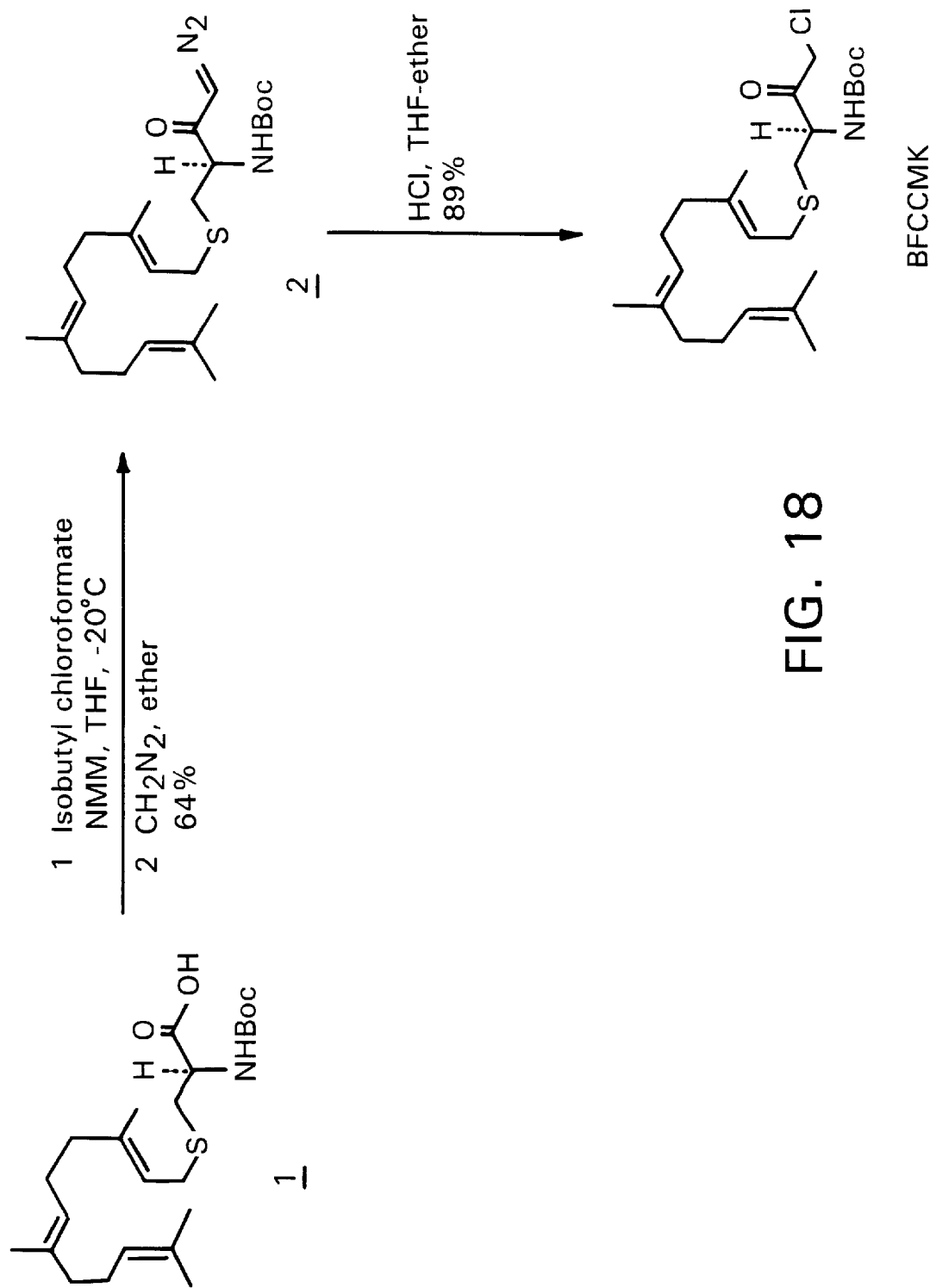
Figure 19:
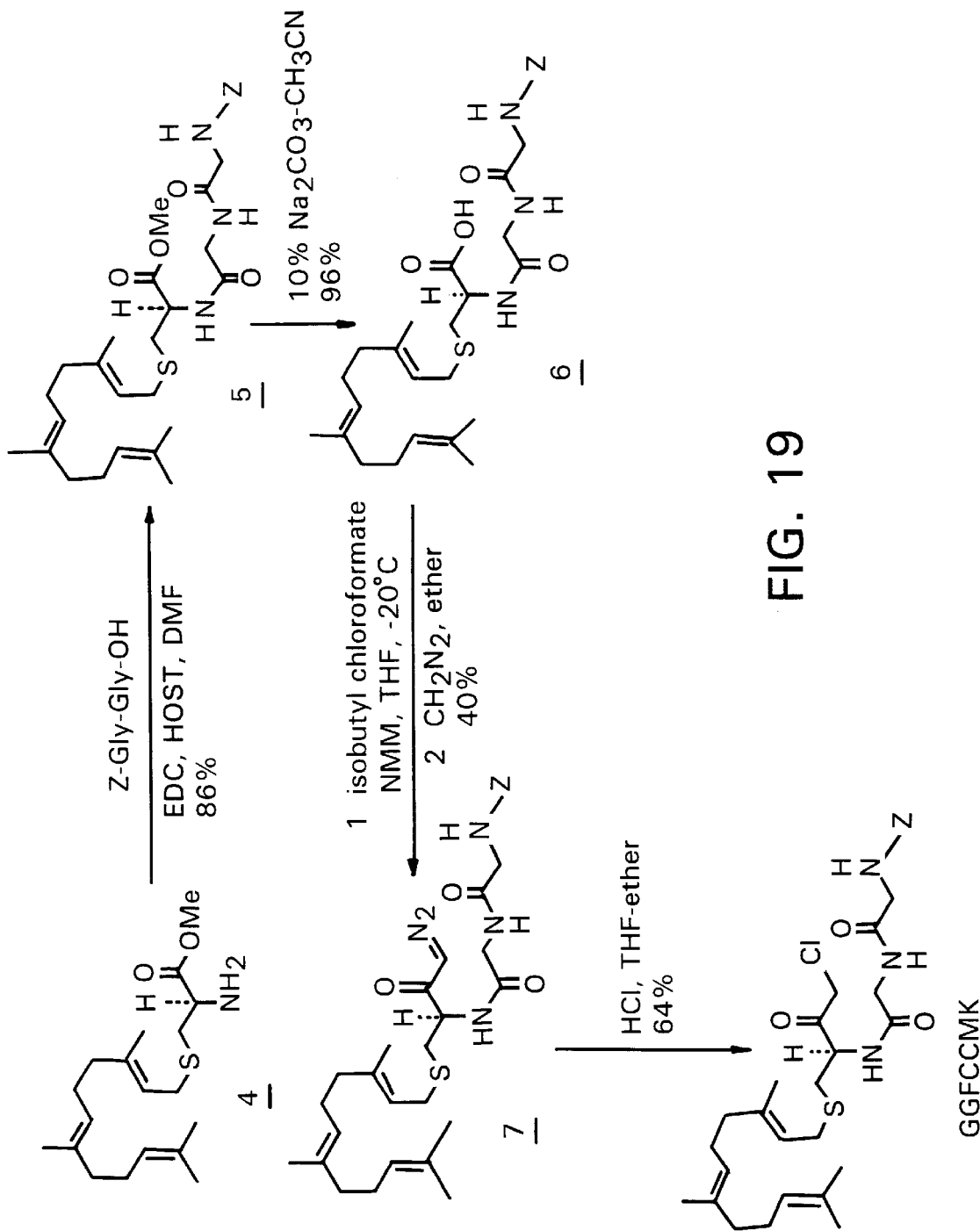
Figure 20:
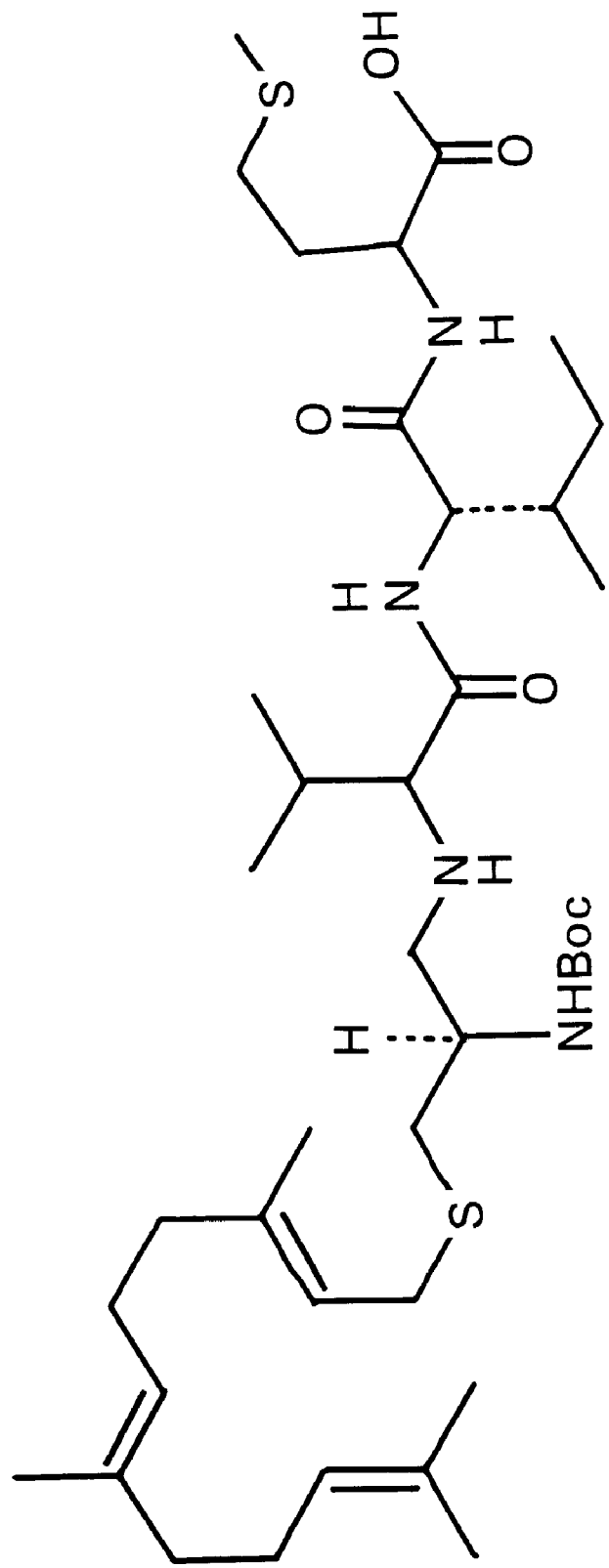
Figure 21:
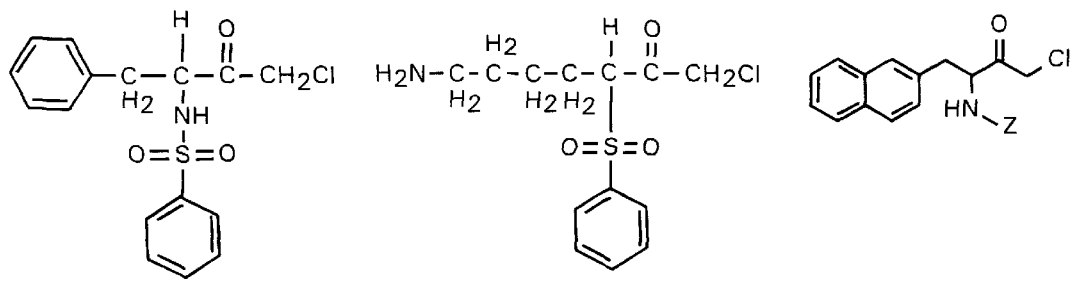
Figure 21:
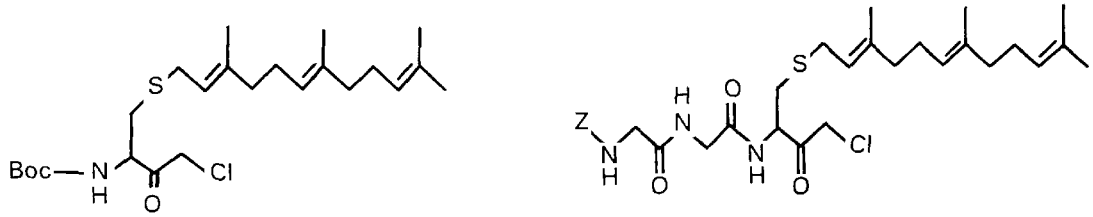
Figure 21:
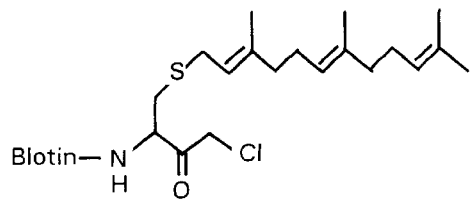

Since the $P_1$ position of natural substrates of this endoprotease is a farnesylcysteine residue, two farnesyleysteine chloromethyl ketone inhibitors, BFC-CMK and ZGGFCCMK, along with the structureally related anthranoyl derivative (Scheme 2 and Table IV) were tested. The results showed that BFCCMK and ZGGFCCMK were good inhibitors. The former has a 15-fold increase of the second-order rate constant ($K_{inh}/K_1=1164$ $M^{-1}$ $min^{-1}$), and the $K_1$ of the inhibitor-enzyme complex under the given conditions is $K_1=30$ $\mu M$ (FIG. 17). This is to be contrasted with a $K_1=1.1$ mM for TPCK. The fact that an analog like BFCCMK is a potent inactivator of the enzyme is important, because this observation strengthens the view that the enzyme inhibited does indeed recognize a farnesyl-L-cysteine moiety.

Figure 16A:
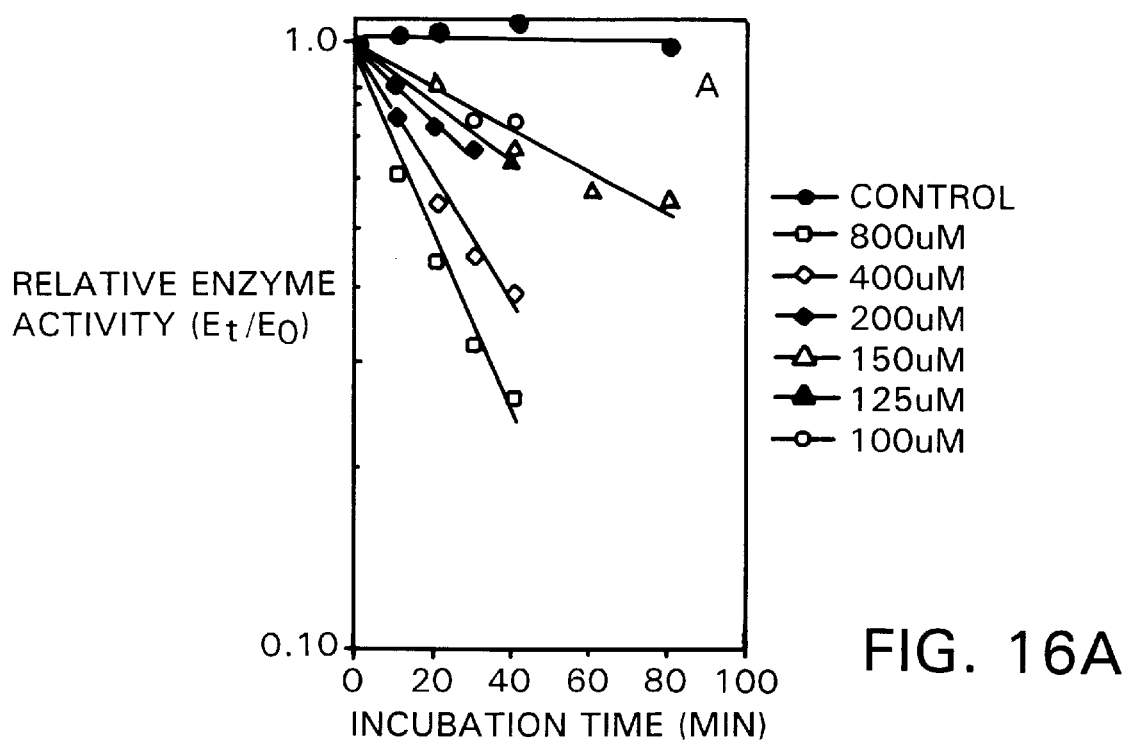

FIG. 16(A) Time-dependent inhibition. 16B Kitz-Wilson plot (the upper panel) for the inhibition of the isoprenylated protein endoprotease by TPCK. The inhibition studies were carried out at 37° C. using the solubilized endoprotease preparation. Aliquote of the inhibitor-enzyme solution were taken at interval times and diluted by a factor of 20, and the enzyme activity was assayed as described in Methods. (B) (the lower panel) the concentration-dependent inhibition of the endoprotease by TPCK. The inhibition studies were carried out at 37° C. The crude CHAPSO-solubilized endoprotease preparations (0.12 mg/mL) were preincubated for 60 min in 50 $\mu L$ of buffer E in the presence of 284 $\mu M$ TPCK or TLCK with 6% DMSO and 2% 2-propanol. After the incubation, the reaction solution was diluted by a factor of 20, and the remaining enzyme activity of the inhibitor-enzyme solution was assayed as described in Methods. Data were represented in mean from duplicate runs.

Some success was achieved, and a partially purified enzyme with circa 10-fold greater specific activity than that in the membrane preparation was obtained. Although levels of purification is modest, the protein itself might be much more purer than it appears, as it is certain that substantial activity is lost during purification. Attempts at the substantial purification of the enzyme did not meet with success, even though several different classes of columns were used. While an individual column might provide appreciable purification on the crude solubilized material, the column proved to be completely ineffective when used in series with other columns. It is likely that any substantial purification removes stabilizing entities or enzyme subunits, which would lead in either case to inactivation of the protease.

Figure 16B:
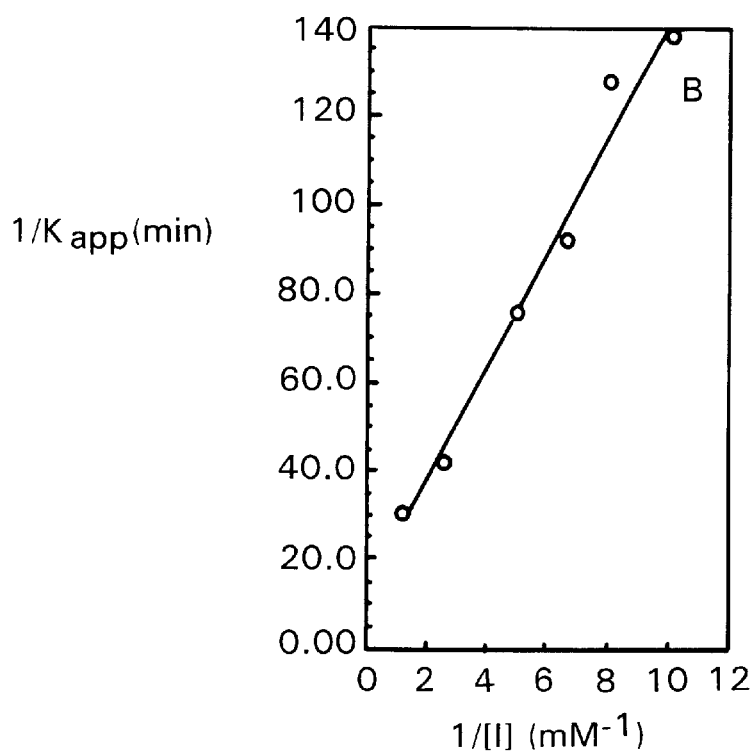
Figure 16C:
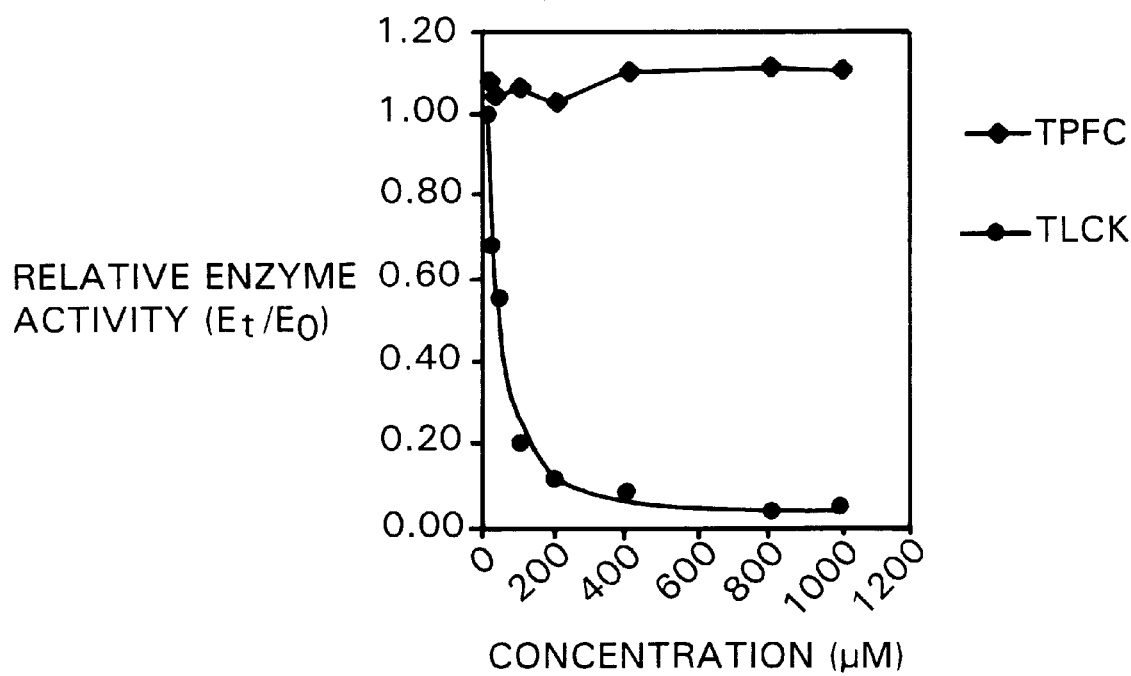

Studies on a few inhibitors suggest a required structural pattern for successful inhibition. Both TPCK and 2-Nal-Ala-CMK inhibit the endoprotease well (Table IV), but TLCK does not (FIG. 16B). This result is consistent with the fact that the primary binding pocket of the enzyme id hydrophobic, in order to accommodate the isoprenyl group of its natural substrates. It was of interest to synthesize and study analogs which actually contained a farnesyl moiety as the hydrophobic unit. In particular, BFCCMK proved to be quite a potent inactivator of the endoprotease, with a $K_1$ of approximately 30 $\mu M$. The $K_1$ for TPCK was approximately 1 mM, so the addition of the farnesyl moiety was salutary. This result is expected, given that the endoprotease is designed to hydrolyze isoprenylated proteins. Moreover, N-boc-S-all-trans-farnesyl-L-cysteine aldehyde proved to be a fairly potent competitive inhibitor of the enzyme (Ma et al., 1993). This inhibitor probably owes a good part of its potency to the aldehyde's ability to generate a tetrahedral intermediate with the active-site serine or cysteine residue (Vinitsky et al., 1992). The chloroketone moiety is similar to the aldehydic moiety with respect to its ability to form a tetrahedral intermediate with the active-site serine/cysteine (Powers, 1977; Prorok et al., 1994; Bender & Brubacher, 1967; Drenth et al., 1976; Shaw, 1990).

Only hydrophobic amino acid containing chloroketones inactivated the enzyme. BFCCMK, a chloroketone containing a farnesylcysteine moiety, proved to be the most potent inactivator of the endoprotease. A large number of chloroketone analogs which were not structurally similar to this analog were inert as endoprotease inactivators. This is important, because if further supports the idea that the mode of inhibition observed here is specific in nature.

The results with the inhibitors described above strongly suggest that the endoprotease is either a thiol protease or serine protease. Inhibition studies using the thiol group specific chemical reagent PCMB to inactivate the enzyme suggest that the enzyme may be a thiol protease. The enzyme is not inhibited by the serine reagent PMSF (1 mM), by chymostatin (0.33 mM), by BNPP (1 mM), or by the other serine protease inhibitors APMSF (20 $\mu M$), aprotinin (0.6 $\mu M$), leupeptin (1.0 $\mu M$), or DFP (1.0 mM) (Ma et al., 1993), suggesting that the endoprotease is not a serine protease. The endoprotease is also not inhibited by chelating reagents EDTA (10 mM) and 1,10-φ (1 mM). However, the enzyme is also insensitive to E-64 (0.5 mM) and IAA (0.4 mM), both of which inhibit some thiol proteases (Hanada et al., 1978; Gurd, 1972). It should be noted though that many cysteine proteases are sensitive to only a subset of thiol alkylating reagents. For example, the cysteine protease apopain (Nicholson et al., 1995) is inhibited by N-ethylma-leimide and iodoacetamide (IAA) but not by E-64, TLCK, and TPCK (Nicholson et al., 1995). The cysteine protease ICE is insensitive to E-64 and antipain but is inactivated by PCMB, iodoacetamide, and TPCK (Wilson et al., 1994). Of course, unambiguous evidence on the nature of the mechanistic class to which this endoprotease belongs will require the purification and/or cloning of the enzyme. While the traditional approach of purification of this enzyme may be exceedingly difficult to carry out successfully, indirect approaches using specific affinity labeling of the enzyme by chloroketones should be possible. Experiments of this type are the subject of current studies in this laboratory.

Experimental Procedures

Materials

Chromatography on gel filtration and ion exchange columns was performed on a LCC-500) FPLCC system (LKB Pharmacia Biotechnology, Inc.) All solutions used in FPLC were filtered using Millipore GS 0.22 μm filters. SDS-polyacrylamide gels were run using a Hoefer SE-250 slab gel electrophoresis unit. Radioactivity was determined on Berthold HPLC radioactivity monitor LB 506 C-1. Fresh bovine liver was obtained from a local slaughter house and stored at −80° C. CHAPSO was purchased from CALBIOCHEM. TPCK and chymostatin were from Fluka. TLCK and E-64 were from Boeringer & Mannheim. Dithiothreitol (DTT)m iodoacetamide (IAA), N,N'-phenanthroline (1,10-φ), and phenylmethansulfonyl fluoride (PMSF) were from Sigma. $H_2N$-Ala-Ala-Phe-CMK $H_2NAAFCMK$), Z-Ala-Pro-Phe-CMK (ZAPFCMK), Z-Gly-Gly-Phe-CMK (ZGG-FCMK), Z-Leu-Tyr-CMK (ZLYCMK), and β-(2-naphthyl)-L-Ala-CMK (2-NA1-Ala-CMK) were from BACHEM Bioscience, Inc. N-[$^3$H]Acetyl-S-farnesyl-L-cysteinyl-L-valyl-L-isoleucyl-L-methionine (Ma et al., 1992) (2.2 Ci/mmol) ([$^3$H]AFCVIM) and N-Boc-S-farnesyl-L-cysteinyl-$^\Psi$($CH_2$—NH)-valyl-L-isoleucyl-L-methionine or N-Boc-S-all-trans-farnesyl-L-Cys-$^\Psi$($CH_2$—HN)-(SEQ ID NO: 2) (RPI) (Ma et al., 1993) were gifts from Hoffman-La Roche. All reagents used is SDS-polyacrylamide gel electrophoresis were obtained from either Bio-Rad or Sigma. All other chemicals were of the highest quality available. Buffer A: 250 mM sucrose, 50 mM TEA, 50 mM KOAc, 6 mM Mg(OAc)$_2$, 1 mM EDTA, 1 mM DTT, and 0.5 mM PMSF (pH 7.5). Buffer B: 20 mM Tris-HCL (pH 7.0) containing 0.1 mM EDTA, and 1 mM PMSF. Buffer C: 20 mM Tris-HCL (pH 7.0), 1 mM EDTA, and 1 mM 1,10-φ. Buffer D: 20 mM Tris-HCl (pH 7.0), 1 mM EDTA, and 0.1% CHAPSO. Buffer E: 20 mM Tris-HCl (pH 7.0), 1 mM EDTA, 1 mM 1,10-φ, and 0.1% CHAPSO.

TABLE II

Enzyme Activity from the Washed Membranes and Supernatant[a]

| | | total activity | | | |
|---|---|---|---|---|---|
| | | | supernatants | | |
| incubation buffer | pellets (pmol min$^{-1}$) | (pmol · min$^{-1}$) | | normalized to detergent extract | combination of pellets and supernatants |
| 1% CHAPSO | 200 ± 14 | 527 ± 17 | | 100 ± 3 | 663 ± 27 |
| 10 mM Tris-HCl | 370 ± 8 | 12 ± 26 | | 2 ± 5 | 135 ± 35 |
| 0.5M NaCl | 1087 ± 70 | 22 ± 12 | | 4 ± 2 | 927 ± 43 |
| 0.5M NaBr/0.05% Tween-20 | 893 ± 2 | 3 ± 17 | (33 ± 7) | 0.6 ± 3 (6 ± 1) | 747 ± 20 |
| 4M urea | 610 ± 28 | 10 ± 9 | (20 ± 13) | 2 ± 4 (4 ± 2) | 620 ± 37 |
| membranes | 703 ± 143 | | | | |

[a]The membranes were frozen at −80° C. before they were used. The microsomal membranes were thawed at 4° C., homogenized manually, and incubated with 20 mM Tris-HCl buffer (pH 7.0) containing 0.1M PMSF, 1 mM EDTA, and 1 mM DTT, with 0.5M NaCl in the same Tris buffer, with 0.5M NaBr in the Tris buffer containing 0.05% Tween-20, and with 4M urea in the Tris buffer, respectively. The incubated mixtures werecentrifuged at 304000 g for 45 min. Data were presented in mean ± SD from two determinations, and data in parentheses were activity of the supernatants from NaBr and urea-treated mixtures which were dialyzed against buffer D, respectively. Enzyme activity was assayed as described in Methods. The other independent run from a different batch of bovine liver and membrane preparation gave similar results.

TABLE III

Partial Purification of an Isoprenylated Protein Endoprotease from Bovine Liver

| purification step | protein (mg) | specific activity (units/mg)[a] | total activity (units) | purification (fold) | recovery (%) |
|---|---|---|---|---|---|
| microsomal membranes | 44.1 ± 3.5 | 202 ± 7 | 8908 | 1 | 100 |
| detergent extract | 16.2 ± 1.2 | 430 ± 13 | 6966 | 2.1 | 77 |

TABLE III-continued

Partial Purification of an Isoprenylated Protein Endoprotease from Bovine Liver

| purification step | protein (mg) | specific activity (units/mg)[a] | total activity (units) | purification (fold) | recovery (%) |
|---|---|---|---|---|---|
| Resource Q | 2.2 ± 0.1 | 1000 ± 24 | 2200 | 5.0 | 25 |
| Superose 12 | 0.51 ± 0.06 | 1824 ± 118 | 930 | 9.0 | 10 |

[a]The endoprotease activity was assayed as described in Methods. Specific activity (units/mg) is expressed as picomoles of N-[$^3$H]acetyl-S-farnesyl-L-cysteine per min per milligram of protein; total activity (units) is picomoles of N-[$^3$H]acetyl-S-farnesyl-L-cysteine per min. Data were presented as mean ± SD (n = 3–6).

TABLE IV

Inhibition of the Isoprenylated Protein Endopeptidase with a Variety of Inhibitors[a]

| | | enzyme activity (%) | |
|---|---|---|---|
| inhibitors | concentration | detergent extract | partially purified |
| control (no inhibitor) | | 100 ± 5 | 100 ± 5 |
| BNPP | 1 mM | 100 ± 8 | |
| Chymostatin | 0.33 mM | 104 ± 8 | 99 ± 1 |
| DTT | 5 mM | 108 ± 8 | 106 ± 6 |
| E-64 | 0.11 mM | 113 ± 0 | |
| | 0.5 mM | | 103 ± 4 |
| 1,10-φ | 1 mM | 90 ± 10 | 102 ± 14 |
| PCMB | 0.5 mM | 0 ± 5 | |
| | +5 mM DTT | 44 ± 4 | |
| | 0.1 mM | 0 ± 6 | |
| | 5 μm | | 33 ± 3 |
| PMSF | 1 mM | 93 ± 3 | |

[a]All data were presented in mean ± SD from 2–6 determinations.

TABLE V

Inhibition of the Isoprenylated Protein Endopeptidase by Halomethyl Ketone Inhibitors[a]

| inhibitors | concentration (μM) | enzyme activity (%) | $K_{inh}$ (s$^{-1}$) | $K_1$ (μM) | $K_{inh}/K_1$ (M$^{-1}$ min$^{-1}$) |
|---|---|---|---|---|---|
| control | | 100 ± 3 | | | |
| TPCK | 284 | 43 ± 5 | (1.4 ± 0.6) × 10$^{-3}$ | 1100 ± 500 | 77 ± 6 |
| TLCK | 1000 | 94 ± 15 | | | |
| 2-Nal-Ala-CMK | 284 | 53 ± 1 | | | |
| BFCCMK | 284 | 27 ± 2 | (5.9 ± 0.4) × 10$^{-3b}$ | 30 ± 2[b] | 1164 ± 60[b] |
| ZGGFCCMK | 284 | 44 ± 1 | | | |

Figure 7:
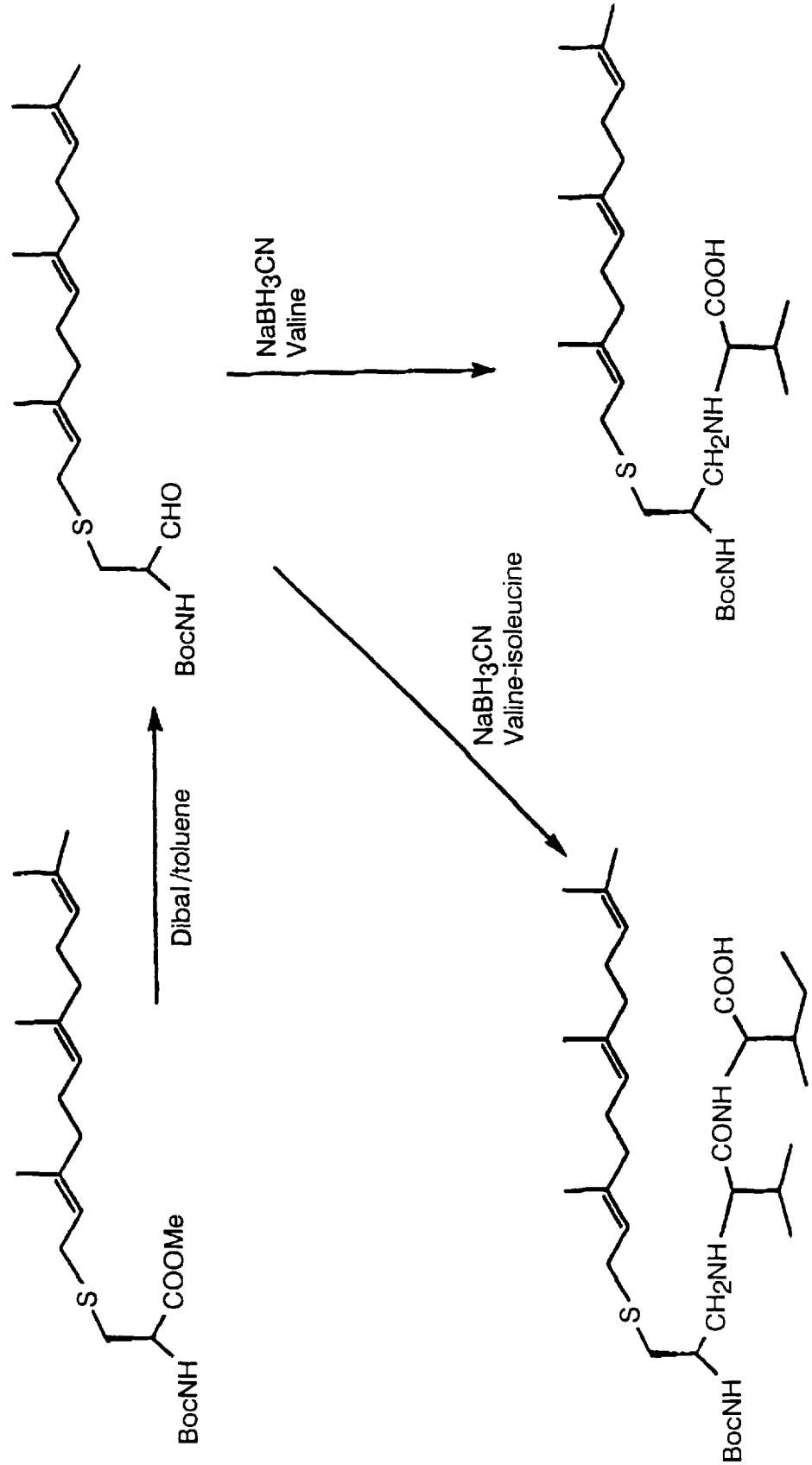
FIGS. 7, 8, and 9 are schematic illustrations of the synthesis of reduced peptide inhibitors.
Figure 8:
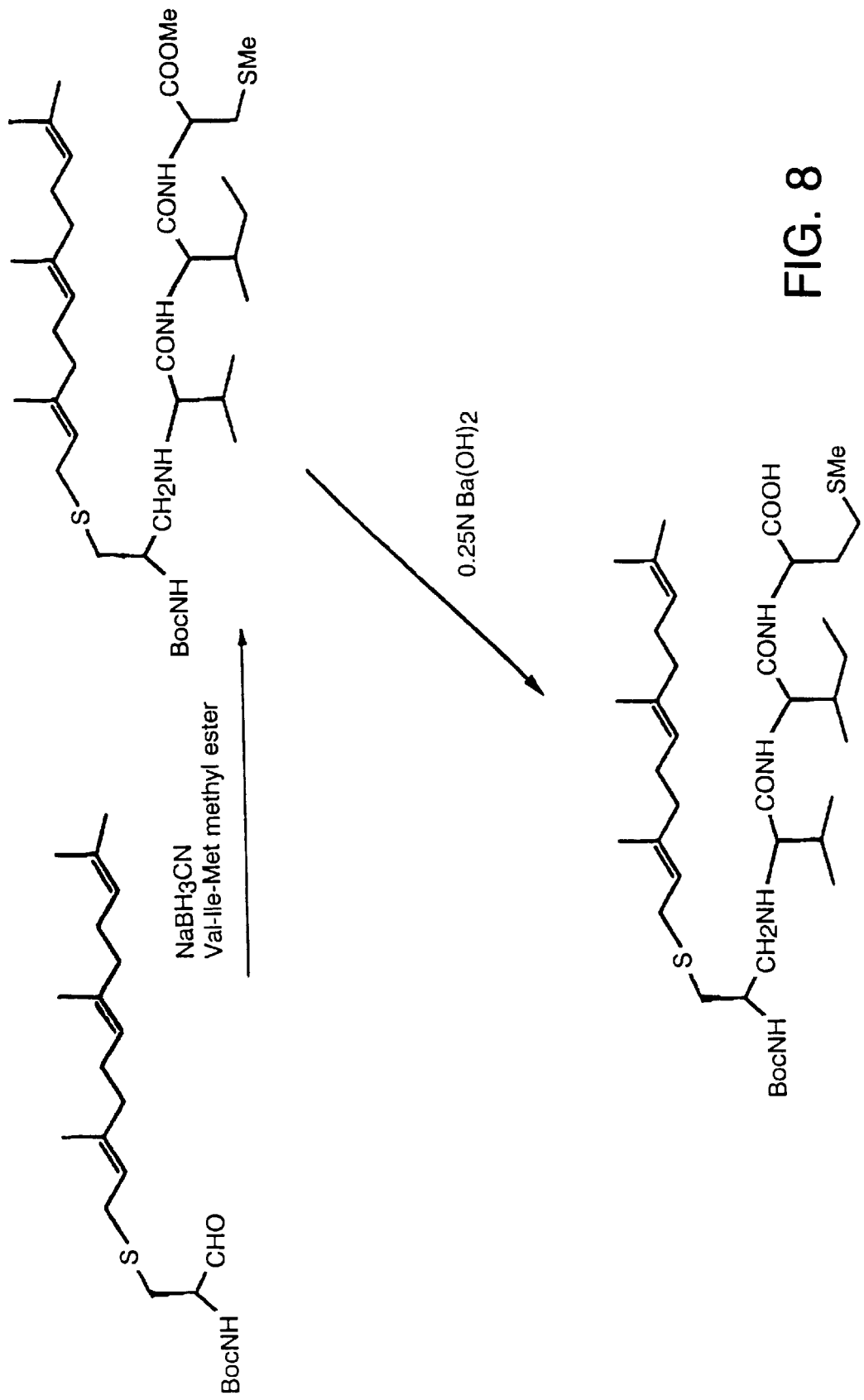
Figure 9:
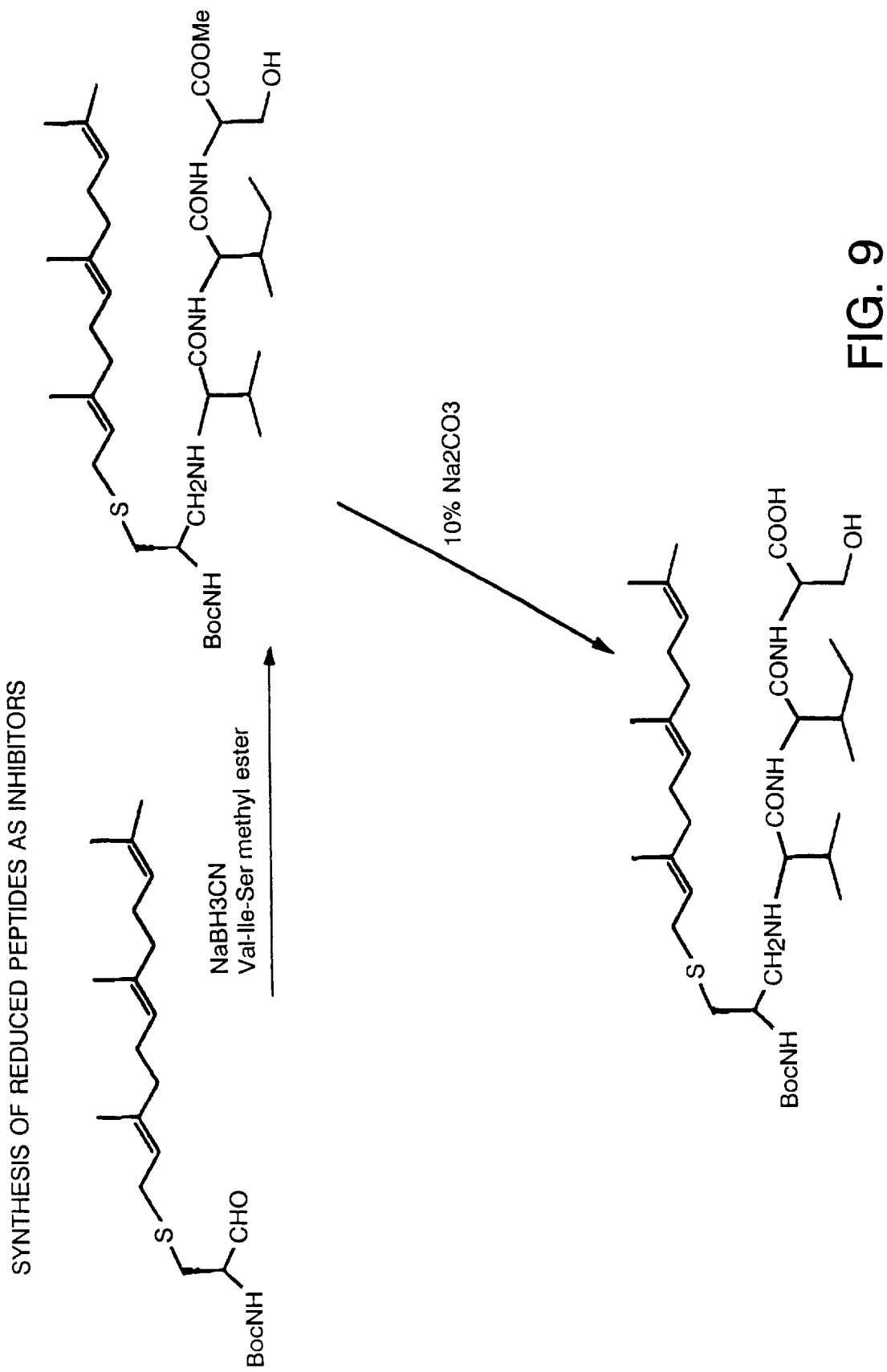
Figure 10A:
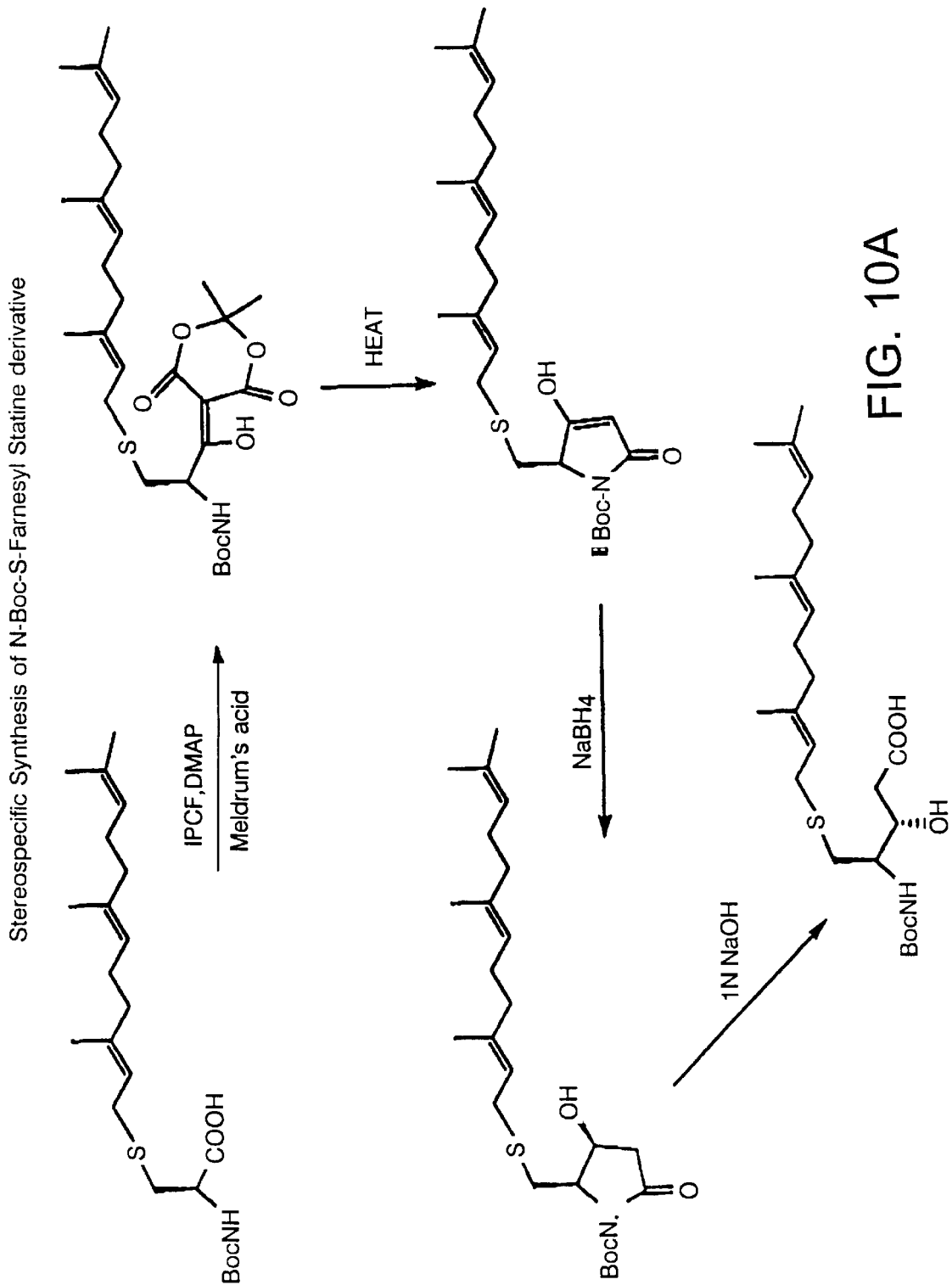
Figure 10B:
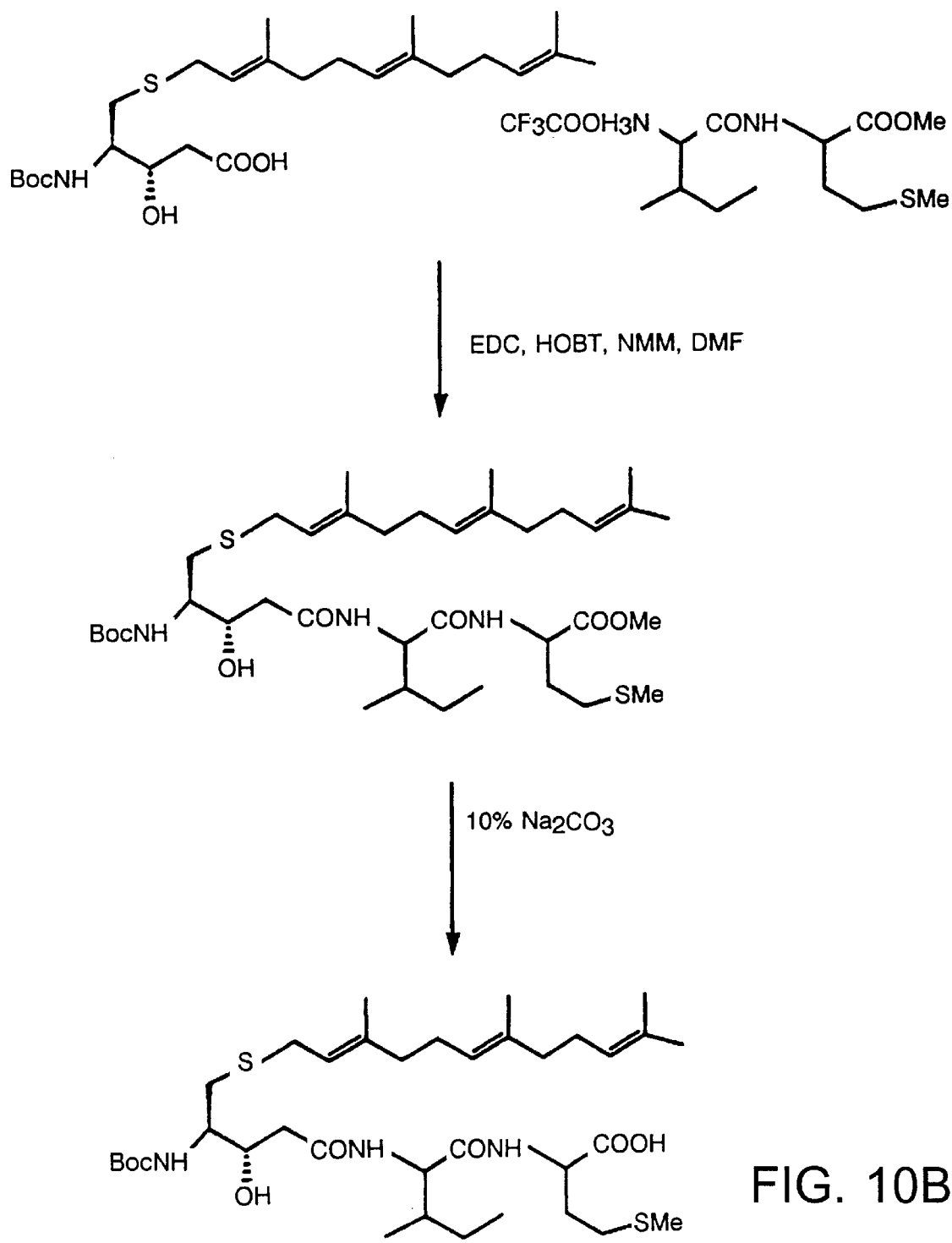
Figure 10C:
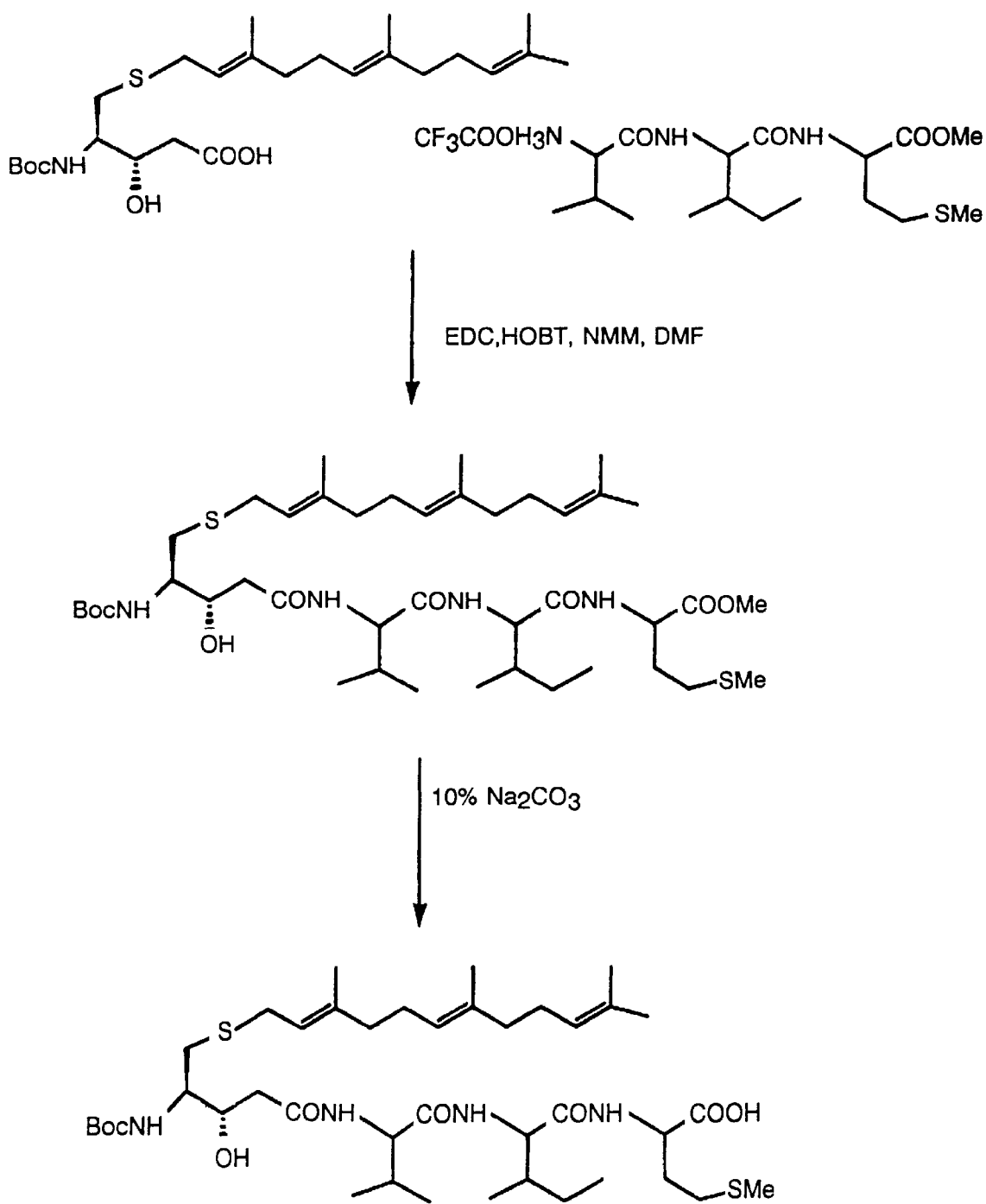

[a]Inhibition procedures and assay conditions were described in Methods. Data were represented in mean ± SD from two independent runs (four determinations) to six independent runs. The enzyme activity in the absence of inhibitor was used as a control and normalized to 100%.
[b]The values were obtained from the Kitz-Wilson plot using the partially purified enzyme preparation (FIG. 7).

TABLE VI

Inhibition of Isoprenylated Protein Endoprotease by Halomethyl Ketone Inhibitors[a]

| Inhibitors | Structures | Enz.Act. (%)/Conc. |
|---|---|---|
| CONTROL | | 100 ± 3 |
| BFCMK | 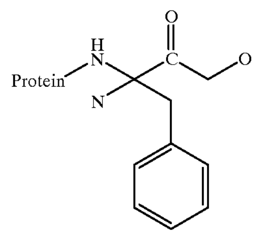 | |
| STLCK | 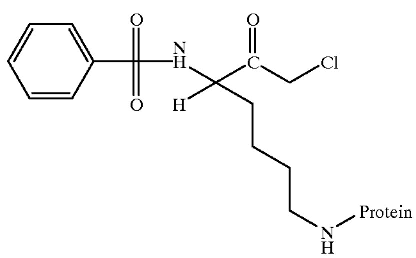 | |
| octyl-LC-Biotin | 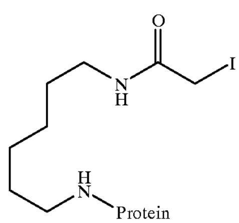 | |
| 1AA | 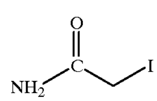 | |
| M$_R$MAAFCMK | 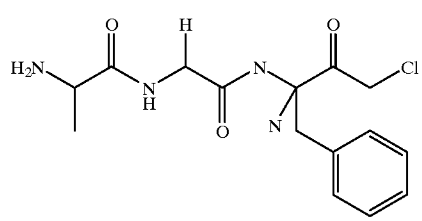 | |
| ZOOFCMK | 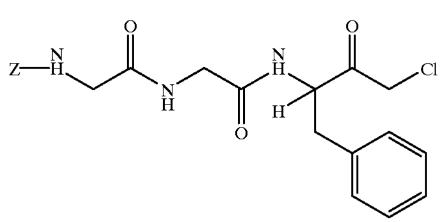 | |

TABLE VI-continued

Inhibition of Isoprenylated Protein Endoprotease by Halomethyl Ketone Inhibitors[a]

| Inhibitors | Structures | Enz.Act. (%)/Conc. |
|---|---|---|
| ZAPFCMK | 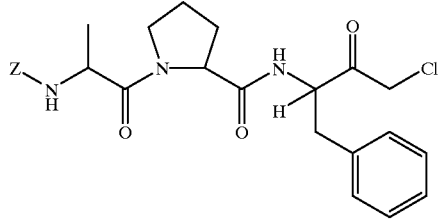 | |
| ZL.YCMK | 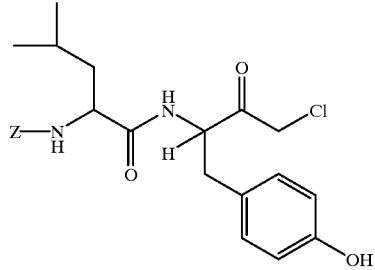 | |

[a]The experimental conditions were the same as described in the footnotes to Table IV

REFERENCES

Akopyan, T. N., Couedel, Y., Orlowski, M., Fournie-Zaluski, M.-C., & Roques, B. P. (1994) *Biochem. Biophys. Res. Commun.* 198, 787–794.

Ashby, M. N., King, D. S., & Rine, J. (1992) *Proc. Natl. Acad. Sci. U.S.A.* 89, 4613–4617.

Bender, M. L. & Brubacher, L. J. (1966) *J. Am. Chem. Soc.* 88, 5880–5889.

Bodanszky, M., & Bodanszky, A. (1994) *The Practice of Peptide Synthesis* 2nd ed., Springer-Verlag, New York.

Chen, Y. (1995) ASBMB/DBC-ACS Joint Meeting in San Francisco, Late Breaking Abstract No. LB 46.

Drenth, J., Kalk, K. H., & Swen, H. M. (1976) *Biochemistry* 15, 3731–3738.

Gibbs, J. B. (1991) *Cell* 65, 1–4.

Green, G. D. J., & Shaw, E. (1981) *J. Biol. Chem.* 236, 1923–1928.

Gurd, F. R. N. (1972) *Methods Enzymol.* 25, 424–438.

Hanada, K., Tamai, M., & Yamagishi, M. (1978) *Agric. Biol. Chem.* 42, 523–528.

Characterization of Isoprenylated Protein Endoprotease K

Hancock, J. F. (1993) *Curr. Biol.* 3, 770–772.

Hancock, J. F., Cadwallader, K., & Marshall, C. (1991) *EMBO J.* 10, 641–646.

Hjemeland, L. M., Nebert, D. W., & Osborne, J. C., Jr. (1983) *Anal. Biochem.* 130, 72–82.

Jang, G.-F., Yokoyama, K., & Gelb, M. H. (1993) *Biochemistry* 32, 9500–9507.

Kettner, C., & Shaw, E. (1981) *Methods Enzymol.* 80, 826–842.

Laemmli, U. K. (1970) *Nature* 227, 680–685.

Lowry, O. H., Rosebrough, N. J., Farr, A. L., & Randall, R. J. (1951) *J. Biol. Chem.* 193, 265–275.

Kitz, R., & Wilson, I. B. (1962) *J. Biol. Chem.* 237, 3245–3249.

Ma, Y.-T., & Rando, R. R. (1992) *Proc. Natl. Acad. Sci. U.S.A.* 89, 6275–6279.

Ma, Y.-T., Chaudhuri, A., & Rando, R. R. (1992) *Biochemistry* 31, 11772–11777.

Ma, Y.-T., Gilbert, B. A., & Rando, R. R. (1993) *Biochemistry* 32, 2386–2393.

Ma, Y.-T., Shi, Y.-Q., Lim, Y. H., McGrail, S. H., Ware, J. A., & Rando, R. R., (1994) *Biochemistry* 33, 5414–5420.

Manne, V., Roberts, D., Tobin, A., O'Rourke, E., DeVirgilio, M., Meyers, C., Ahmed, N., Kurz, B., Resh, M., Kung, H.-F., & Barbacid, M (1990) *Proc. Natl. Acad. Sci. U.S.A.* 87, 7541–7545.

Nicholson, D. W., Ali, A., Thornberry, N. A., Vaillancourt, J. P., Ding, C. K., Gallant, M., Gareau, Y., Griffin, P. R., Labelle, M., Lazebnik, Y. A., Munday, N. A., Raju, S. M., Smulson, M. E., Yamin, T.-T., Yu, V. L., & Miller, D. K. (1995) *Nature* 376, 37–43.

Powers, J. C. (1977) *Chem. Biochem. Amino Acids, Pept. Proteins* 4, 65–178.

Prorok, M., Albeck, A., Foxman, B. M., & Abeles, R. H. (1994) *Biochemistry* 33, 9784–9790.

Reiss, Y., Goldstein, J. L., Seabra, M. C., Casey, P. J., & Brown, M. S. (1990) *Cell* 62, 81–88.

Schaber, M. D., O'Hara, M. B., Garsky, V. M., Mosser, S. D., Bergstrom, J. D., Moores, S. L., Marshall, M. S., Friedman, P. A., Dixon, R. A. F., & Gibbs, J. B. (1990) *J. Biol. Chem.* 265, 14701–14704.

Schoellmann, G., & Shaw, E. (1963) *Biochemistry* 2, 252–255.

Shaw, E. (1990) *Adv. Enzymol. Rel. Areas Mol. Biol.* 63, 271–347.

Shaw, E., & Ruscica, J. (1971) *Arch. Biochem. Biophys:* 145, 484–489.

Vinitsky, A., Michaud., C., Powers, J. C., & Orlowski, M. (1992) *Biochemistry* 31, 9421–9428.

Walter, P., & Blobel, G. (1983) *Methods Enzymol.* 96, 84–93.

Whitaker, J. R., & Perez-Villasenor, J. (1968) *Arch. Biochem. Biophys.* 124, 70–78.

Wilson, K. P., Black, J. F., Thomson, J. A., Kim, E. E., Griffith, J. P., Navia, M. A., Murcko, M. A., Chambers, S. P., Aldape, R. A., Raybuck, S. A., & Livingston, D. J. (1994) *Nature* 370, 270–275.

Abbreviations

AdoMet, S-(5'-adenosyl)-L-methionine chloride; AFC, N-acetyl-S-farnesyl-L-cysteine; AFCVIM, N-acetyl-S-farnesyl-L-cysteinyl-L-valyl-L-isoleucyl-L-methionone or N-acetyl-S-farnesyl-L-(SEQ ID NO: 2); APMSF, 4-(amidinophe-nyl)methanesulfonyl fluoride; BFCCMK, N-tert-Boc-S-farnesyl-L-cysteine chloromethyl ketone; BFCMK, N-biotinyl-L-phenylalanine chloromethyl keton; Boc, tert-butyloxylcarbonyl; BNPP, bis(p-nitro-phenyl) phosphate; BTLCK, N-biotinyl-Nα-tosyl-L-lysine chloromethol ketone; CHAPSO, 3-[(3-cholamidopropyl) dimethylammonio]-2-hy-droxy-1-propanesulfonate; CHAPS, 3-[(cholamidopropyl)dimethyl-lammonio]-1-propanesulfonate; CMC, critical micellization concentration; CMK, chloromethyl ketone; CTAB, cetyltrimethylammonium bromide; DPF, diisopropyl fluorophosphate; DMF, dimethyl formamide; DMSO, dimethyl sulfoxide, DTT, dithiothreito; E-64, N-[N-(L-3-trans-carboxyoxiran-2-carbonyl)-L-leucyl]agmatine; EDTA, ethylenediaminetetraacetic acid; EDC, 1-[3-(dimethylamino)propyl]-3-ethycarbodiumide; 1,10-φ, N,N'-phenanthroline; $H_2$NAAFCMK, L-alayl-L-alaynl-L-phenylalanine chloromethyl ketone; HOBT, 1-hydroxybenzotriazole hydraaate; IAA, iodoacetamide; ICE, interleukin-1β converting enzyme; 2-NAL-ALA-CMK, β-(2-naphthyl)-L-alanine chloromethyl ketone; NMM, N-methylmorpholine; PCMB, p-chloromercuribenzoate; PMSF, phenylmethanesulfonyl fluoride; RPI, N-Boc-S-farnesyl-L-cysteine-Ψ-($CH_2$—NH)-valyl-L-isoleucyl-L-methionine or N-Boc-S-all-trans-farnesyl-L-Cys-Ψ($CH_2$—HN)-(SEQ ID NO: 2); SDS-PAGE, sodium dodecyl sulfate-polyacrylamide gel electrophoresis; TEA, triethanolamine; THF, tetrahydrofuran; TLCK, Nα-tosyl-L-lysine chloromethyl ketone; TPCK, Nα-tosyl-L-phenylalamine chloromethyl ketone; Tris-HCl, 2-amino-2-(hydroxymethyl)-1,3-propanediol hydrochloride; Z, benzyloxycarbonyl; ZAPFCMK, N-benzyloxycarbonyl-L-alanyl-L-prolyphenylalanine chloromethyl ketone; ZGGFCCMK, N-benzyloxycarbonyl-glycylglycyl-S-farnesyl-L-cysteine chloromethyl ketone; ZGGFCMK, N-benzyloxylcarbonylglycyglycyl-L-phenylalamine chloromethyl ketone; Z-gly-gly-OH, N-benzyloxycarbonylglycylglycinel ZLYCMK, N-benzyloxylcarbonyl-L-leucyl-L-tryosyl chloromethyl ketone; A, alanine; Ali, aliphatic amino acid; aa, amino acid; C, cysteine, CAAX, Cys-Ali-Ali-Xaa; F, phenylalanine; G, glycine, L, leucine, P, proline; X, an undefined amino acid; Y, tyrosine.

---

I claim the following:

1. A compound of the formula:

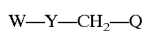

wherein

W is selected from the group consisting of: a) a farnesyl group, b) a geranylgeranyl group, c) a substituted farnesyl group, d) a substituted geranylgeranyl group, and e) a lipophilic alkyl, alkenyl, aryl or arylalkyl hydrocarbon group having between 10 and 20 carbon atoms;

Y is:

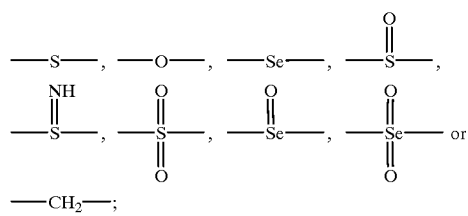

Q is

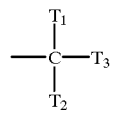

wherein $T_1$ is: H, F, $CH_3$, or —$(CH_2)_n$—$X_1$;

$T_2$ is: —N-benzyloxycarbonyl (Boc), —N—φ wherein $X_1$ is: —SH, —COOH, or —$CONH_2$; and n is an integer less than 20; and φ is an amino acid or polypeptide residue;

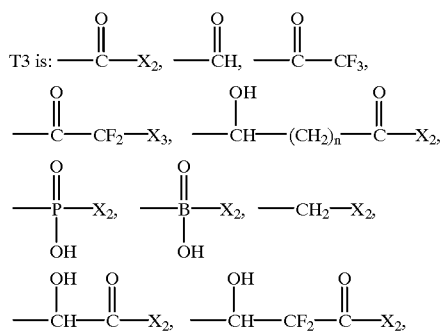

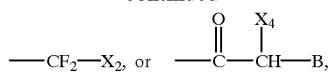

where $X_4$ is a halogen or —H, and B is an amino acid; and wherein $X_2$ is a peptide of 20 or fewer amino acids linked to carbon via the amino terminal nitrogen of said peptide; $X_3$ is a peptide of 20 or fewer amino acids linked via an alpha carbon of said peptide; and n is an integer less than 20, said compound being characterized by inhibiting enzymatic proteolysis of acetyl-S-farnesyl-L-cysteinyl-L-valyl-L-isoleucyl-L-methionine producing N-acetyl-S-farnesyl-L-cysteine by an endoprotease activity, said endoprotease activity being present in a solubilized membrane-bound bovine liver microsomal membrane preparation which has been purified by ion exchange.

2. The compound of claim 1 in which W is a n-alkyl group or n-alkenyl group.

3. The compound of claim 1 in which W is a β-napthyl group.

4. The compound of claim 1 wherein Y is —S—.

5. The compound of claim 1 in which W is n-docecyl.

6. The compound of claim 1 in which $T_3$ is a halo methyl ketone or —CO—CHXφ, where φ is as defined above.

7. The compound of claim 1 in which W is phenyl and Y is $CH_2$.

8. The compound of claim 1 in which $T_2$ is

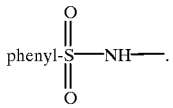

9. The compound of claim 1 in which $T_2$ is biotin-NH.

10. The compound of claim 1 in which the compound is a) N-biotinyl-S-farnesyl cysteine chloromethyl ketone; b) N-Boc-S-dodecylcysteine chloromethyl ketone; or N-Boc-S-Decyl Cysteine chloromethyl ketone.

11. The compound of claim 1 in which the compound is ZGGFCCMK, BFCCMK, TPCK, 2-Nal-Ala-CMK, or BTLCK.

12. The compound of claim 1 in which the compound is an irreversible inhibitor of said enzymatic proteolysis.

13. A method for preparing a medicament for inhibiting neoplastic cell growth, said method comprising admixing the inhibitor of claim 1 with a pharmaceutically acceptable carrier.

* * * * *

```
                      SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:1:

Cys Val Ile Ser
  1

(2) INFORMATION FOR SEQ ID NO:2:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:2:

Cys Val Ile Met
  1

(2) INFORMATION FOR SEQ ID NO:3:

(i) SEQUENCE CHARACTERISTICS:
          (A) LENGTH: 4 amino acids
          (B) TYPE: amino acid
          (D) TOPOLOGY: linear
```

(ii) MOLECULE TYPE: peptide (xi) SEQUENCE DESCRIPTION: SEQ ID NO:3:

Cys Ala Ala Xaa